(12) United States Patent
Wang et al.

(10) Patent No.: US 7,897,605 B2
(45) Date of Patent: *Mar. 1, 2011

(54) PYRIMIDINE COMPOUNDS

(75) Inventors: Shudong Wang, Nottingham (GB); Christopher Meades, Dundee (GB); Gavin Wood, Cupar Fife (GB); Janice O'Boyle, Dundee (GB); Campbell McInnes, Irmo, SC (US); Peter Martin Fischer, Beeston (GB)

(73) Assignee: Cyclacel Limited, Dundee (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/220,857

(22) Filed: Jul. 29, 2008

(65) Prior Publication Data

US 2008/0287439 A1  Nov. 20, 2008

Related U.S. Application Data

(63) Continuation of application No. 10/991,942, filed on Nov. 17, 2004, now Pat. No. 7,432,260, which is a continuation of application No. PCT/GB2003/004973, filed on Nov. 14, 2003.

(30) Foreign Application Priority Data

Nov. 14, 2002  (GB) .................................. 0226583.3

(51) Int. Cl.
*C07D 417/04* (2006.01)
*A61K 31/506* (2006.01)

(52) U.S. Cl. .............................. 514/252.14; 514/235.8; 514/275; 544/122; 544/295; 544/331

(58) Field of Classification Search ................ 544/122, 544/295, 331; 514/235.8, 252.14, 275
See application file for complete search history.

(56) References Cited

U.S. PATENT DOCUMENTS

| 6,531,479 | B2 | 3/2003 | Wang et al. |
| 6,699,854 | B2 | 3/2004 | Wang et al. |
| 7,262,202 | B2 | 8/2007 | Fischer et al. |
| 7,432,260 | B2 | 10/2008 | Wang et al. |
| 2005/0282843 | A1 | 12/2005 | Wang et al. |
| 2005/0288307 | A1 | 12/2005 | Wang et al. |
| 2006/0241297 | A1 | 10/2006 | Wang et al. |
| 2006/0264628 | A1 | 11/2006 | McInnes et al. |
| 2007/0021419 | A1 | 1/2007 | Wang et al. |
| 2007/0021452 | A1 | 1/2007 | Wang et al. |
| 2007/0270442 | A1 | 11/2007 | Green et al. |

2008/0125404 A1  5/2008  Benigni et al.

FOREIGN PATENT DOCUMENTS

| WO | WO-97/19065 A1 | 5/1997 |
| WO | WO-01/72745 A1 | 10/2001 |
| WO | WO-03/029248 A1 | 4/2003 |

OTHER PUBLICATIONS

Bosseray, A. et al., "What's new in vaccines against herpes simplex infections?" *Pathol. Biol.* (Paris), vol. 50(8):483-92 (2002).
Cotsarelis, George et al., "Towards a molecular understanding of hair loss and its treatment," *Trends in Molecular Medicine*, vol. 7(7):293-301 (2001).
Damasio, Antonio R., "Alzheimer's Disease and Related Dementias," *Cecil Textbook of Medicine*, 20th Edition, W.B. Saunders Company, J. Claude Bennett, Ed., vol. 2:1992-1996 (1996).
Douglas, R. Gordon Jr., "Introduction to Viral Diseases," *Cecil Textbook of Medicine*, 20th Edition, W.B. Saunders Company, J. Claude Bennett, Ed., vol. 2:1739-1747 (1996).
Goff, Stephen P., "Intracellular trafficking of retroviral genomes during the early phase of infection: viral exploitation of cellular pathways," *The Journal of Gene Medicine*, vol. 3:517-528 (2001).
Layzer, Robert B., "Degenerative Diseases of the Nervous System," *Cecil Textbook of Medicine*, 20th Edition, W.B. Saunders Company, J. Claude Bennett, Ed., vol. 2:2050-2057 (1996).
Razonable, R.R. et al., "Herpesvirus infections in transplant recipients: current challenges in the clinical management of cytomegalovirus and Epstein-Barr virus infections," *Herpes*, vol. 10(3):60-65 (2003).
Simone, Joseph V., "Introduction," *Cecil Textbook of Medicine*, 20th Edition, W.B. Saunders Company, J. Claude Bennett, Ed., vol. 1:1004-1010 (1996).

*Primary Examiner*—Deepak Rao
(74) *Attorney, Agent, or Firm*—Nelson Mullins Riley & Scarborough LLP; Cynthia L. Kanik; Brian C. Trinque

(57) ABSTRACT

The present invention relates to substituted pyrimidines of formula I, their preparation, pharmaceutical compositions containing them and their use as inhibitors of cyclin-dependent kinases (CDKs) and hence their use in the treatment of proliferative disorders and/or viral disorders.

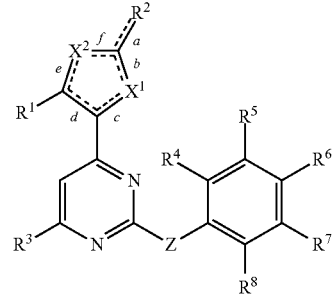

6 Claims, No Drawings

PYRIMIDINE COMPOUNDS

RELATED APPLICATIONS

This application is a continuation of U.S. Ser. No. 10/991,942, filed on Nov. 17, 2004, which is a continuation of PCT/GB2003/004973, filed on Nov. 14, 2003, which claims priority to GB 0226583.3, filed on Nov. 14, 2002. The entire contents of each of these applications is incorporated herein by reference in their entirety.

BACKGROUND

We have previously disclosed 2-substituted-4-heteroaryl-pyrimidines and their use in the treatment of proliferative disorders (Fischer P M, Wang S. PCT Intl. Patent Appl. Publ. WO 01/072745; Cyclacel Limited, UK, 2001). These compounds inhibit cyclin-dependent protein kinases (CDKs), in particular CDK4/cyclin D, CDK2/cyclin E, CDK2/cyclin A, and CDK1/cyclin B, i.e. enzyme complexes that are important in human cell cycle progression. Furthermore, 2-phenylamino-4-heteroaryl-pyrimidines possess selective in vitro and in vivo antiproliferative activity against a range of human tumour cells (Wang S, Blake D, Clarke R, Duff S, McClue S J, McInnes C, Melville J, Stewart K, Taylor P, Westwood R, Wood G, Wu S-Y, Zhelev N Z, Zheleva D I, Walkinshaw M, Lane D P, Fischer P M. Proc. Amer. Assoc. Cancer Res. 2002; 43: 4202).

The present invention seeks to provide further 2-substituted-4-heteroaryl-pyrimidines. More specifically, the present invention preferably seeks to provide 2-substituted-4-heteroaryl-pyrimidines which display improved aqueous solubility and/or bioavailability.

STATEMENT OF INVENTION

The present invention relates to new 2-substituted-4-heteroaryl-pyrimidine derivatives and their use in therapy. More specifically, the invention relates to 2-substituted-4-heteroaryl-pyrimidine derivatives having improved solubility properties.

A first aspect of the invention relates to a compound of formula I, or a pharmaceutically acceptable salt thereof,

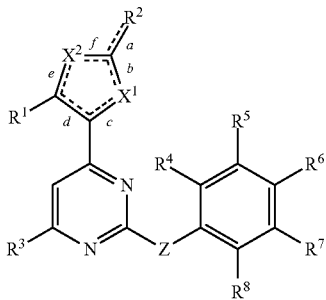

I wherein:
(A) one of $X^1$ and $X^2$ is S, and the other of $X^1$ and $X^2$ is N;
"a" is a single bond;
"b", "c", "d", "e" and "f" are single or double bonds so as to form a thiazolyl ring;
$R^2$ is independently as defined below for $R^1$, $R^{3-8}$; or
(B) one of $X^1$ and $X^2$ is S, and the other of $X^1$ and $X^2$ is $NR^{17}$;
"a" and "d" are each double bonds;
"b", "c", "e" and "f" are each single bonds;
$R^2$ is oxo; and
$R^{17}$ is H or alkyl;

where:
Z is NH, NHCO, NHSO$_2$, NHCH$_2$, CH$_2$, CH$_2$CH$_2$, CH=CH, SO$_2$, or SO;
$R^1$, $R^3$, $R^4$, $R^5$, $R^6$, $R^7$ and $R^8$ are each independently H, alkyl, alkyl-$R^9$, aryl, aryl-$R^9$, aralkyl, aralkyl-$R^9$, halogeno, NO$_2$, CN, OH, O-alkyl, COR$^9$, COOR$^9$, O-aryl, O—R$^9$, NH$_2$, NH-alkyl, NH-aryl, N-(alkyl)$_2$, N-(aryl)$_2$, N-(alkyl)(aryl), NH—R$^9$, N—(R$^9$)(R$^{10}$), N-(alkyl)(R$^9$), N-(aryl)(R$^9$), COOH, CONH$_2$, CONH-alkyl, CONH-aryl, CON-(alkyl)(R$^9$), CON(aryl)(R$^9$), CONH—R$^9$, CON—(R$^9$)(R$^{10}$), SO$_3$H, SO$_2$-alkyl, SO$_2$-alkyl-R$^9$, SO$_2$-aryl, SO$_2$-aryl-R$^9$, SO$_2$NH$_2$, SO$_2$NH—R$^9$, SO$_2$N—(R$^9$)(R$^{10}$), CF$_3$, CO-alkyl, CO-alkyl-R$^9$, CO-aryl, CO-aryl-R$^9$ or R$^{11}$, wherein alkyl, aryl, aralkyl groups may be further substituted with one or more groups selected from halogeno, NO$_2$, OH, O-methyl, NH$_2$, COOH, CONH$_2$ and CF$_3$;

wherein at least one of $R^1$, $R^2$, $R^3$, $R^4$, $R^5$, $R^6$, $R^7$ and $R^8$ is an $R^9$ or $R^{10}$-containing group, or is $R^{11}$;

$R^9$ and $R^{10}$ are each independently solubilising groups selected from:
(i) a mono-, di- or polyhydroxylated alicyclic group;
  a di- or polyhydroxylated aliphatic or aromatic group;
  a carbohydrate derivative;
  an O- and/or S-containing heterocyclic group optionally substituted by one or more hydroxyl groups;
  an aliphatic or aromatic group containing a carboxamide, sulfoxide, sulfone, or sulfonamide function; or
  a halogenated alkylcarbonyl group;
(ii) COOH, SO$_3$H, OSO$_3$H, PO$_3$H$_2$, or OPO$_3$H$_2$;
(iii) Y, where Y is selected from an alicyclic, aromatic, or heterocyclic group comprising one or more of the functions =N—, —O—, —NH$_2$, —NH—, a quarternary amine salt, guanidine, and amidine, where Y is optionally substituted by one or more substituents selected from:
  SO$_2$-alkyl;
  alkyl optionally substituted by one or more OH groups;
  CO-alkyl;
  aralkyl;
  COO-alkyl; and
  an ether group optionally substituted by one or more OH groups; and where Y is other than pyridinyl;
(iv) a natural or unnatural amino acid, a peptide or a peptide derivative;

each $R^{11}$ is a solubilising group as defined for $R^9$ and $R^{10}$ in (i) or (iv) above; or is selected from:
(v) OSO$_3$H, PO$_3$H$_2$, or OPO$_3$H$_2$;
(vi) Y as defined above, but excluding guanidine and quarternary amine salts;
(vii) NHCO(CH$_2$)$_m$[NHCO(CH$_2$)$_{m'}$]$_p$[NHCO(CH$_2$)$_{m''}$]$_q$Y or NHCO(CH$_2$)$_t$NH(CH$_2$)$_{t'}$Y where p and q are each 0 or 1, and m, m', m", t and t' are each independently an integer from 1 to 10; and
(viii) (CH$_2$)$_n$NR$^{14}$COR$^{12}$, (CH$_2$)$_{n'}$NR$^{15}$SO$_2$R$^{13}$, or SO$_2$R$^{16}$, where $R^{12}$, $R^{13}$ and $R^{16}$ are each alkyl groups optionally comprising one or more heteroatoms, and which are optionally substituted by one or more substituents selected from OH, NH$_2$, halogen and NO$_2$, $R^{14}$ and $R^{15}$ are each independently H or alkyl, and n and n' are each independently 0, 1, 2, or 3;
(ix) an ether or polyether optionally substituted by one or more hydroxyl groups or one or more Y groups;
(x) (CH$_2$)$_r$ NH$_2$; where r is 0, 1, 2, or 3;

(xi) (CH$_2$)$_r$·OH; where r' is 0, 1, 2, or 3;

with the proviso that the compound is other than:
2-Chloro-N-{4-methyl-5-[2-(3-nitro-phenylamino)-pyrimidin-4-yl]-thiazol-2-yl}-acetamide;
N-{4-Methyl-5-[2-(3-nitro-phenylamino)-pyrimidin-4-yl]-thiazol-2-yl}-methane sulfonamide;
2-Chloro-N-{5-[2-(4-fluoro-phenylamino)-pyrimidin-4-yl]-4-methyl-thiazol-2-yl}-acetamide;
{3-[4-(2,4-Dimethyl-thiazol-5-yl)-pyrimidin-2-ylamino]-phenyl}-methanol;
2-{4-[4-(2-Amino-4-methyl-thiazol-5-yl)-pyrimidin-2-ylamino]-phenyl}-ethanol; or
2-{4-[4-(2,4-Dimethyl-thiazol-5-yl)-pyrimidin-2-ylamino]-phenyl}-ethanol.

A second aspect of the invention relates to a pharmaceutical composition comprising a compound of formula I as defined above admixed with a pharmaceutically acceptable diluent, excipient or carrier.

A third aspect of the invention relates to the use of a compound of formula I as defined above in the preparation of a medicament for treating a proliferative disorder.

A fourth aspect of the invention relates to the use of a compound of formula Ia, or a pharmaceutically acceptable salt thereof,

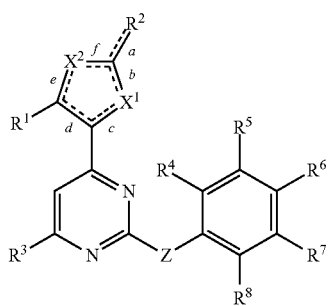

Ia wherein:
(A) one of X$^1$ and X$^2$ is S, and the other of X$^1$ and X$^2$ is N;
"a" is a single bond;
"b", "c", "d", "e" and "f" are single or double bonds so as to form a thiazolyl ring;
R$^2$ is independently as defined below for R$^1$, R$^{3-8}$; or
(B) one of X$^1$ and X$^2$ is S, and the other of X$^1$ and X$^2$ is NR$^{17}$;
"a" and "d" are each double bonds; and
"b", "c", "e" and "f" are each single bonds;
R$^2$ is oxo;
R$^{17}$ is H or alkyl;

where:
Z is NH, NHCO, NHSO$_2$, NHCH$_2$, CH$_2$, CH$_2$CH$_2$, CH═CH, SO$_2$, or SO;
R$^1$, R$^3$, R$^4$, R$^5$, R$^6$, R$^7$ and R$^8$ are each independently H, alkyl, alkyl-R$^9$, aryl, aryl-R$^9$, aralkyl, aralkyl-R$^9$, halogeno, NO$_2$, CN, OH, O-alkyl, COR$^9$, COOR$^9$, O-aryl, O—R$^9$, NH$_2$, NH-alkyl, NH-aryl, N-(alkyl)$_2$, N-(aryl)$_2$, N-(alkyl)(aryl), NH—R$^9$, N—(R$^9$)(R$^{10}$), N-(alkyl)(R$^9$), N-(aryl)(R$^9$), COOH, CONH$_2$, CONH-alkyl, CONH-aryl, CON-(alkyl)(R$^9$), CON(aryl)(R$^9$), CONH—R$^9$, CON—(R$^9$)(R$^{10}$), SO$_3$H, SO$_2$-alkyl, SO$_2$-alkyl-R$^9$, SO$_2$-aryl, SO$_2$-aryl-R$^9$, SO$_2$NH$_2$, SO$_2$NH—R$^9$, SO$_2$N—(R$^9$)(R$^{10}$), CF$_3$, CO-alkyl, CO-alkyl-R$^9$, CO-aryl, CO-aryl-R$^9$ or R$^{11}$, wherein alkyl, aryl, aralkyl groups may be further substituted with one or more groups selected from halogeno, NO$_2$, OH, O-methyl, NH$_2$, COOH, CONH$_2$ and CF$_3$;

wherein at least one of R$^1$, R$^2$, R$^3$, R$^4$, R$^5$, R$^6$, R$^7$ and R$^8$ is an R$^9$ or R$^{10}$-containing group, or is R$^{11}$;

R$^9$ and R$^{10}$ are each independently solubilising groups selected from:
(i) a mono-, di- or polyhydroxylated alicyclic group;
a di- or polyhydroxylated aliphatic or aromatic group;
a carbohydrate derivative;
an O- and/or S-containing heterocyclic group optionally substituted by one or more hydroxyl groups;
an aliphatic or aromatic group containing a carboxamide, sulfoxide, sulfone, or sulfonamide function; or
a halogenated alkylcarbonyl group;
(ii) COOH, SO$_3$H, OSO$_3$H, PO$_3$H$_2$, or OPO$_3$H$_2$;
(iii) Y, where Y is selected from an alicyclic, aromatic, or heterocyclic group comprising one or more of the functions ═N—, —O—, —NH$_2$, —NH—, a quarternary amine salt, guanidine, and amidine, where Y is optionally substituted by one or more substituents selected from:
SO$_2$-alkyl;
alkyl optionally substituted by one or more OH groups;
CO-alkyl;
aralkyl;
COO-alkyl; and
an ether group optionally substituted by one or more OH groups; and where Y is other than pyridinyl;
(iv) a natural or unnatural amino acid, a peptide or a peptide derivative;

each R$^{11}$ is a solubilising group as defined for R$^9$ and R$^{10}$ in (i) or (iv) above; or is selected from:
(v) OSO$_3$H, PO$_3$H$_2$, or OPO$_3$H$_2$;
(vi) Y as defined above, but excluding guanidine and quarternary amine salts;
(vii) NHCO(CH$_2$)$_m$[NHCO(CH$_2$)$_{m'}$]$_p$[NHCO(CH$_2$)$_{m''}$]$_q$Y or NHCO(CH$_2$)$_t$NH(CH$_2$)$_{t'}$Y where p and q are each 0 or 1, and m, m', m'', t and t' are each independently an integer from 1 to 10; and
(viii) (CH$_2$)$_n$NR$^{14}$COR$^{12}$, (CH$_2$)$_{n'}$NR$^{15}$SO$_2$R$^{13}$, or SO$_2$R$^{16}$, where R$^{12}$, R$^{13}$ and R$^{16}$ are each alkyl groups optionally comprising one or more heteroatoms, and which are optionally substituted by one or more substituents selected from OH, NH$_2$, halogen and NO$_2$, R$^{14}$ and R$^{15}$ are each independently H or alkyl, and n and n' are each independently 0, 1, 2, or 3;
(ix) an ether or polyether optionally substituted by one or more hydroxyl groups or one or more Y groups;
(x) (CH$_2$)$_r$NH$_2$; where r is 0, 1, 2, or 3;
(xi) (CH$_2$)$_r$·OH; where r' is 0, 1, 2, or 3;

in the preparation of a medicament for treating a viral disorder.

A fifth aspect of the invention relates to the use of a compound of formula I as defined above for inhibiting a protein kinase.

A sixth aspect of the invention relates to the use of a compound of formula I as defined above in an assay for identifying further candidate compounds capable of inhibiting a cyclin dependent kinase.

DETAILED DESCRIPTION

As used herein the term "alkyl" includes both straight chain and branched alkyl groups having from 1 to 8 carbon atoms, e.g. methyl, ethyl propyl, isopropyl, butyl, isobutyl, tert-butyl, pentyl, hexyl etc. and the term "lower alkyl" is similarly used for groups having from 1 to 4 carbon atoms.

As used herein, the term "aryl" refers to a substituted (mono- or poly-) or unsubstituted monoaromatic or polyaromatic system, wherein said polyaromatic system may be fused or unfused. Preferably, the term "aryl" is includes groups having from 6 to 10 carbon atoms, e.g. phenyl, naphthyl etc. The term "aryl" is synonymous with the term "aromatic".

The term "aralkyl" is used as a conjunction of the terms alkyl and aryl as given above.

The term "alicyclic" refers to a cyclic aliphatic group.

The term "aliphatic" takes its normal meaning in the art and includes non-aromatic groups such as alkanes, alkenes and alkynes and substituted derivatives thereof.

As used herein, the term "carbohydrate derivative" refers to a compound of general formula $C_x(H_2O)_y$, or a derivative thereof. Preferably, the carbohydrate is a a mono-, di- or tri-saccharide. Monosaccharides can exist as either straight chain or ring-shaped molecules and are classified according to the number of carbon atoms they possess; trioses have three carbons, tetroses four, pentoses five and hexoses six. Each of these subgroups may be further divided into aldoses and ketoses, depending on whether the molecule contains an aldehyde group (—CHO) or a ketone group (C=O). Typical examples of monosaccharides include glucose, fructose, and galactose. Disaccharides consist of two linked monosaccharide molecules, and include for example, maltose and lactose. Trisaccharides consist of three linked monosaccharide molecules.

The term "derivative" as used herein includes chemical modification of an entity. Illustrative of such chemical modifications would be replacement of hydrogen by a halo group, an alkyl group, an acyl group or an amino group.

The term "heterocycle" refers to a saturated or unsaturated cyclic group containing one or more heteroatoms in the ring.

As used herein the phrase "preparation of a medicament" includes the use of a compound of formula I directly as the medicament in addition to its use in a screening programme for further anti-viral agents or in any stage of the manufacture of such a medicament.

In one preferred embodiment, the invention relates to compounds of formula Ib, or pharmaceutically acceptable salts thereof,

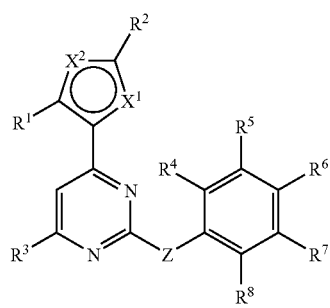

Ib wherein one of $X^1$ and $X^2$ is S, and the other of $X^1$ and $X^2$ is N, and Z, $R^{1-8}$ are as defined above.

In another preferred embodiment, the invention relates to compounds of formula Ic, or pharmaceutically acceptable salts thereof,

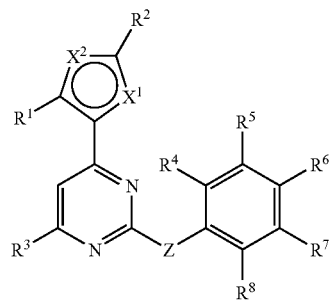

Ic wherein
one of $X^1$ and $X^2$ is S, and the other of $X^1$ and $X^2$ is N;
Z is NH, NHCO, NHSO$_2$, NHCH$_2$, CH$_2$, CH$_2$CH$_2$, CH=CH, SO$_2$, or SO;
$R^1$, $R^2$, $R^3$, $R^4$, $R^5$, $R^6$, $R^7$ and $R^8$ are each independently H, alkyl, alkyl-R$^9$, aryl, aryl-R$^9$, aralkyl, aralkyl-R$^9$, halogeno, NO$_2$, CN, OH, O-alkyl, COR$^9$, COOR$^9$, O-aryl, O—R$^9$, NH$_2$, NH-alkyl, NH-aryl, N-(alkyl)$_2$, N-(aryl)$_2$, N-(alkyl)(aryl), NH—R$^9$, N—(R$^9$)(R$^{10}$), N-(alkyl)(R$^9$), N-(aryl)(R$^9$), COOH, CONH$_2$, CONH-alkyl, CONH-aryl, CON-(alkyl)(R$^9$), CON(aryl)(R$^9$), CONH—R$^9$, CON—(R$^9$)(R$^{10}$), SO$_3$H, SO$_2$-alkyl, SO$_2$-alkyl-R$^9$, SO$_2$-aryl, SO$_2$-aryl-R$^9$, SO$_2$NH$_2$, SO$_2$NH—R$^9$, SO$_2$N—(R$^9$)(R$^{10}$), CF$_3$, CO-alkyl, CO-alkyl-R$^9$, CO-aryl, CO-aryl-R$^9$ or R$^{11}$, wherein alkyl, aryl, aralkyl groups may be further substituted with one or more groups selected from halogeno, NO$_2$, OH, O-methyl, NH$_2$, COOH, CONH$_2$ and CF$_3$;

wherein at least one of $R^1$, $R^2$, $R^3$, $R^4$, $R^5$, $R^6$, $R^7$ and $R^8$ is an $R^9$ or $R^{10}$-containing group, or is $R^{11}$;

$R^9$ and $R^{10}$ are each independently solubilising groups selected from:
(i) a mono-, di- or polyhydroxylated alicyclic group;
  a di- or polyhydroxylated aliphatic or aromatic group;
  a carbohydrate derivative;
  an O- and/or S-containing heterocyclic group optionally substituted by one or more hydroxyl groups;
  an aliphatic or aromatic group containing a carboxamide, sulfoxide, sulfone, or sulfonamide function; or
  a halogenated alkylcarbonyl group;
(ii) COOH, SO$_3$H, OSO$_3$H, PO$_3$H$_2$, or OPO$_3$H$_2$;
(iii) Y, where Y is selected from an alicyclic, aromatic, or heterocyclic group comprising one or more of the functions =N—, —O—, —NH$_2$, —NH—, a quarternary amine salt, guanidine, and amidine, where Y is optionally substituted by one or more substituents selected from:
  SO$_2$-alkyl;
  alkyl optionally substituted by one or more OH groups;
  CO-alkyl;
  aralkyl;
  COO-alkyl; and
  an ether group optionally substituted by one or more OH groups; and where Y is other than pyridinyl;
(iv) a natural or unnatural amino acid, a peptide or a peptide derivative;

$R^{11}$ is a solubilising group as defined for $R^9$ and $R^{10}$ in (i) or (iv) above; or is selected from:
(v) OSO$_3$H, PO$_3$H$_2$, or OPO$_3$H$_2$;
(vi) Y as defined above, but excluding guanidine and quarternary amine salts;

(vii) NHCO(CH$_2$)$_m$[NHCO(CH$_2$)$_{m'}$]$_p$[NHCO(CH$_2$)$_{m''}$]$_q$Y where p and q are each 0 or 1, and m, m' and m'' are each an integer from 1 to 10; and (viii) NHCOR$^{12}$ or NHSO$_2$R$^{13}$, where R$^{12}$ and R$^{13}$ are each alkyl groups optionally comprising one or more heteroatoms, and which are substituted by one or more substituents selected from OH, NH$_2$, halogen and NO$_2$;

(ix) an ether or polyether optionally substituted by one or more hydroxyl groups;

with the proviso that the compound is other than:
N-{4-Methyl-5-[2-(3-nitro-phenylamino)-pyrimidin-4-yl]-thiazol-2-yl}-methanesulfonamide;
2-Chloro-N-{4-methyl-5-[2-(3-nitro-phenylamino)-pyrimidin-4-yl]-thiazol-2-yl}-acetamide; or
2-Chloro-N-{5-[2-(4-fluoro-phenylamino)-pyrimidin-4-yl]-4-methyl-thiazol-2-yl}-acetamide.

Preferably, the compounds of formula I bear a mono- or di-substituted thiazol-3-yl or thiazol-5-yl radical attached to the pyrimidine ring through one of the ring carbon atoms Most preferably, the heterocycle is a thiazol-5-yl group.

Thus, in one preferred embodiment of the invention, X$^1$ is S and X$^2$ is N.

The following preferred features apply to compounds of formula I, Ia, Ib and Ic.

In another preferred embodiment, Z is NH.

In another preferred embodiment, R$^3$ is H.

In yet another preferred embodiment, at least one of R$^2$, R$^5$, R$^6$ or R$^7$ is an R$^9$ or R$^{10}$-containing group, or is R$^{11}$.

In one particularly preferred embodiment, X$^1$ is S, X$^2$ is N, Z is NH, R$^1$ is Me, R$^2$ is alkyl or amino, R$^3$ is H, one or two of R$^5$, R$^6$, and R$^7$ are CF$_3$, OH, O-alkyl, halogeno, NO$_2$, NH$_2$, NH-alkyl or N-(alkyl)$_2$ and at least one of R$^2$, R$^5$, R$^6$ or R$^7$ is an R$^9$ or R$^{10}$ containing group, or is R$^{11}$.

In another preferred embodiment, at least one of R$^1$, R$^2$, R$^3$, R$^4$, R$^5$, R$^6$, R$^7$ and R$^8$ is R$^{11}$.

In one preferred embodiment, R$^{11}$ is a solubilising group as defined for R$^9$ and R$^{10}$ in (i)-(iv) above, or (v)-(x) as defined above.

In another preferred embodiment, R$^{11}$ is a solubilising group as defined for R$^9$ and R$^{10}$ in (i)-(iv) above, or (v)-(vii), (ix)-(x) as defined above, or is selected from:
(CH$_2$)$_n$NR$^{14}$COR$^{12}$, where R$^{12}$ is an alkyl group optionally comprising one or more heteroatoms, and which is optionally substituted by one or more substituents selected from OH, NH$_2$ and NO$_2$,
(CH$_2$)$_n$NR$^{15}$SO$_2$R$^{13}$, where R$^{13}$ is an alkyl group optionally comprising one or more heteroatoms, and which is substituted by one or more substituents selected from OH, NH$_2$, halogen and NO$_2$,
SO$_2$R$^{16}$, where R$^{16}$ is an alkyl group optionally comprising one or more heteroatoms, and which is optionally substituted by one or more substituents selected from OH, NH$_2$, halogen and NO$_2$; and
R$^{14}$ and R$^{15}$ are each independently H or alkyl, and n and n' are each independently 0, 1, 2, or 3.

Preferably, the solubilising group is R$^{11}$ and is:
(a) Y as defined in above, but excluding guanidine, where Y can also be an alicyclic, aromatic, or heterocyclic group comprising one or more =N— groups;
(b) NHCO(CH$_2$)$_m$[NHCO(CH$_2$)$_{m'}$]$_p$[NHCO(CH$_2$)$_{m''}$]$_q$Y or NHCO(CH$_2$)$_t$NH(CH$_2$)$_{t'}$Y where p and q are each 0 or 1, and m, m', m'', t and t' are each an integer from 1 to 10; or
(c) (CH$_2$)$_n$NR$^4$COR$^{12}$, (CH$_2$)$_n$NR$^{15}$SO$_2$R$^{13}$, or SO$_2$R$^{16}$, where R$^{12}$, R$^{13}$ and R$^{16}$ are each alkyl groups optionally comprising one or more heteroatoms, and which are substituted by one or more substituents selected from OH, NH$_2$, halogen and NO$_2$, R$^{14}$ and R$^{15}$ are each independently H or alkyl, and n and n' are each independently 0, 1, 2, or 3.

Preferably, the solubilising group is R$^{11}$, and R$^{11}$ is:
(a) Y as defined above, but excluding guanidine, where Y can also be an alicyclic, aromatic, or heterocyclic group comprising one or more =N— groups;
(b) NHCO(CH$_2$)$_m$[NHCO(CH$_2$)$_{m'}$]$_p$[NHCO(CH$_2$)$_{m''}$]$_q$Y where p and q are each 0 or 1, and m, m' and m'' are each integers from 1 to 10
(c) NHCOR$^{12}$ or NHSO$_2$R$^{13}$, where R$^{12}$ and R$^{13}$ are each alkyl groups optionally comprising one or more heteroatoms, and which are optionally substituted by one or more substituents selected from OH, NH$_2$, halogen and NO$_2$.

Even more preferably, Y is an alicyclic group comprising one or more of the functions —O—, NH$_2$, —NH—, =N—, a quarternary amine salt, or amidine, and wherein Y is optionally substituted by one or more substituents as defined above.

More preferably still, Y is a morpholine or piperazine group, each of which may be optionally substituted by one or more substituents selected from SO$_2$-alkyl, alkyl optionally substituted by one or more OH groups, CO-alkyl, aralkyl, COO-alkyl, and an ether group optionally substituted by one or more OH groups In one especially preferred embodiment of the invention, Y is a 2-oxo-hexahydro-thien[3,4-d]imidazole group.

In one preferred embodiment, at least one of R$^2$, R$^6$ or R$^7$ is R$^{11}$.

For this embodiment, preferably R$^{11}$ is selected from the following:

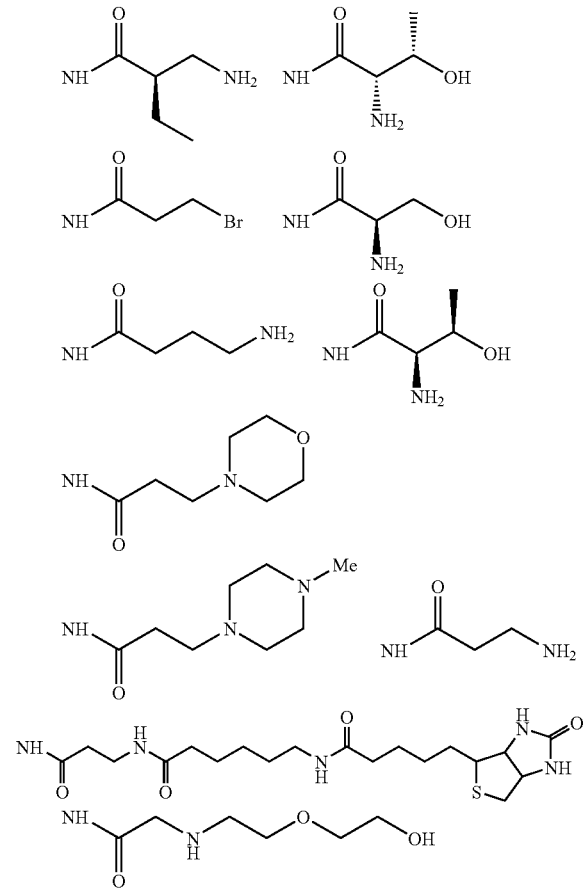

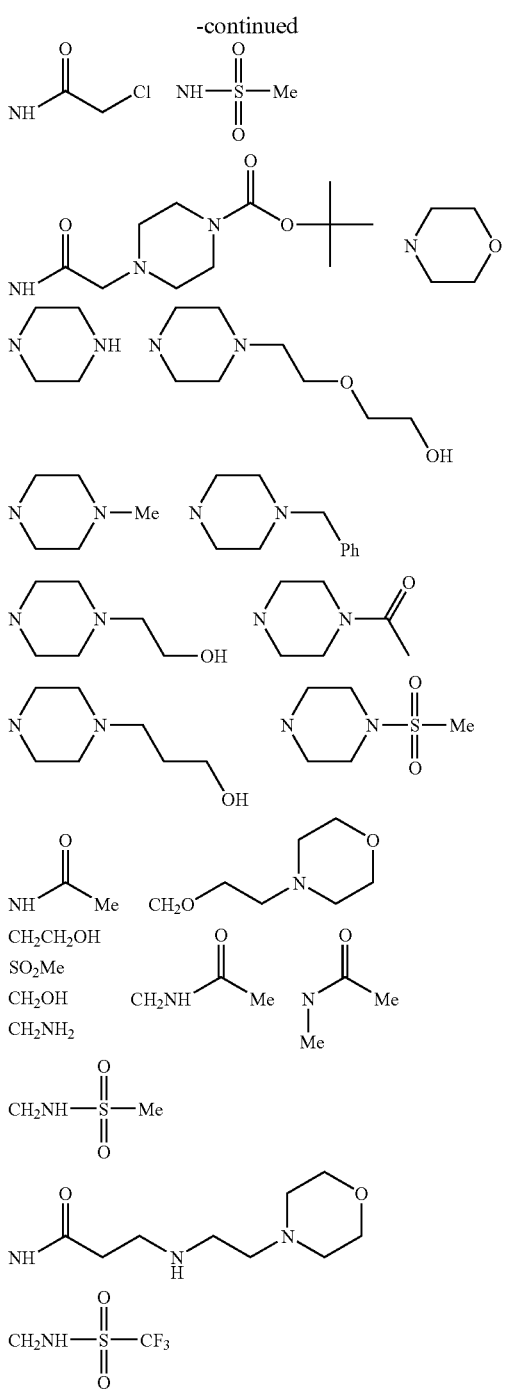

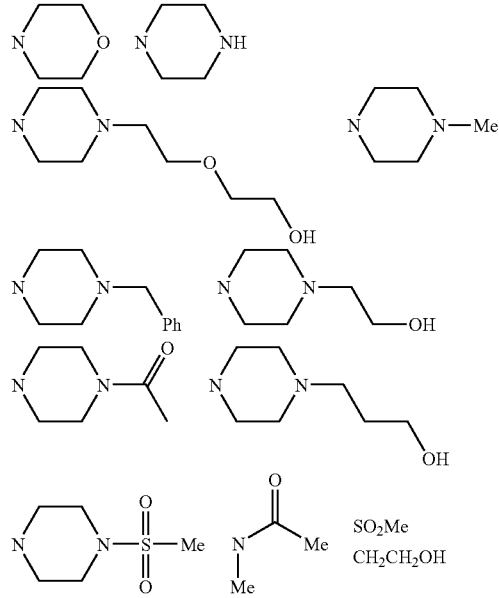

In another preferred embodiment, $R^7$ is $R^{11}$ and $R^4$, $R^5$, $R^6$, $R^8$ are all H, and $R^2$ is selected from alkyl, O-alkyl, $NH_2$ and NH-alkyl. Preferably, for this embodiment, $R^{11}$ is selected from:

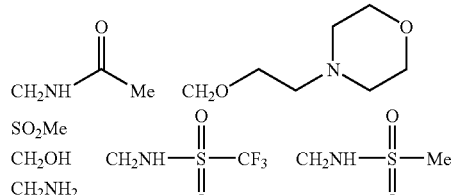

In another preferred embodiment of the invention, at least one of $R^2$ or $R^6$ is $R^{11}$.

For this embodiment, $R^{11}$ is preferably selected from the following:

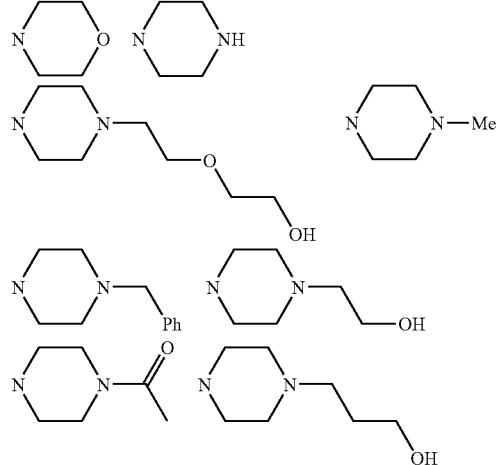

In one especially preferred embodiment, $R^6$ or $R^7$ is $R^{11}$. More preferably, $R^6$ is $R^{11}$ and $R^2$, $R^4$, $R^5$, $R^7$ and $R^8$ are each independently selected from alkyl, H, $CF_3$, OH, O-alkyl, halogeno, $NO_2$, $NH_2$, NH-alkyl and N-(alkyl)$_2$. More preferably still, $R^6$ is $R^{11}$ and $R^2$, $R^4$, $R^5$, $R^7$ and $R^8$ are each independently selected from alkyl, H, O-alkyl, halogeno, $NO_2$, $NH_2$ and NH-alkyl. Even more preferably, $R^6$ is $R^{11}$ and $R^4$, $R^5$, $R^7$ and $R^8$ are all H and $R^2$ is selected from alkyl, O-alkyl, $NH_2$ and NH-alkyl.

Even more preferably still, for this embodiment, $R^{11}$ is selected from:

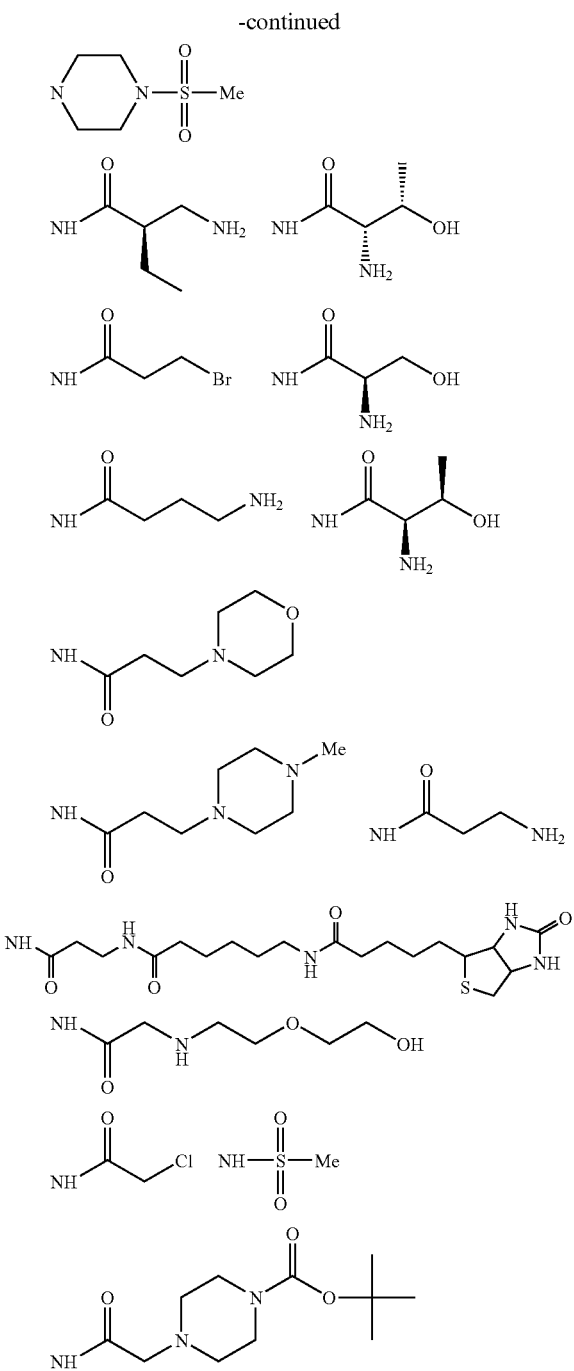

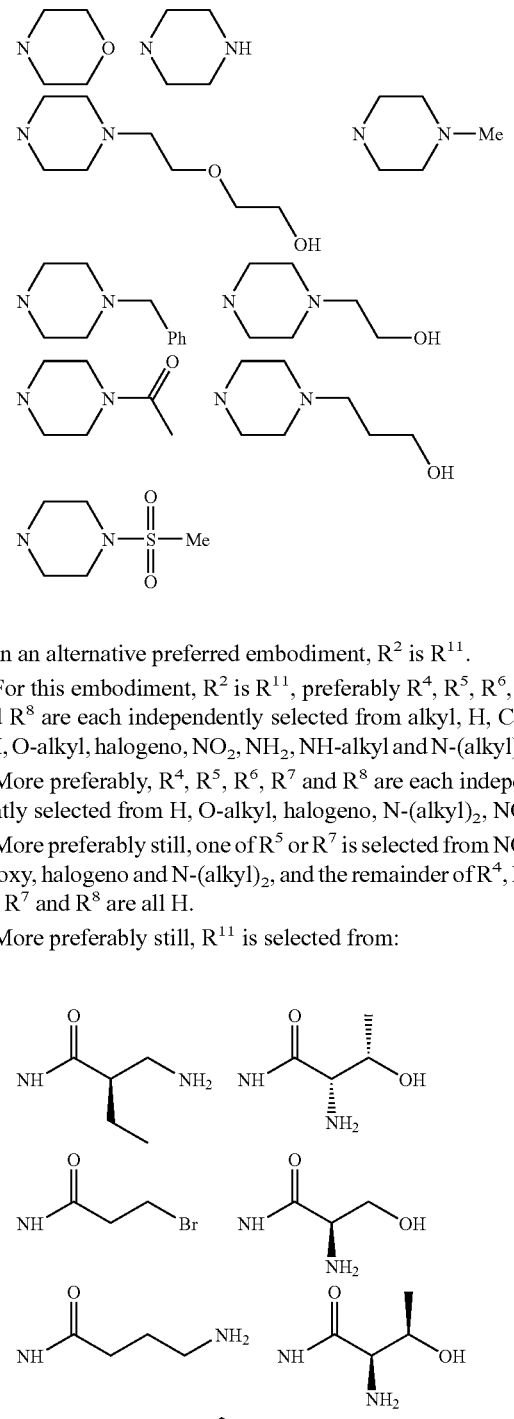

In an alternative preferred embodiment, $R^2$ is $R^{11}$.

For this embodiment, $R^2$ is $R^{11}$, preferably $R^4$, $R^5$, $R^6$, $R^7$ and $R^8$ are each independently selected from alkyl, H, $CF_3$, OH, O-alkyl, halogeno, $NO_2$, $NH_2$, NH-alkyl and N-(alkyl)$-_2$.

More preferably, $R^4$, $R^5$, $R^6$, $R^7$ and $R^8$ are each independently selected from H, O-alkyl, halogeno, N-(alkyl)$_2$, $NO_2$.

More preferably still, one of $R^5$ or $R^7$ is selected from $NO_2$, alkoxy, halogeno and N-(alkyl)$_2$, and the remainder of $R^4$, $R^5$, $R^6$, $R^7$ and $R^8$ are all H.

More preferably still, $R^{11}$ is selected from:

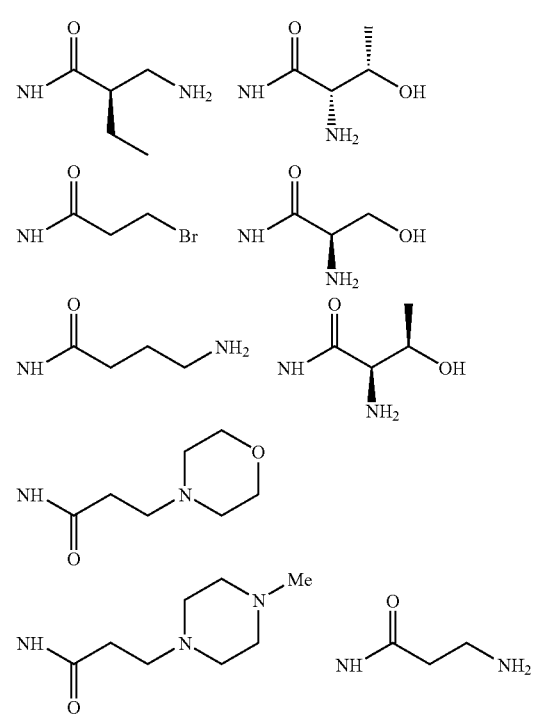

In one especially preferred embodiment, $R^6$ is $R^{11}$.

For this embodiment, where $R^6$ is $R^{11}$, preferably $R^2$, $R^4$, $R^5$, $R^7$ and $R^8$ are each independently selected from alkyl, H, $CF_3$, OH, O-alkyl, halogeno, $NO_2$, $NH_2$, NH-alkyl and N-(alkyl)$_2$.

Even more preferably, $R^2$, $R^4$, $R^5$, $R^7$ and $R^8$ are each independently selected from alkyl, H, O-alkyl, halogeno, $NO_2$, $NH_2$ and NH-alkyl.

More preferably still, $R^4$, $R^5$, $R^7$ and $R^8$ are all H and $R^2$ is selected from alkyl, O-alkyl, $NH_2$ and NH-alkyl.

More preferably still, $R^{11}$ is selected from:

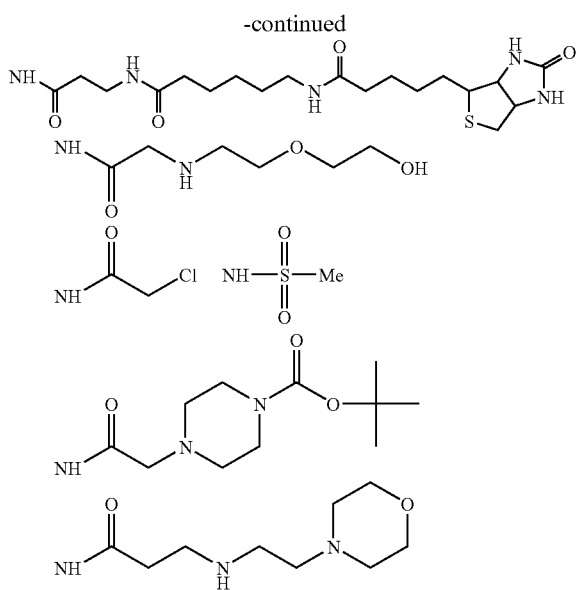

In one preferred embodiment of the invention, $R^1$ is methyl, Z is NH and $R^3$ is H.

In another embodiment, the compound of the invention is of formula Id, or or a pharmaceutically acceptable salt thereof,

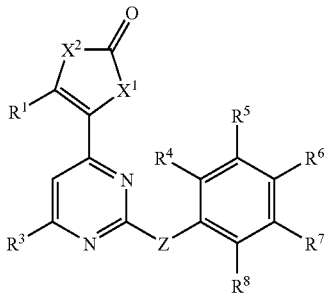

Id

Preferably, $R^1$ and $R^{3-8}$ are as defined above for compounds of formula I, Ia, Ib and Ic. Preferably, $R^{17}$ is alkyl, more preferably methyl.

In a preferred embodiment of the invention, the compound of formula I is selected from those listed in Table 1, but excluding compounds [24], [32] and [33].

In one especially preferred embodiment, the compound of formula I is selected from the following:

[4-(2-Methoxy-4-methyl-thiazol-5-yl)-pyrimidin-2-yl]-(4-morpholin-4-yl-phenyl)-amine;

[4-(2-Amino-4-methyl-thiazol-5-yl)-pyrimidin-2-yl]-(4-morpholin-4-yl-phenyl)-amine;

[4-(2,4-Dimethyl-thiazol-5-yl)-pyrimidin-2-yl]-(4-morpholin-4-yl-phenyl)-amine;

[4-(2-N-Methylamino-4-methyl-thiazol-5-yl)-pyrimidin-2-yl]-(4-morpholinophenyl)-amine;

[4-(2-Ethylamino-4-methyl-thiazol-5-yl)-pyrimidin-2-yl]-(4-morpholin-4-yl-phenyl)-amine;

1-(4-{4-[4-(2,4-Dimethyl-thiazol-5-yl)-pyrimidin-2-ylamino]-phenyl}-piperazin-1-yl)-ethanone;

[4-(2,4-Dimethyl-thiazol-5-yl)-pyrimidin-2-yl]-(4-piperazin-1-yl-phenyl)-amine;

[4-(2,4-Dimethyl-thiazol-5-yl)-pyrimidin-2-yl]-[4-(4'-2"-ethoxylethanolpiperazino)-phenyl]-amine;

3-(4-{4-[4-(2,4-Dimethyl-thiazol-5-yl)-pyrimidin-2-ylamino]-phenyl}-piperazin-1-yl)-propan-1-ol;

2-(4-{4-[4-(2,4-Dimethyl-thiazol-5-yl)-pyrimidin-2-ylamino]-phenyl}-piperazin-1-yl)-ethanol;

[4-(2,4-Dimethyl-thiazol-5-yl)-pyrimidin-2-yl]-[4-(4-methanesulfonyl-piperazin-1-yl)-phenyl]-amine;

[4-(4-Benzyl-piperazin-1-yl)-phenyl]-[4-(4-methyl-2-methylamino-thiazol-5-yl)-pyrimidin-2-yl]-amine;

[4-(2,4-Dimethyl-thiazol-5-yl)-pyrimidin-2-yl]-[4-(4-methyl-piperazin-1-yl)-phenyl]-amine;

[4-(2-Methoxy-4-methyl-thiazol-5-yl)-pyrimidin-2-yl]-[4-(4-methyl-piperazin-1-yl)-phenyl]-amine;

3-Amino-N-{4-methyl-5-[2-(3-nitro-phenylamino)-pyrimidin-4-yl]-thiazol-2-yl}-propionamide;

(2S)-2-Amino-3-hydroxy-N-{4-methyl-5-[2-(3-nitro-phenylamino)-pyrimidin-4-yl]-thiazol-2-yl}-propionamide;

(2R,3R)-2-Amino-3-hydroxy-N-{4-methyl-5-[2-(3-nitro-phenylamino)-pyrimidin-4-yl]-thiazol-2-yl}-butyramide;

(2R)-2-Amino-N-{4-methyl-5-[2-(3-nitro-phenylamino)-pyrimidin-4-yl]-thiazol-2-yl}-butyramide;

(2S,3S)-2-Amino-3-hydroxy-N-{4-methyl-5-[2-(3-nitro-phenylamino)-pyrimidin-4-yl]-thiazol-2-yl}-butyramide;

4-Amino-N-{4-methyl-5-[2-(3-nitro-phenylamino)-pyrimidin-4-yl]-thiazol-2-yl}-butyramide;

3-Amino-N-{4-methyl-5-[2-(4-morpholin-4-yl-phenylamino)-pyrimidin-4-yl]-thiazol-2-yl}-propionamide;

3-Bromo-N-{5-[2-(4-fluoro-phenylamino)-pyrimidin-4-yl]-4-methyl-thiazol-2-yl}-propionamide;

N-{5-[2-(4-Fluoro-phenylamino)-pyrimidin-4-yl]-4-methyl-thiazol-2-yl}-3-morpholin-4-yl-propionamide;

N-{4-Methyl-5-[2-(3-nitro-phenylamino)-pyrimidin-4-yl]-thiazol-2-yl}-3-morpholin-4-yl-propionamide;

N-{4-Methyl-5-[2-(3-nitro-phenylamino)-pyrimidin-4-yl]-thiazol-2-yl}-3-(4-methyl-piperazin-1-yl)-propionamide;

2-Chloro-N-{5-[2-(3-chloro-phenylamino)-pyrimidin-4-yl]-4-methyl-thiazol-2-yl}-acetamide;

2-Chloro-N-{5-[2-(3-methoxy-phenylamino)-pyrimidin-4-yl]-4-methyl-thiazol-2-yl}-acetamide;

2-Chloro-N-{5-[2-(4-dimethylamino-phenylamino)-pyrimidin-4-yl]-4-methyl-thiazol-2-yl}-acetamide;

4-({4-Methyl-5-[2-(3-nitro-phenylamino)-pyrimidin-4-yl]-thiazol-2-ylcarbamoyl}-methyl)-piperazine-1-carboxylic acid tert-butyl ester;

N-{5-[2-(4-Dimethylamino-phenylamino)-pyrimidin-4-yl]-4-methyl-thiazol-2-yl}-2-[2-(2-hydroxy-ethoxy)-ethylamino]-acetamide;

6-[5-(2-Oxo-hexahydro-thieno[3,4-d]imidazol-4-yl)-pentanoylamino]-hexanoic acid (2-{4-methyl-5-[2-(4-morpholin-4-yl-phenylamino)-pyrimidin-4-yl]-thiazol-2-ylcarbamoyl}-ethyl)-amide;

N-{5-[2-(4-Fluoro-phenylamino)-pyrimidin-4-yl]-4-methyl-thiazol-2-yl}-methanesulfonamide;

3-Bromo-N-{4-methyl-5-[2-(3-nitro-phenylamino)-pyrimidin-4-yl]-thiazol-2-yl}-propionamide;

3-(1-{4-[4-(2,4-Dimethyl-thiazol-5-yl)-pyrimidin-2-ylamino]-phenyl}-piperidin-4-yl)-propan-1-ol;

2-Amino-3-hydroxy-N-{4-methyl-5-[2-(3-nitro-phenylamino)-pyrimidin-4-yl]-thiazol-2-yl}-butyramide; and 2-Chloro-N-{5-[2-(4-chloro-phenylamino)-pyrimidin-4-yl]-4-methyl-thiazol-2-yl}-acetamide.

In a further preferred embodiment of the invention, said compound of formula I is selected from the following:

[4-(2-Amino-4-methyl-thiazol-5-yl)-pyrimidin-2-yl]-(4-morpholin-4-yl-phenyl)-amine;

[4-(2,4-dimethyl-thiazol-5-yl)-pyrimidin-2-yl]-(4-morpholin-4-yl-phenyl)-amine;

[4-(2-N-methylamino-4-methyl-thiazol-5-yl)-pyrimidin-2-yl]-(4-morpholinophenyl)-amine;

(2R,3R)-2-amino-3-hydroxy-N-{4-methyl-5-[2-(3-nitro-phenylamino)-pyrimidin-4-yl]-thiazol-2-yl}-butyramide;

(2R)-2-amino-N-{4-methyl-5-[2-(3-nitro-phenylamino)-pyrimidin-4-yl]-thiazol-2-yl}-butyramide; and N-{4-methyl-5-[2-(3-nitro-phenylamino)-pyrimidin-4-yl]-thiazol-2-yl}-3-morpholin-4-yl-propionamide.

In one preferred embodiment the compound of formula I is capable of exhibiting an antiproliferative effect in human cell lines, as measured by a standard 72 h MTT cytotoxicity assay. Preferably, the compound of formula I exhibits an $IC_{50}$ value of less than 10 µM, more preferably less than 5 µM, even more preferably less than 1 µM as measured by said MTT assay. More preferably, the compound of formula I is selected from the following: [4], [8], [12], [14], [16], [22], [24], [25], [29], [32], [33], [39], [40], [50], [53], [61], [57], [62], [63], [64], [65] and [77]. More preferably still, the compound exhibits an $IC_{50}$ value of less than 0.5 less µM, more preferably still less than 0.2 µM. Even more preferably, the compound is selected from the following: [24], [25], [32], [33], [50], [62] and [64].

In another preferred embodiment, the compound of formula I is selected from [1], [11], [15] and [16].

In another preferred embodiment, the compound of formula I is capable of inhibiting one or more protein kinases, as measured by the assays described in the accompanying Examples section. Preferably, the compound of formula I exhibits an $IC_{50}$ value of less than 10 µM, more preferably less than 5 µM, even more preferably less than 1 µM or less than 0.5 less µM, more preferably still less than 0.1 µM. More preferably, the compound of formula I is selected from the following: [11], [13], [14], [15], [20], [21], [22], [24], [25], [32], [50], [53], [54], [55], [56], [57], [59], [61], [62], [64], [68], [71], [82], [83], [84] and [85]. More preferably still, the compound exhibits an $IC_{50}$ value of less than 0.01 µM. Even more preferably, the compound is selected from the following: [11], [22], [24], [32], [50], [62], [71] and [85].

In yet another preferred embodiment, the compound of formula I is selected from [1], [3], [11], [15] and [16].

The present invention provides a series of compounds equipped with solubilising functions on the phenyl and/or heteroaryl rings of the 2-phenylamino-4-heteroaryl-pyrimidine system. Modification with solubilising moieties has preserved the desired in vitro biological activity (inhibition of CDKs and cytotoxicity against transformed human cells) and in some cases has led to surprising and unexpected increases in potency. Furthermore, in vivo absorption, and oral bio-availability in particular can also be improved using the solubilising strategies presented herein.

Therapeutic Use

The compounds of formula I have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines AGS, H1299 or SJSA-1, or by showing inhibition of the interaction between HDM2 and p53 in an appropriate assay. These assays, including methods for their performance, are described in more detail in the accompanying Examples. Using such assays it may be determined whether a compound is anti-proliferative in the context of the present invention.

On preferred embodiment of the present invention therefore relates to the use of one or more compounds of formula I in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment of the invention, the compound of formula I or Ia is administered in an amount sufficient to inhibit at least one CDK enzyme.

In a more preferred embodiment of the invention, the compound of formula Ia is preferably administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

As defined herein, an anti-viral effect within the scope of the present invention may be demonstrated by the ability to inhibit CDK2, CDK7, CDK8 or CDK9. Assays for determining CDK activity are described in more detail in the accompanying examples.

Using such enzymes assays it may be determined whether a compound is anti-viral in the context of the present invention.

In a particularly preferred embodiment, the compounds of formula Ia are useful in the treatment of viral disorders, such as human cytomegalovirus (HCMV), herpes simplex virus type 1 (HSV-1), human immunodeficiency virus type 1 (HIV-1), and varicella zoster virus (VZV).

In a particularly preferred embodiment, the invention relates to the use of one or more compounds of formula Ia in the treatment of a viral disorder which is CDK dependent or sensitive. CDK dependent disorders are associated with an above normal level of activity of one or more CDK enzymes.

Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

One preferred embodiment of the invention relates to the use of a compound of formula Ie, or a pharmaceutically acceptable salt thereof, Ie

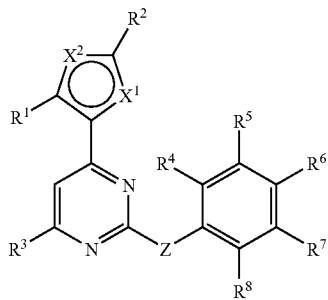

wherein
one of $X^1$ and $X^2$ is S, and the other of $X^1$ and $X^2$ is N;
Z is NH, NHCO, NHSO$_2$, NHCH$_2$, CH$_2$, CH$_2$CH$_2$, CH=CH, SO$_2$, or SO;
$R^1$, $R^2$, $R^3$, $R^4$, $R^5$, $R^6$, $R^7$ and $R^8$ are each independently H, alkyl, alkyl-$R^9$, aryl, aryl-$R^9$, aralkyl, aralkyl-$R^9$, halogeno, NO$_2$, CN, OH, O-alkyl, COR$^9$, COOR$^9$, O-aryl, O—$R^9$, NH$_2$, NH-alkyl, NH-aryl, N-(alkyl)$_2$, N-(aryl)$_2$, N-(alkyl)(aryl), NH—$R^9$, N—($R^9$)($R^{10}$), N-(alkyl)($R^9$), N-(aryl)($R^9$), COOH, CONH$_2$, CONH-alkyl, CONH-aryl, CON-(alkyl)($R^9$), CON(aryl)($R^9$), CONH—$R^9$, CON—($R^9$)($R^{10}$), SO$_3$H, SO$_2$-alkyl, SO$_2$-alkyl-$R^9$, SO$_2$-aryl, SO$_2$-aryl-$R^9$, SO$_2$NH$_2$, SO$_2$NH—$R^9$, SO$_2$N—($R^9$)($R^{10}$), CF$_3$, CO-alkyl, CO-alkyl-$R^9$, CO-aryl, CO-aryl-$R^9$ or $R^{11}$, wherein alkyl, aryl, aralkyl groups may be further substituted with one or more groups selected from halogeno, NO$_2$, OH, O-methyl, NH$_2$, COOH, CONH$_2$ and CF$_3$;

wherein at least one of $R^1$, $R^2$, $R^3$, $R^4$, $R^5$, $R^6$, $R^7$ and $R^8$ is an $R^9$ or $R^{10}$-containing group, or is $R^{11}$;

$R^9$ and $R^{10}$ are each independently solubilising groups selected from:
(i) a mono-, di- or polyhydroxylated alicyclic group;
   a di- or polyhydroxylated aliphatic or aromatic group;
   a carbohydrate derivative;
   an O- and/or S-containing heterocyclic group optionally substituted by one or more hydroxyl groups;
   an aliphatic or aromatic group containing a carboxamide, sulfoxide, sulfone, or sulfonamide function; or
   a halogenated alkylcarbonyl group;
(ii) COOH, SO$_3$H, OSO$_3$H, PO$_3$H$_2$, or OPO$_3$H$_2$;
(iii) Y, where Y is selected from an alicyclic, aromatic, or heterocyclic group comprising one or more of the functions =N—, —O—, —NH$_2$, —NH—, a quarternary amine salt, guanidine, and amidine, where Y is optionally substituted by one or more substituents selected from:
SO$_2$-alkyl;
alkyl optionally substituted by one or more OH groups;
CO-alkyl;
aralkyl;
COO-alkyl; and
an ether group optionally substituted by one or more OH groups; and
where Y is other than pyridinyl;
(iv) a natural or unnatural amino acid, a peptide or a peptide derivative;
$R^{11}$ is a solubilising group as defined for $R^9$ and $R^{10}$ in (i) or (iv) above; or is selected from:
(v) OSO$_3$H, PO$_3$H$_2$, or OPO$_3$H$_2$;
(vi) Y as defined above, but excluding guanidine and quarternary amine salts;
(vii) NHCO(CH$_2$)$_m$[NHCO(CH$_2$)$_{m'}$]$_p$[NHCO(CH$_2$)$_{m''}$]$_q$Y where p and q are each 0 or 1, and m, m' and m'' are each an integer from 1 to 10; and
(viii) NHCOR$^{12}$ or NHSO$_2$R$^{13}$, where $R^{12}$ and $R^{13}$ are each alkyl groups optionally comprising one or more heteroatoms, and which are substituted by one or more substituents selected from OH, NH$_2$, halogen and NO$_2$;
(ix) an ether or polyether optionally substituted by one or more hydroxyl groups;

in the preparation of a medicament for treating a viral disorder.

Preferred features are as defined above for compounds of formula I, Ia, Ib and Ic.

In a preferred embodiment, the compound of formula Ia is selected from those listed in Table 1.

More preferably, said compound of formula Ia is selected from the following: [1], [3], [4], [15] and [53].

For use in the treatment of viral disorders, preferably the compound of formula Ia is capable of inhibiting CK2, CDK7 and/or CDK9 and is selected from the following:
[4-(2-Ethylamino-4-methyl-thiazol-5-yl)-pyrimidin-2-yl]-(4-morpholin-4-yl-phenyl)-amine;
2-Amino-3-hydroxy-N-{4-methyl-5-[2-(3-nitro-phenylamino)-pyrimidin-4-yl]-thiazol-2-yl}-butyramide;
2-Amino-N-{4-methyl-5-[2-(3-nitro-phenylamino)-pyrimidin-4-yl]-thiazol-2-yl}-butyramide;
[4-(2-Amino-4-methyl-thiazol-5-yl)-pyrimidin-2-yl]-(4-morpholin-4-yl-phenyl)-amine;
[4-(4-Methyl-2-methylamino-thiazol-5-yl)-pyrimidin-2-yl]-(4-morpholin-4-yl-phenyl)-amine;
3-(1-{4-[4-(2,4-Dimethyl-thiazol-5-yl)-pyrimidin-2-ylamino]-phenyl}-piperidin-4-yl)-propan-1-ol;
N-{5-[2-(4-Fluoro-phenylamino)-pyrimidin-4-yl]-4-methyl-thiazol-2-yl}-3-morpholin-4-yl-propionamide;
3-Bromo-N-{4-methyl-5-[2-(3-nitro-phenylamino)-pyrimidin-4-yl]-thiazol-2-yl}-propionamide;
N-{4-Methyl-5-[2-(3-nitro-phenylamino)-pyrimidin-4-yl]-thiazol-2-yl}-3-morpholin-4-yl-propionamide;
N-{4-Methyl-5-[2-(3-nitro-phenylamino)-pyrimidin-4-yl]-thiazol-2-yl}-3-(4-methyl-piperazin-1-yl)-propionamide;
[4-(2-Methoxy-4-methyl-thiazol-5-yl)-pyrimidin-2-yl]-[4-(4-methyl-piperazin-1-yl)-phenyl]-amine;
[4-(4-Benzyl-piperazin-1-yl)-phenyl]-[4-(4-methyl-2-methylamino-thiazol-5-yl)-pyrimidin-2-yl]-amine; and
3-Amino-N-{4-methyl-5-[2-(3-nitro-phenylamino)-pyrimidin-4-yl]-thiazol-2-yl}-propionamide.

The following compound is observed to be a particularly effective anti-viral agent, as demonstrated by cell based assays: [4-(2-Amino-4-methyl-thiazol-5-yl)-pyrimidin-2-yl]-(4-morpholin-4-yl-phenyl)-amine.

Another aspect of the invention relates to the use of a compound of formula I or Ia as an anti-mitotic agent.

Yet another aspect of the invention relates to the use of a compound of formula I or Ia for treating a neurodegenerative disorder.

Preferably, the neurodegenerative disorder is neuronal apoptosis.

Another aspect of the invention relates to the use of a compound of formula I or Ia as an antiviral agent.

Thus, another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of the invention is administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another aspect of the invention relates to the use of compounds of formula I or Ia, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M. X.; Bjorbaek, C.; Vestergaard, H.; Hansen, T.; Cohen, P. T.; Pedersen, O. *Diabetes*, 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. *Diabetes*, 2000, 49, 263].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of formula I or Ia, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [Goedert, M. *Curr. Opin. Gen. Dev.*, 2001, 11, 343]. Another aspect of the invention relates to the use of compounds of formula I or Ia, or pharmaceutically acceptable salts thereof, in the preparation of a medicament for treating bipolar disorder.

Yet another aspect of the invention relates to the use of compounds of formula I or Ia, or pharmaceutically acceptable salts thereof, in the preparation of a medicament for treating a stroke.

Reducing neuronal apoptosis is an important therapeutic goal in the context of head trauma, stroke, epilepsy, and motor neuron disease [Mattson, M. P. Nat. Rev. Mol. Cell. Biol., 2000, 1, 120]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of formula I or Ia, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated β-catenin [DasGupta, R.; Fuchs, E. Development, 1999, 126, 4557], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound of formula I or Ia, or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [Sunkel et al., *J. Cell Sci.*, 1988, 89, 25] and polo was found to encode a mitotic kinase [Llamazares et al., *Genes Dev.*, 1991, 5, 2153]. In humans, there exist three closely related PLKs [Glover et al., *Genes Dev.*, 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., *Proc. Natl. Acad. Sci. USA*, 1998, 95, 9301; Leung et al., *Nat. Struct. Biol.*, 2002, 9, 719], mediation of interactions with other proteins [Kauselmann et al., *EMBO J.*, 1999, 18, 5528], or may constitute part of an autoregulatory domain [Nigg, *Curr. Opin. Cell Biol.*, 1998, 10, 776]. Furthermore, the polo box-dependent PLK1 activity is required for proper metaphase/anaphase transition and cytokinesis [Yuan et al., *Cancer Res.*, 2002, 62, 4186; Seong et al., *J. Biol. Chem.*, 2002, 277, 32282].

Studies have shown that human PLKs regulate some fundamental aspects of mitosis [Lane et al., *J. Cell. Biol.*, 1996, 135, 1701; Cogswell et al., *Cell Growth Differ.*, 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., *Proc. Natl. Acad. Sci. USA*, 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., *Nature*, 2001, 410, 215; Roshak et al., *Cell. Signalling*, 2000, 12, 405], DNA-damage checkpoint activation [Smits et al., *Nat. Cell Biol.*, 2000, 2, 672; van Vugt et al., *J. Biol. Chem.*, 2001, 276, 41656], regulation of the anaphase promoting complex [Sumara et al., *Mol. Cell*, 2002, 9, 515; Golan et al., *J. Biol. Chem.*, 2002, 277, 15552; Kotani et al., *Mol. Cell*, 1998, 1, 371], phosphorylation of the proteasome [Feng et al., *Cell Growth Differ.*, 2001, 12, 29], and centrosome duplication and maturation [Dai et al., *Oncogene*, 2002, 21, 6195].

Specifically, initiation of mitosis requires activation of M-phase promoting factor (MPF), the complex between the cyclin dependent kinase CDK1 and B-type cyclins [Nurse, *Nature*, 1990, 344, 503]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, *Nat. Rev. Mol. Cell. Biol.*, 2001, 2, 21]. In interphase, cyclin B localizes to the cytoplasm [Hagting et al., *EMBO J.*, 1998, 17, 4127], it then becomes phosphorylated during prophase and this event causes nuclear translocation [Hagting et al., *Curr. Biol.*, 1999, 9, 680; Yang et al., *J. Biol. Chem.*, 2001, 276, 3604]. The nuclear accumulation of active MPF during prophase is thought to be important for initiating M-phase events [Takizawa et al., *Curr. Opin. Cell Biol.*, 2000, 12, 658]. However, nuclear MPF is kept inactive by WEE1 unless counteracted by CDC25C. The phosphatase CDC25C itself, localized to the cytoplasm during interphase, accumulates in the nucleus in prophase [Seki et al., *Mol. Biol. Cell*, 1992, 3, 1373; Heald et al., *Cell*, 1993, 74, 463; Dalal et al., *Mol. Cell. Biol.*, 1999, 19, 4465]. The nuclear entry of both cyclin B [Toyoshima-Morimoto et al., *Nature*, 2001, 410, 215] and CDC25C [Toyoshima-Morimoto et al., *EMBO Rep.*, 2002, 3, 341] are promoted through phosphorylation by PLK1 [Roshak et al., *Cell. Signalling*, 2000, 12, 405]. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang et al., *Mol. Cell. Biol.*, 2002, 22, 3450]. PLK2 is the least well understood homologue of the three PLKs. Both PLK2 and PLK3 may have additional important post-mitotic functions [Kauselmann et al., *EMBO J.*, 1999, 18, 5528].

Another aspect of the invention relates to the use of a compound of formula I for inhibiting a protein kinase.

In a preferred embodiment of this aspect, the protein kinase is a cyclin dependent kinase. Preferably, the protein kinase is CDK1, CDK2, CDK3, CDK4, CDK6, CDK7, CDK8 or CDK9, more preferably CDK2.

A further aspect of the invention relates to a method of inhibiting a protein kinase, said method comprising contacting said protein kinase with a compound of formula I.

In a preferred embodiment of this aspect, the protein kinase is a cyclin dependent kinase, even more preferably CDK2.

Pharmaceutical Compositions

A further aspect of the invention relates to a pharmaceutical composition comprising a compound of formula I as defined for said first aspect admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of formula I or Ia can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/ hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula I or Ia. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of formula I wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilizable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient for the treatment of malignancy.

Combinations

In a particularly preferred embodiment, the one or more compounds of the invention are administered in combination with one or more other anticancer agents, for example, existing anticancer drugs available on the market. In such cases, the compounds of the invention may be administered consecutively, simultaneously or sequentially with the one or more other anticancer agents.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Natural/Unnatural Amino Acids

In one preferred embodiment of the invention, $R^9$, $R^{10}$ or $R^{11}$ may be a natural or unnatural amino acid.

As used herein, the term "unnatural amino acid" refers to a derivative of an amino acid and may for example include alpha and alpha-disubstituted amino acids, N-alkyl amino acids, lactic acid, halide derivatives of natural amino acids such as trifluorotyrosine, p—Cl-phenylalanine, p—Br-phenylalanine, p-I-phenylalanine, L-allyl-glycine, β-alanine, L-α-amino butyric acid, L-γ-amino butyric acid, L-α-amino isobutyric acid, L-ϵ-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminoproprionic acid and L-Phe (4-benzyl).

Devices

In one preferred embodiment of the invention, the $R^9$, $R^{10}$ or $R^{11}$ groups allow for the immobilisation of the 2-phenylamino-4-heteroaryl-pyrimidine compounds onto a substrate. By way of example, the $R^9$, $R^{10}$ or $R^{11}$ groups may contain chemical functions that can be used for covalent attachment to solid phases such as functionalised polymers (e.g. agarose, polyacrylamide, polystyrene etc.) as commonly found in matrices (microtitre plate wells, microbeads, membranes, etc.), or used for biochemical assays or affinity chromatography. Alternatively, the $R^9$, $R^{10}$ or $R^{11}$ groups may linked to other small molecules (e.g. biotin) or polypeptides (e.g. antigens), which can be used for non-covalent immobilisation through binding to an immobilised receptor (e.g. avidin or streptavidin in the case of biotin, or a specific antibodies in the case of antigens).

Assays

Another aspect of the invention relates to the use of a compound of formula I or Ia as defined hereinabove in an assay for identifying further candidate compounds that influence the activity of one or more CDK enzymes.

Preferably, the assay is capable of identifying candidate compounds that are capable of inhibiting one or more of a CDK enzyme, GSK or a PLK enzyme.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralizing antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of formula I or Ia with a CDK enzyme in the presence of a known substrate of said CDK enzyme and detecting any change in the interaction between said CDK enzyme and said known substrate.

A further aspect of the invention provides a method of detecting the binding of a ligand to a CDK enzyme, said method comprising the steps of:
(i) contacting a ligand with a CDK enzyme in the presence of a known substrate of said CDK enzyme;
(ii) detecting any change in the interaction between said CDK enzyme and said known substrate;

and wherein said ligand is a compound of formula I or Ia.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:

(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more CDK enzymes.

The present invention is further described by way of example.

EXAMPLES

Example 1

Chemical synthesis. The covalent attachment of solubilising moieties can be achieved in a number of different ways known in the art (Wermuth C G. Preparation of water-soluble compounds by covalent attachment of solubilizing moieties. In: Practice of Medicinal Chemistry; Academic Press: London, UK, 1996; pp 755-776). For example, amino substituents in 2-phenylamino-4-heteroaryl-pyrimidine derivatives, or their synthetic precursors, can be acylated or alkylated with carbonyl functions in appropriate solubilising moiety precursors. Similarly, carbonyl groups in the 2-phenylamino-4-heteroaryl-pyrimidine derivatives can be animated or alkylated with appropriate solubilising moiety precursors. Halogen groups on aromatic C in phenylamino-4-heteroaryl-pyrimidines or precursors can be substituted through nucleophilic groups in solubilising moiety precursors. Suitable 2-phenylamino-4-heteroaryl-pyrimidine precursors may be prepared in accordance with the teachings of Fischer et al (Fischer P M, Wang S. PCT Intl. Patent Appl. Publ. WO 01/072745; Cyclacel Limited, UK, 2001). Some synthetic and analytical details for example compounds of the present invention (refer Table 1) are given in Example 2 below.

Example 2

[4-(2-Amino-4-methyl-thiazol-5-yl)-pyrimidin-2-yl]-(4-morpholin-4-yl-phenyl)-amine [1]. By condensation between N'-[5-(3-dimethylamino-acryloyl)-4-methyl-thiazol-2-yl]-N,N-dimethyl-formamidine (prepared from 1-(2-amino-4-methyl-thiazol-5-yl)-ethanone and N,N-dimethyl-formamide dimethylacetal) and N-(4-morpholin-4-yl-phenyl)-guanidine nitrate. Yellow solid. M.p. 300-304° C.: $^1$H-NMR (DMSO-$d_6$) δ: 2.46 (s, 3H, CH$_3$), 3.07 (m, 4H, CH$_2$), 3.76 (m, 4H, CH$_2$), 6.85 (d, 1H, J=5.3 Hz, pyrimidinyl-H), 6.92 (m, 2H, Ph-H), 7.53 (br. s, 1H, NH), 7.67 (m, 2H, Ph-H), 8.30 (d, 1H, J=5.4 Hz, pyrimidinyl-H), 9.25 (br. s, 1H, NH). MS (ESI$^+$) m/z 369 [M+H]$^+$ ($C_{18}H_{20}N_6OS$ requires 368.5).

[4-(2,4-Dimethyl-thiazol-5-yl)-pyrimidin-2-yl]-(4-morpholin-4-yl-phenyl)-amine [2]. By condensation between 3-dimethylamino-1-(2,4-dimethyl-thiazol-5-yl)-propenone and N-(4-morpholin-4-yl-phenyl)-guanidine nitrate. Pale solid. $^1$H-NMR (CDCl$_3$) δ: 2.69 (s, 3H, CH$_3$), 2.70 (s, 3H, CH$_3$), 3.14 (t, 4H, J=4.8 Hz, CH$_2$), 3.72 (t, 4H, J=4.9 Hz, CH$_2$), 6.89 (d, 1H, J=5.1 Hz, pyrimidinyl-H), 6.95 (d, 2H, J=8.8 Hz, Ph-H), 6.98 (br. s, 1H, NH), 7.53 (d, 2H, J=9.1 Hz, Ph-H), 8.38 (d, 1H, J=5.1 Hz, pyrimidinyl-H). MS (ESI$^+$) m/z 368 [M+H]$^+$ ($C_{19}H_{21}N_5OS$ requires 367.5).

[4-(2-N-Methylamino-4-methyl-thiazol-5-yl)-pyrimidin-2-yl]-(4-morpholinophenyl)-amine [3]. By condensation between 3-dimethylamino-1-(4-methyl-2-methylaminothiazol-5-yl)-propenone (prepared from 1-(4-methyl-2-methylamino-thiazol-5-yl)-ethanone and N,N-dimethylformamide dimethylacetal) and N-(4-morpholin-4-yl-phenyl)-guanidine nitrate. Pale solid. Anal. RP-HPLC: $t_R$=10.8 min (0-60% MeCN in 0.1% aq CF$_3$COOH over 20 min, 1 mL/min, purity >95%). $^1$H-NMR (DMSO-d$_6$) δ: 2.83 (s, 3H, CH$_3$), 2.84 (s, 3H, CH$_3$), 3.01 (t, 4H, J=5.0 Hz, CH$_2$), 3.72 (t, 4H, J=5.0 Hz, CH$_2$), 6.81 (d, 2H, J=5.5 Hz, pyrimidinyl-H), 6.87 (m, 2H, Ph-H), 7.61 (m, 2H, Ph-H), 8.12 (br. s, 1H, NH), 8.26 (d, 1H, J=5.5 Hz, pyrimidinyl-H), 9.19 (br. s, 1H, NH). MS (ESI$^+$) m/z 383 [M+H]$^+$ ($C_{19}H_{22}N_6OS$ requires 382.5).

[4-(2-Ethylamino-4-methyl-thiazol-5-yl)-pyrimidin-2-yl]-(4-morpholin-4-yl-phenyl)-amine [4]. By condensation between 3-dimethylamino-1-(2-ethylamino-4-methyl-thiazol-5-yl)-propenone (prepared from 1-(2-ethylamino-4-methyl-thiazol-5-yl)-ethanone and N,N-dimethylformamide dimethylacetal) and N-(4-morpholin-4-yl-phenyl)-guanidine nitrate. Pale solid. Anal. RP-HPLC: $t_R$=19.4 min (0-60% MeCN in 0.1% aq CF$_3$COOH over 20 min, 1 mL/min, purity >95%). $^1$H-NMR (DMSO-d$_6$) δ: 1.16 (t, J=7.5 Hz, 3H, CH$_3$), 2.48 (s, 3H, CH$_3$), 3.26 (m, 2H, CH$_2$), 3.01 (t, 4H, J=5.0 Hz, CH$_2$), 3.72 (t, 4H, J=5.0 Hz, CH$_2$), 6.80 (d, 2H, J=5.5 Hz, pyrimidinyl-H), 6.86 (d, 2H, J=9.0 Hz, Ph-H), 7.60 (d, 2H, J=9.0 Hz, Ph-H), 8.25 (d, 1H, J=5.0 Hz, pyrimidinyl-H), 8.50 (s, 1H, NH), 9.16 (br. s, 1H, NH).

1-(4-{4-[4-(2,4-Dimethyl-thiazol-5-yl)-pyrimidin-2-ylamino]-phenyl}-piperazin-1-yl)-ethanone [5]. A solution of 1-fluoro-4-nitrobenzene (6.7 g, 47.5 mmol), 1-piperazin-1-yl-ethanone (6.7 g, 52.3 mmol) and K$_2$CO$_3$ (6.6 g, 47.5 mmol) in DMSO (60 mL) was heated at 100° C. for 18 h. After cooling, the mixture was poured into H$_2$O (0.5 L). The resulting yellow precipitate was filtered and washed with H$_2$O to afford of 1-[4-(4-nitro-phenyl)-piperazin-1-yl]-ethanone (11.9 g). This was partially dissolved in EtOH (100 mL) and AcOH (50 mL). The mixture was warmed to ca. 65° C. and iron powder (–325 mesh, 12.0 g, 215 mmol) was added in 1-g portions. The mixture was heated at reflux for 2 hr and filtered through a pad of Celite. The filtrate was evaporated to leave a black oil, which was basified by addition of 2 M aq NaOH and was extracted with EtOAc. The combined organics were washed with brine, dried on MgSO$_4$, filtered, and evaporated in vacuo to afford 1-[4-(4-amino-phenyl)-piperazin-1-yl]-ethanone (6.7 g) as a yellow solid. An aliquot of this material (2.0 g, 9.12 mmol) was dissolved in EtOH (5 mL) and HNO$_3$ was added (69% aq soln., 1.26 mL, 19.61 mmol), followed by cyanamide (50% w/v aq soln., 2.48 mL, 31.92 mmol). The resulting mixture was heated at reflux for 18 h. It was cooled to room temperature and poured into Et$_2$O (100 mL). The ethereal layer was separated and concentrated. The resulting precipitate was filtered and washed with iPrOH/Et$_2$O, then neat Et$_2$O. The light brown solid was dried to afford N-[4-(4-acetyl-piperazin-1-yl)-phenyl]-guanidine nitrate (1.2 g). This material (1.1 g, 2.84 mmol) was dissolved in 2-methoxyethanol (14 mL) and K$_2$CO$_3$ (0.79 g, 5.68 mmol) was added, followed by 3-dimethylamino-1-(2,4-dimethyl-thiazol-5-yl)-propenone (0.60 g, 2.84 mmol). The resulting mixture was heated at 115° C. for 18 h. It was cooled and concentrated. The residue was purified by SiO$_2$ chromatography (9:1 EtOAc/2 M NH$_3$ in MeOH) and recrystallisation from iPr$_2$O/MeOH to afford the title compound (930 mg) as a light brown solid. $^1$H-NMR (CDCl$_3$) δ: 2.15 (s, 3H, CH$_3$), 2.69 (s, 3H, CH$_3$), 2.71 (s, 3H, CH$_3$), 3.12 (t, 2H, J=5.4 Hz, CH$_2$), 3.15 (t, 2H, J=5.4 Hz, CH$_2$), 3.63 (t, 2H, J=5.4 Hz, CH$_2$), 3.79 (t, 2H, J=5.4 Hz, CH$_2$), 6.90 (d, 1H, J=5.4 Hz, pyrimidinyl-H), 6.96 (m, 2H, Ph-H), 6.98 (br. s, 1H, NH), 7.54 (m, 2H, Ph-H), 8.39 (d, 1H, J=5.4 Hz, pyrimidinyl-H). MS (ESI$^+$) m/z 409.6 ($C_{21}H_{24}N_6OS$ requires 408.5).

[4-(2,4-Dimethyl-thiazol-5-yl)-pyrimidin-2-yl]-(4-piperazin-1-yl-phenyl)-amine [6]. To a solution of 1-(4-{4-[4-(2,4-dimethyl-thiazol-5-yl)-pyrimidin-2-ylamino]-phenyl}-piperazin-1-yl)-ethanone (0.67 g, 1.64 mmol) in EtOH (3 mL) was added 2 M aq HCl (25 mL) in a steady stream. The mixture was heated at reflux for 1 h, cooled, and basified by addition of solid Na$_2$CO$_3$. The product was extracted with EtOAc. The combined organics were washed with brine, dried on Na$_2$SO$_4$, filtered, and evaporated to afford the title compound (580 mg) as a yellow solid. $^1$H-NMR (CDCl$_3$)™: 2.62 (s, 3H, CH$_3$), 2.63 (s, 3H, CH$_3$), 2.99 (m, 4H, CH$_2$), 3.06 (m, 4H, CH$_2$), 6.81 (d, 1H, J=5.4 Hz, pyrimidinyl-H), 6.89 (m, 3H, Ph-H, NH), 7.44 (m, 2H, Ph-H), 8.31 (d, 1H, J=5.4 Hz, pyrimidinyl-H). MS (ESI$^+$) m/z 367 ($C_{19}H_{22}N_6S$ requires 366.5).

[4-(2,4-Dimethyl-thiazol-5-yl)-pyrimidin-2-yl]-[4-(4'-2"-ethoxyethanolpiperazino)-phenyl]-amine [7]. A mixture of [4-(2,4-dimethyl-thiazol-5-yl)-pyrimidin-2-yl]-(4-piperazin-1-yl-phenyl)-amine (0.1 g, 0.27 mmol), 2-(2-chloroethoxy)-ethanol (35 μL, 0.33 mmol), NaI (49 mg, 0.33 mmol), and K$_2$CO$_3$ (37 mg, 0.27 mmol) in MeCN (2 mL) in a sealed tube was heated at 170° C. for 15 min in a microwave reactor (SmithCreator, Personal Chemistry Ltd). The solvent was evaporated to dryness and the residue was purified by SiO$_2$ chromatography (98:2 to 95:5 EtOAc/2 M NH$_3$ in MeOH) to afford the title compound (78 mg) as yellow foam. $^1$H-NMR (CDCl$_3$) δ: 2.69 (s, 3H, CH$_3$), 2.71 (s, 3H, CH$_3$), 2.80-2.91 (m, 6H, CH$_2$), 3.30 (m, 4H, CH$_2$), 3.67 (m, 2H, CH$_2$), 3.73 (m, 2H, CH$_2$), 3.79 (m, 2H, CH$_2$), 6.89 (d, 1H, J=5.4 Hz, pyrimidinyl-H), 6.97 (m, 3H, Ph-H & NH), 7.52 (m, 2H, Ph-H), 8.02 (br. s, 1H, OH), 8.38 (d, 1H, J=5.4 Hz, pyrimidinyl-H). MS (ESI$^+$) m/z 456 ($C_{23}H_{30}N_6O_2S$ requires 454.6).

3-(4-{4-[4-(2,4-Dimethyl-thiazol-5-yl)-pyrimidin-2-ylamino]-phenyl}-piperazin-1-yl)-propan-1-ol [8]. Yellow solid. $^1$H-NMR (CDCl$_3$) δ: 2.69 (s, 3H, CH$_3$), 2.71 (s, 3H, CH$_3$), 2.75 (m, 2H, CH$_2$), 3.21 (m, 2H, CH$_2$), 3.84 (t, 2H, J=5.1 Hz, CH$_2$), 6.89 (d, 1H, J=5.4 Hz, pyrimidinyl-H), 6.95 (m, 2H, Ph-H), 6.98 (br. s, 1H, NH), 7.51 (m, 2H, Ph-H), 8.38 (d, 1H, J=5.4 Hz, pyrim-H). MS (ESI$^+$): m/z 425.8 ($C_{22}H_{28}N_6OS$ requires 424.6).

2-(4-{4-[4-(2,4-Dimethyl-thiazol-5-yl)-pyrimidin-2-ylamino]-phenyl}-piperazin-1-yl)-ethanol [9]. Yellow solid. $^1$H-NMR (CDCl$_3$) δ: 2.55 (t, 2H, J=5.4 Hz, CH$_2$), 2.62 (m, 10H, CH$_3$ & CH$_2$), 3.12 (t, 4H, J=4.9 Hz, CH$_2$), 3.60 (t, 2H, J=5.4 Hz, CH$_2$), 6.81 (d, 1H, J=5.4 Hz, pyrimidinyl-H), 6.88 (m, 2H, Ph-H), 7.05 (br. s, 1H, NH), 7.45 (m, 2H, Ph-H), 8.30 (d, 1H, J=5.1 Hz, pyrimidinyl-H). MS (ESI$^+$) m/z 411.7 ($C_{21}H_{26}N_6OS$ requires 410.5).

[4-(2,4-Dimethyl-thiazol-1-yl)-pyrimidin-2-yl]-[4-(4-methanesulfonyl-piperazin-1-yl)-phenyl]-amine [10]. A mixture of [4-(2,4-dimethyl-thiazol-5-yl)-pyrimidin-2-yl]-(4-piperazin-1-yl-phenyl)-amine (86 mg, 0.23 mmol) in anhydrous $CH_2Cl_2$ (2 mL) was added $Et_3N$ (39 µL, 0.28 mmol). After cooling to 0° C., methanesulfonyl chloride (22 µL, 0.28 mmol) was added dropwise. After 15 min stirring, the reaction mixture was warmed to room temperature and stirring was continued for 18 h. After evaporation, the residue was purified by $SiO_2$ chromatography (98:2 to 95:5 EtOAc/2 M $NH_3$ in MeOH) to afford the title compound (61 mg) as a yellow solid. $^1$H-NMR ($CDCl_3$) δ: 2.69 (s, 3H, $CH_3$), 2.71 (s, 3H, $CH_3$), 2.84 (s, 3H, $CH_3$), 3.26 (t, 4H, J=5.1 Hz, $CH_2$), 3.41 (t, 4H, J=5.1 Hz, $CH_2$), 6.91 (d, 1H, J=5.1 Hz, pyrimidinyl-H), 6.98 (d, 2H, J=8.8 Hz, Ph-H), 7.10 (br. s, 1H, NH), 7.56 (d, 2H, J=8.8 Hz, Ph-H), 8.30 (d, 1H, J=5.1 Hz, pyrimidinyl-H). MS (ESI$^+$) m/z 446 ($C_{20}H_{24}N_6O_2S_2$ requires 444.6).

[4-(4-Benzyl-piperazin-1-yl)-phenyl]-[4-(4-methyl-2-methylamino-thiazol-5-yl)-pyrimidin-2-yl]-amine [11]. 4-(4-Benzyl-piperazin-1-yl)-phenylamine (2.17 g, 8.12 mmol) was partially dissolved in EtOH (5 mL) and $HNO_3$ (69% aq soln., 1.05 mL, 16.32 mmol) was added dropwise, followed by cyanamide (50% aq soln., 1.13 mL, 16.32 mmol). The mixture was heated for 18 h at reflux. After working up N-[4-(4-benzyl-piperazin-1-yl)-phenyl]-guanidine nitrate (1.16 g) was obtained as a purple solid. A mixture of this material (2.66 mmol), 3-dimethylamino-1-(4-methyl-2-methylaminothiazol-5-yl)-propenone (0.60 g, 2.66 mmol), and $K_2CO_3$ (0.74 g, 5.32 mmol) in 2-methoxyethanol (15 mL) was heated at 120° C. for 18 h. After cooling, it was poured into EtOAc (100 mL) and filtered through a pad of silica. The filtrate was evaporated and the residue was purified by $SiO_2$ chromatography (heptane/EtOAc) to afford the title compound (442 mg) as a light tan solid. $^1$H-NMR ($CD_3OD$) δ: 2.44 (s, 3H, $CH_3$), 2.56-2.58 (m, 4H, $CH_2$), 2.91 (s, 3H, $CH_3$), 3.09 (m, 4H, $CH_2$), 3.51 (s, 2H, $CH_2$), 6.70 (d, 1H, J=5.6 Hz, pyrimidinyl-H), 6.87 (m, 2H, Ph-H), 7.22 (m, 1H, Ph-H), 7.27 (m, 4H, Ph-H), 7.43 (m, 2H, Ph-H), 8.15 (d, 1H, J=5.4 Hz, pyrimidinyl-H). MS (ESI$^+$) m/z 473.2 ($C_{26}H_{29}N_7S$ requires 471.6).

[4-(2,4-Dimethyl-thiazol-5-yl)-pyrimidin-2-yl]-[4-(4-methyl-piperazin-1-yl)-phenyl]-amine [12]. By condensation between 3-dimethylamino-1-(2,4-dimethyl-thiazol-5-yl)-propenone and N-[4-(4-methyl-piperazin-1-yl)-phenyl]-guanidine nitrate. Light yellow solid. $^1$H-NMR ($CDCl_3$) δ: 2.37 (s, 3H, $CH_3$), 2.61 (m, 4H, $CH_2$), 2.69 (s, 3H, $CH_3$), 2.70 (s, 3H, $CH_3$), 3.20 (m, 4H, $CH_2$), 6.88 (d, 1H, J=5.1 Hz, pyrimidinyl-H), 6.94 (s, 1H, NH), 6.96 (d, 2H, J=8.8 Hz, Ph-H), 7.51 (d, 2H, J=8.8 Hz, Ph-H), 8.38 (d, 1H, J=5.1 Hz, pyrimidinyl-H).

3-Amino-N-{4-methyl-5-[2-(3-nitro-phenylamino)-pyrimidin-4-yl]-thiazol-2-yl}-propionamide [13]. A mixture of [4-(2-amino-4-methyl-thiazol-5-yl)-pyrimidin-2-yl]-(3-nitro-phenyl)-amine (0.12 g, 0.37 mmol), Boc-βAla-OH (0.18 g, 0.93 mmol), 1,3-diisopropylcarbodiimide (0.07 mL, 0.45 mmol) and 4-N,N-dimethylaminopyridine (36 mg, 0.3 mmol) in of dry DMF (2 mL) was stirred at room temperature for 24 h. The reaction mixture was poured into ice water and extracted with EtOAc. The organics were combined and washed with brine, filtered, and dried on $MgSO_4$. The solvent was evaporated to give brown residue, which was purified by $SiO_2$ chromatography (1:1 EtOAc/PE) to afford ({4-Methyl-5-[2-(3-nitro-phenylamino)-pyrimidin-4-yl]-thiazol-2-ylcarbamoyl}-methyl)-carbamic acid tert-butyl ester as light yellow solid. Anal. RP-HPLC: $t_R$=19.5 min (0-60% MeCN in 0.1% aq $CF_3COOH$ over 20 min, 1 mL/min, purity >93%). $^1$H-NMR (DMSO-$d_6$) δ: 1.11 (s, 9H, $CH_3$), 2.54 (s, 3H, $CH_3$), 3.62 (m, 2H, $CH_2$), 5.38 (m, 2H, $CH_2$), 7.06 (d, 1H, J=5.5 Hz, pyrimidinyl-H), 7.46 (m, 1H, Ph-H), 7.72 (m, 1H, Ph-H), 8.15 (m, 1H, Ph-H), 8.45 (d, 1H, J=5.2 Hz, pyrimidinyl-H), 8.77 (s, 1H, NH). A solution of this material (97 mg, 0.19 mmol) in dioxane (5 mL) was treated with $CF_3COOH$ (1 ml). After stirring at room temperature for 22 h, the reaction mixture was evaporated and purified by preparative RP-HPLC (0-60% MeCN in 0.1% aq $CF_3COOH$ over 40 min, 9 mL/min) to afford the titled compound (34 mg) as a light yellow solid. Anal. RP-HPLC: $t_R$=14.0 min (0-60% MeCN in 0.1% aq $CF_3COOH$ over 20 min, 1 mL/min, purity >93%). $^1$H-NMR ($CD_3OD$) δ: 2.64 (s, 3H, $CH_3$), 3.30 (m, 2H, $CH_2$), 3.33 (m, 2H, $CH_2$), 7.14 (d, 1H, J=5.5 Hz, pyrimidinyl-H), 7.52 (t, 1H, J=8.2 Hz, Ph-H), 7.63 (m, 1H, Ph-H), 7.96 (m, 1H, Ph-H), 8.46 (d, 1H, J=5.5 Hz, pyrimidinyl-H), 8.88 (s, 1H, NH). MS (ESI$^+$) m/z 400.6 ($C_{17}H_{17}N_7O_3S$ requires 399.4).

(2S)-2-Amino-3-hydroxy-N-{4-methyl-5-[2-(3-nitro-phenylamino)-pyrimidin-4-yl]-thiazol-2-yl}-propionamide [14]. From Boc-L-Ser-OH. Pale solid. Anal. RP-HPLC: $t_R$=13.7 min (0-60% MeCN in 0.1% aq $CF_3COOH$ over 20 min, 1 mL/min, purity >93%). $^1$H-NMR ($CD_3OD$) δ: 2.45 (s, 3H, $CH_3$), 3.65-3.77 (m, 3H, CH & $CH_2$), 3.95 (br. s, 1H, OH), 7.03 (d, 1H, J=5.5 Hz, pyrimidinyl-H), 7.36 (t, 1H, J=6.5 Hz, Ph-H), 7.63 (m, 1H, Ph-H), 7.97 (m, 1H, Ph-H), 8.41 (d, 1H, J=5.5 Hz, pyrimidinyl-H), 8.63 (s, 1H, NH).

(2R,3R)-2-Amino-3-hydroxy-N-{4-methyl-5-[2-(3-nitro-phenylamino)-pyrimidin-4-yl]-thiazol-2-yl}-butyramide [15]. From Boc-D-Thr-OH. Yellow solid. $^1$H-NMR ($CD_3OD$) δ: 1.35 (d, 3H, J=6.1 Hz, $CH_3$), 2.66 (s, 1H, CH), 3.95 (d, 1H, J=5.4 Hz, CH), 7.17 (d, 1H, J=5.4 Hz, pyrimidinyl-H), 7.51 (m, 1H, Ph-H), 7.97 (m, 1H, Ph-H), 8.51 (d, 1H, J=5.5 Hz, pyrimidinyl-H), 8.92 (m, 1H, Ph-H).

(2R)-2-Amino-N-{4-methyl-5-[2-(3-nitro-phenylamino)-pyrimidin-4-yl]-thiazol-2-yl}-butyramide [16]. From Boc-D-Abu-OH. Yellow solid. $^1$H-NMR (DMSO-$d_6$) δ: 0.93 (t, 3H, J=7.6 Hz, $CH_3$), 0.94 (m, 2H, $CH_2$), 1.60 (s, 3H, $CH_3$), 3.00 (t, 1H, J=6.9 Hz, CH), 6.10 (d, 1H, J=5.5 Hz, pyrimidinyl-H), 6.44 (m, 1H, Ph-H), 6.77 (m, 1H, Ph-H), 6.87 (m, 1H, Ph-H), 7.42 (d, 1H, J=5.5 Hz, pyrimidinyl-H) and 7.86 (br. s, 1H, NH). MS (ESI$^+$) m/z 414.6 ($C_{18}H_{19}N_7O_3S$ requires 413.5).

(2S,3S)-2-Amino-3-hydroxy-N-{4-methyl-5-[2-(3-nitro-phenylamino)-pyrimidin-4-yl]-thiazol-2-yl}-butyramide [17]. From Boc-L-Thr-OH. Yellow solid. $^1$H-NMR ($CD_3OD$) δ: 1.19 (d, 3H, J=6.6 Hz, $CH_3$), 2.63 (s, 3H, $CH_3$), 3.89 (m, 1H, CH), 4.10 (m, 1H, CH), 7.20 (d, 1H, J=5.5 Hz, pyrimidinyl-H), 7.55 (t, 1H, J=8.0 Hz, Ph-H), 7.81 (d, 1H, J=8.5 Hz, Ph-H), 8.16 (d, 1H, J=8.5 Hz, Ph-H), 8.58 (d, 1H, J=5.5 Hz, pyrimidinyl-H), 8.80 (s, 1H, Ph-H) and 10.17 (s, 1H, NH).

4-Amino-N-{4-methyl-5-[2-(3-nitro-phenylamino)-pyrimidin-4-yl]-thiazol-2-yl}-butyramide [18]. Yellow solid. $^1$H-NMR ($CD_3OD$) δ: 1.87 (m, 2H, $CH_2$), 2.52 (s, 3H, $CH_3$), 2.56 (m, 2H, $CH_2$), 2.84 (m, 2H, $CH_2$), 7.17 (d, 1H, J=5.3 Hz, pyrimidinyl-H), 7.55 (t, 1H, J=8.3 Hz, Ph-H), 7.79 (m, 1H, Ph-H), 8.13 (m, 1H, Ph-H), 8.54 (d, 1H, J=5.3 Hz, pyrimidinyl-H), 8.83 (s, 1H, Ph-H) and 10.12 (s, 1H, NH).

3-Amino-N-{4-methyl-5-[2-(4-morpholin-4-yl-phenylamino)-pyrimidin-4-yl]-thiazol-2-yl}-propionamide [19]. Yellow solid. $^1$H-NMR (DMSO-$d_6$) δ: 2.57 (m, 2H, $CH_2$), 2.71 (s, 3H, $CH_3$), 2.92 (m, 2H, $CH_2$), 3.02 (m, 4H, $CH_2$), 3.73 (m, 4H, $CH_2$), 6.87 (d, 2H, J=8.0 Hz, Ph-H), 6.95 (d, 1H, J=5.3 Hz, pyrimidinyl-H), 7.61 (d, 1H, J=8.0 Hz, Ph-H), 8.38 (d, 1H, J=5.5 Hz, pyrimidinyl-H) and 9.32 (s, 1H, NH). MS (ESI$^+$) m/z 439 ($C_{21}H_{25}N_7O_2S$ requires 439.5).

3-Bromo-N-{5-[2-(4-fluoro-phenylamino)-pyrimidin-4-yl]-4-methyl-thiazol-2-yl}-propionamide [20]. A solution of [4-(2-amino-4-methyl-thiazol-5-yl)-pyrimidin-2-yl]-(4-fluoro-phenyl)-amine (0.3 g, 1.0 mmol) in DMF (2 mL) was cooled on an ice bath and was treated with 2-bromopropionyl chloride (0.17 g, 1.0 mmol). After completion of the addition, the reaction mixture was allowed to stir at room temperature for 18 h. It was poured into ice water and was extracted with $CH_2Cl_2$. The organics were combined, washed with brine, dried on $MgSO_4$, and the solvent was evaporated to leave a brown residue. This was purified by $SiO_2$ chromatography (1:1 EtOAc/PE) to afford the title compound as a light yellow solid. Anal. RP-HPLC: $t_R$=17.1 min (0-60% MeCN in 0.1% aq $CF_3COOH$ over 20 min, 1 mL/min, purity >93%). $^1$H-NMR (DMSO-$d_6$) δ: 1.99 (m, 2H, $CH_2$), 2.68 (s, 3H, $CH_3$), 4.65 (m, 2H, $CH_2$), 7.02 (d, 1H, J=5.2 Hz, pyrimidinyl-H), 7.11 (m, 2H, Ph-H), 7.62 (m, 2H, Ph-H), 8.19 (d, 1H, J=5.5 Hz, pyrimidinyl-H).

N-{5-[2-(4-Fluoro-phenylamino)-pyrimidin-4-yl]-4-methyl-thiazol-2-yl}-3-morpholin-4-yl-propionamide [21]. A solution of 3-bromo-N-{5-[2-(4-fluoro-phenylamino)-pyrimidin-4-yl]-4-methyl-thiazol-2-yl}-propionamide (20 mg, 0.046 mmol) and morpholine (8 μL, 0.092 mmol,) in DMF (2 mL) was stirred at room temperature for 2 h. The reaction mixture was purified by preparative RP-HPLC (0-60% MeCN in 0.1% aq $CF_3COOH$ over 40 min, 9 mL/min) to afford the title compound as a pale solid. Anal. RP-HPLC: $t_R$=13.3 min (0-60% MeCN in 0.1% aq $CF_3COOH$ over 20 min, 1 mL/min, purity >93%). $^1$H-NMR (CD$_3$OD) δ: 2.66 (s, 3H, $CH_3$), 3.23 (m, 2H, $CH_2$), 3.33 (m, 2H, $CH_2$), 3.41 (m, 4H, $CH_2$), 3.87 (m, 2H, $CH_2$), 4.13 (m, 2H, $CH_2$), 7.04-7.09 (m, 3H, pyrimidinyl-H & Ph-H), 7.68 (m, 2H, Ph-H), 8.39 (d, 1H, J=5.5 Hz, pyrimidinyl-H). MS (ESI$^+$) m/z 443.3 ($C_{21}H_{23}FN_6O_2S$ requires 442.5).

N-{4-Methyl-5-[2-(3-nitro-phenylamino)-pyrimidin-4-yl]-thiazol-2-yl}-3-morpholin-4-yl-propionamide [22]. Yellow solid. $^1$H-NMR (CD$_3$OD) δ: 2.64 (s, 3H, $CH_3$), 3.23 (m, 2H, $CH_2$), 3.33 (m, 2H, $CH_2$), 3.41 (m, 4H, $CH_2$), 3.87 (m, 2H, $CH_2$), 4.13 (m, 2H, $CH_2$), 7.04-7.09 (m, 3H, pyrimidinyl-H & Ph-H), 7.68 (m, 2H, Ph-H), 8.39 (d, 1H, J=5.5 Hz, pyrimidinyl-H). MS (ESI$^+$) m/z 443.3 ($C_{21}H_{23}FN_6O_2S$ requires 442.5).

N-{4-Methyl-5-[2-(3-nitro-phenylamino)-pyrimidin-4-yl]-thiazol-2-yl}-3-(4-methyl-piperazin-1-yl)-propionamide [23]. Yellow solid. $^1$H-NMR (CD$_3$OD) δ: 2.94 (s, 3H, $CH_3$), 3.01 (m, 2H, $CH_2$), 3.24-3.43 (m, 4H, $CH_2$), 3.65 (m, 2H, $CH_2$), 7.14 (d, 1H, J=5.5 Hz, pyrimidinyl-H), 7.52 (m, 1H, Ph-H), 7.86 (d, 1H, J=8.0 Hz, Ph-H), 7.99 (d, 1H, J=8.0 Hz, Ph-H), 8.44 (m, 1H, Ph-H) and 8.79 (d, 1H, J=5.5 Hz, pyrimidinyl-H). MS (ESI$^+$) m/z 485 ($C_{22}H_{26}N_8O_3S$ requires 482.6).

2-Chloro-N-{4-methyl-5-[2-(3-nitro-phenylamino)-pyrimidin-4-yl]-thiazol-2-yl}-acetamide [24]. A solution of [4-(2-amino-4-methyl-thiazol-5-yl)-pyrimidin-2-yl]-(3-nitro-phenyl)-amine (0.33 g, 1.0 mmol,) in dry DMF (3 mL) was cooled on an ice-water bath. Chloroacetyl chloride (0.22 g, 2.0 mmol) and pyridine (80 μL) were added. After stirring at room temperature for 18 h, the reaction mixture was concentrated, poured into ice water and extracted with $CH_2Cl_2$. The organic phases were combined, washed with brine, dried on $MgSO_4$ and evaporated to dryness. The resulting greenish residue was purified by $SiO_2$ chromatography (1:1 EtOAc/PE) to afford the title compound as a gray solid. Anal. RP-HPLC: $t_R$=20.6 min (0-60% MeCN in 0.1% aq $CF_3COOH$ over 20 min, 1 mL/min, purity >97%). $^1$H-NMR (DMSO-$d_6$) δ: 2.45 (s, 3H, $CH_3$), 4.12 (s, 2H, $CH_2$), 7.03 (d, 1H, J=5.2 Hz, pyrimidinyl-H), 7.42 (m, 1H, Ph-H), 7.63 (m, 1H, Ph-H), 8.01 (m, 1H, Ph-H), 8.41 (d, 1H, J=5.2 Hz, pyrimidinyl-H), 8.64 (s, 1H, Ph-H).

2-Chloro-N-{5-[2-(3-chloro-phenylamino)-pyrimidin-4-yl]-4-methyl-thiazol-2-yl}-acetamide [25]. Brown solid. $^1$H-NMR (DMSO-$d_6$) δ: 2.65 (s, 3H, $CH_3$), 4.42 (s, 2H, $CH_2$), 7.01 (m, 1H, Ph-H), 7.25 (m, 1H, Ph-H), 7.61 (d, 1H, J=5.5 Hz, pyrimidinyl-H), 7.98 (s, 1H, Ph-H), 8.75 (d, 1H, J=5.5 Hz, pyrimidinyl-H) and 10.09 (br. s, 1H, NH).

2-Chloro-N-{5-[2-(3-methoxy-phenylamino)-pyrimidin-4-yl]-4-methyl-thiazol-2-yl}-acetamide [26]. Brown solid. $^1$H NMR (DMSO-$d_6$) δ: 2.58 (s, 3H, $CH_3$), 3.78 (s, 3H, $CH_3$), 4.36 (s, 2H, $CH_2$), 6.51 (m, 1H, Ph-H), 7.08 (d, 1H, J=5.5, pyrimidinyl-H), 7.14 (t, 1H, J=8.0 Hz, Ph-H), 7.23 (m, 1H, Ph-H), 7.59 (s, 1H, Ph-H) and 8.45 (d, 1H, J=5.5 Hz, pyrimidinyl-H).

2-Chloro-N-{5-[2-(4-dimethylamino-phenylamino)-pyrimidin-4-yl]-4-methyl-thiazol-2-yl}-acetamide [27]. Yellow solid. $^1$H-NMR (CD$_3$OD) δ: 2.57 (s, 3H, $CH_3$), 3.23 (s, 6H, $CH_3$), 4.22 (s, 2H, $CH_2$), 7.06 (d, 1H, J=5.5 Hz, pyrimidinyl-H), 7.57 (d, 2H, J=9.5 Hz, Ph-H), 7.73 (d, 2H, J=9.5 Hz, Ph-H), 8.14 (br. s, 1H, NH) and 8.35 (d, 1H, J=5.5 Hz, pyrimidinyl-H).

4-({4-Methyl-5-[2-(3-nitro-phenylamino)-pyrimidin-4-yl]-thiazol-2-ylcarbamoyl}-methyl)-piperazine-1-carboxylic acid tert-butyl ester [28]. A solution of 2-chloro-N-{4-methyl-5-[2-(3-nitro-phenylamino)-pyrimidin-4-yl]-thiazol-2-yl}-acetamide (40 mg, 0.1 mmol) in DMF (2 mL) was cooled on an ice bath. Piperazine-1-carboxylic acid tert-butyl ester (40 mg, 0.21 mmol) was added. After stirring at room temperature for 16 h, the reaction mixture was purified by preparative RP-HPLC (0-60% MeCN in 0.1% aq $CF_3COOH$ over 40 min, 9 mL/min) to afford the title compound (20 mg) as a light yellow solid. Anal. RP-HPLC: $t_R$=16.9 min (0-60% MeCN in 0.1% aq $CF_3COOH$ over 20 min, 1 mL/min, purity >97%). $^1$H-NMR (CD$_3$OD) δ: 2.65 (s, 3H, $CH_3$), 2.87 (m, 4H, $CH_2$), 3.36 (m, 4H, $CH_2$), 4.66 (s, 2H, $CH_2$), 7.71 (m, 1H, pyrimidinyl-H), 7.89 (t, 1H, J=8.1 Hz, Ph-H), 8.15 (m, 1H, Ph-H), 7.42 (m, 1H, Ph-H), 7.67 (m, 2H, pyrimidinyl-H & Ph-H).

N-{5-[2-(4-Dimethylamino-phenylamino)-pyrimidin-4-yl]-4-methyl-thiazol-2-yl}-2-[2-(2-hydroxy-ethoxy)-ethylamino]-acetamide [29]. Anal. RP-HPLC: $t_R$=10.52 min (0-60% MeCN in 0.1% aq $CF_3COOH$ over 20 min, 1 mL/min, purity >97%). $^1$H-NMR (CD$_3$OD) δ: 3.28 (s, 3H, $CH_3$), 3.41 (s, 6H, $CH_3$), 4.04 (m, 2H, $CH_2$), 4.28 (m, 4H, $CH_2$), 4.34 (m, 2H, $CH_2$), 4.50 (m, 2H, $CH_2$), 4.94 (br. s, 2H, $CH_2$), 7.92 (d, 1H, J=5.5 Hz, pyrimidinyl-H), 8.00 (d, 2H, J=9.0 Hz, Ph-H), 8.41 (m, 1H, J=9.0 Hz, Ph-H), 8.87 (br. s, 1H, NH/OH), 9.31 (d, 1H, J=5.5 Hz, pyrimidinyl-H).

6-[5-(2-Oxo-hexahydro-thieno[3,4-d]imidazol-4-yl)-pentanoylamino]-hexanoic acid (2-{4-methyl-5-[2-(4-morpholin-4-yl-phenylamino)-pyrimidin-4-yl]-thiazol-2-ylcarbamoyl}-ethyl)-amide [30]. A solution of 3-amino-N-{4-methyl-5-[2-(4-morpholin-4-yl-phenylamino)-pyrimidin-4-yl]-thiazol-2-yl}-propionamide (75 mg, 0.17 mmol) in DMF (1 mL) was treated with succinimidyl-6-(biotinamide)hexanoate (32 mg, 0.085 mmol). After stirring at room temperature for 3 h, the reaction mixture was purified by preparative RP-HPLC (0-60% MeCN in 0.1% aq $CF_3COOH$ over 40 min, 9 mL/min) to afford the title compound as an orange solid. Anal. RP-HPLC: $t_R$=13.2 min (0-60% MeCN in 0.1% aq $CF_3COOH$ over 20 min, 1 mL/min, purity >97%). MS (ESI+) m/z 776 ($C_{37}H_{50}N_{10}O_5S_2$ requires 778.9).

N-{5-[2-(4-Fluoro-phenylamino)-pyrimidin-4-yl]-4-methyl-thiazol-2-yl}-methanesulfonamide [31]. This compound was prepared from [4-(2-amino-4-methyl-thiazol-5-yl)-pyrimidin-2-yl]-(4-fluoro-phenyl)-amine by treatment with methylsulfonyl chloride and $Et_3N$ in DMF. Gray solid; $^1$H-NMR (DMSO-$d_6$) δ: 3.31 (s, 3H, $CH_3$), 3.63 (s, 3H, $CH_3$), 7.32 (m, 1H, pyrimidinyl-H), 7.42 (m, 2H, Ph-H), 8.11 (m, 2H, Ph-H), 8.63 (d, 1H, J=5.0 Hz, pyrimidinyl-H).

N-{4-Methyl-5-[2-(3-nitro-phenylamino)-pyrimidin-4-yl]-thiazol-2-yl}-methane sulfonamide [32]. A mixture of [4-(2-amino-4-methyl-thiazol-5-yl)-pyrimidin-2-yl]-(3-nitro-phenyl)-amine (1.0 mmol, 0.33 g) and methylsulfonyl chloride (2.0 mmol, 0.22 g) in dry DMF (2 mL) was added Et$_3$N (0.28 mL). The reaction mixture was stirred at room temperature for 20 h. After cooling, the mixture was diluted with EtOAc, washed with brine, and dried over MgSO$_4$. The solvent was evaporated and the residue was purified by preparative RP-HPLC using a gradient from 10-70% MeCN in 0.1% aq CF$_3$COOH over 40 min. The title compound was obtained as an orange solid. Anal. RP-HPLC: $t_R$=17.4 min (0-60% MeCN in 0.1% aq CF$_3$COOH over 20 min, 1 mL/min, purity >97%). $^1$H-NMR (DMSO-d$_6$) δ: 3.10 (s, 3H, CH$_3$), 3.25 (s, 3H, CH$_3$), 7.05 (d, 1H, J=5.2 Hz, pyrimidinyl-H), 7.42 (m, 1H, Ph-H), 7.63 (m, 1H, Ph-H), 7.98 (m, 1H, Ph-H), 8.21 (d, 1H, J=5.2 Hz, pyrimidinyl-H), 8.42 (s, 1H, Ph-H), 9.18 (s, 1H, NH).

2-Chloro-N-{5-[2-(4-fluoro-phenylamino)-pyrimidin-4-yl]-4-methyl-thiazol-2-yl}-acetamide [33]. This compound was prepared from [4-(2-amino-4-methyl-thiazol-5-yl)-pyrimidin-2-yl]-(4-fluoro-phenyl)-amine. $^1$H-NMR (DMSO-d$_6$) δ: 2.94 (s, 3H, CH$_3$), 4.75 (s, 2H, CH$_2$), 7.44 (m, 3H, pyrimidinyl-H & Ph-H), 8.09 (m, 2H, Ph-H), 8.28 (s, 1H, NH), 8.80 (d, 1H, J=5.2 Hz, pyrimidinyl-H).

2-Chloro-N-{5-[2-(4-chloro-phenylamino)-pyrimidin-4-yl]-4-methyl-thiazol-2-yl}-acetamide [34]. This compound was prepared by chloroacetylation of [4-(2-amino-4-methyl-thiazol-5-yl)-pyrimidin-2-yl]-(4-chloro-phenyl)-amine. Brown solid. $^1$H-NMR (DMSO-d$_6$) δ: 2.65 (s, 3H, CH$_3$), 4.42 (s, 2H, CH$_2$), 7.01 (m, 1H, Ph-H), 7.25 (m, 1H, Ph-H), 7.61 (d, 1H, J=5.5, pyrimidinyl-H), 7.98 (s, 1H, Ph-H), 8.75 (d, 1H, J=5.5 Hz, pyrimidinyl-H), 10.09 (br. s, 1H, NH).

N-{5-[2-(4-Chloro-phenylamino)-pyrimidin-4-yl]-4-methyl-thiazol-2-yl}-3-morpholin-4-yl-propionamide [35]. By treatment of 3-chloro-N-{5-[2-(4-chloro-phenylamino)-pyrimidin-4-yl]-4-methyl-thiazol-2-yl}-propionamide with morpholine. Anal. RP-HPLC: $t_R$=12.7 min (10-70% MeCN, purity >95%). $^1$H-NMR (CDCl$_3$) δ: 1.50 (m, 2H, CH$_2$), 2.52 (s, 3H, CH$_3$), 3.05-3.78 (m, 8H, CH$_2$), 3.81 (m, 2H, CH$_2$), 7.12 (d, 1H, J=5.5 Hz, pyrimidinyl-H), 7.30 (d, 2H, J=7.0 Hz, Ph-H), 7.80 (d, 2H, J=7.0 Hz, Ph-H), 8.51 (d, 1H, J=5.0 Hz, pyrimidinyl-H), 9.80 (brs, 1H, NH).

N-{5-[2-(4-Chloro-phenylamino)-pyrimidin-4-yl]-4-methyl-thiazol-2-yl}-3-(2-diethylamino-ethylamino)-propionamide [36]. By treatment of 3-bromo-N-{5-[2-(4-chloro-phenylamino)-pyrimidin-4-yl]-4-methyl-thiazol-2-yl}-propionamide with N$^1$,N$^1$-diethyl-ethane-1,2-diamine. Anal. RP-HPLC: $t_R$=11.8 min (10-70% MeCN, purity >97%). $^1$H-NMR (DMSO-D$_6$) δ: 1.20 (t, 6H, J=7.0 Hz, CH$_3$), 1.53 (d, 2H, J=6.5 Hz, CH$_2$), 2.52 (s, 6H, CH$_3$), 3.18 (m, 4H, CH$_2$), 3.28 (m, 4H, CH$_2$), 7.13 (d, 1H, J=5.0 Hz, pyrimidinyl-H), 7.30 (m, 2H, Ph-H), 7.81 (m, 2H, Ph-H), 8.51 (d, 1H, J=5.0 Hz, pyrimidinyl-H), 9.82 (brs, 1H, NH).

N-{5-[2-(4-Chloro-phenylamino)-pyrimidin-4-yl]-4-methyl-thiazol-2-yl}-3-(2-morpholin-4-yl-ethylamino)-propionamide [37]. By treatment of 3-bromo-N-{5-[2-(4-chloro-phenylamino)-pyrimidin-4-yl]-4-methyl-thiazol-2-yl}-propionamide with 2-morpholin-4-yl-ethylamine (or 3-amino-N-{5-[2-(4-chloro-phenylamino)-pyrimidin-4-yl]-4-methyl-thiazol-2-yl}-propionamide with 4-(2-chloro-ethyl)-morpholine. Anal. RP-HPLC: $t_R$=11.5 min (10-70% MeCN, purity >97%). $^1$H-NMR (DMSO-D$_6$) δ: 1.52 (d, 2H, J=7.0 Hz, CH$_2$), 2.48 (m, 2H, CH$_2$), 2.52 (s, 3H, CH$_3$), 3.05-3.11 (m, 4H, CH$_2$), 3.25-3.28 (m, 6H, CH$_2$), 4.08 (m, 2H, CH$_2$), 7.13 (d, 1H, J=5.5 Hz, pyrimidinyl-H), 7.29 (m, 2H, Ph-H), 7.82 (m, 2H, Ph-H), 8.51 (d, 1H, J=5.5 Hz, pyrimidinyl-H), 9.82 (brs, 1H, NH).

N-{5-[2-(4-Methoxy-phenylamino)-pyrimidin-4-yl]-4-methyl-thiazol-2-yl}-3-morpholin-4-yl-propionamide [38]. By treatment of 3-bromo-N-{5-[2-(4-methoxy-phenylamino)-pyrimidin-4-yl]-4-methyl-thiazol-2-yl}-propionamide with morpholine. Anal. RP-HPLC: $t_R$=12.7 min (0-60% MeCN, purity >90%). $^1$H-NMR (CDCl$_3$) δ: 1.20 (m, 2H, CH$_2$), 2.54-2.63 (m, 7H, CH$_3$ and CH$_2$), 3.34 (m, 2H, CH$_2$), 3.80 (m, 5H, CH$_3$ and CH$_2$), 4.03 (m, 2H, CH$_2$), 6.87-6.92 (m, 3H, pyrimidinyl-H and Ph-H), 7.17 (brs, 1H, NH), 7.53 (m, 2H, Ph-H), 8.35 (m, 1H, pyrimidinyl-H), 10.33 (brs, 1H, NH).

N-{5-[2-(3-Methoxy-phenylamino)-pyrimidin-4-yl]-4-methyl-thiazol-2-yl}-3-morpholin-4-yl-propionamide [39]. By treatment of 3-bromo-N-{5-[2-(3-methoxyphenylamino)-pyrimidin-4-yl]-4-methyl-thiazol-2-yl}-propionamide with morpholine. Anal. RP-HPLC: $t_R$=13.6 min (0-60% MeCN, purity >94%). $^1$H-NMR (DMSO-D$_6$) δ: 1.20 (m, 2H, CH$_2$), 2.48 (m, 4H, CH$_2$), 2.58 (s, 3H, CH$_3$), 3.41-3.57 (m, 6H, CH$_2$), 3.79 (s, 3H, CH$_3$), 6.52 (d, 1H, J=7.0 Hz, Ph-H), 7.07 (d, 1H, J=5.4 Hz, pyrimidinyl-H), 7.15 (t, 1H, J=7.3 Hz, Ph-H), 7.22 (m, 1H, Ph-H), 7.62 (brs, 1H, Ph-H), 8.46 (d, 1H, J=5.5 Hz, pyrimidinyl-H), 9.58 (brs, 1H, NH). MS (ESI$^+$) m/z 456.01 [M+H]$^+$ (C$_{22}$H$_{26}$N$_6$SO$_3$ requires 454.55).

N-{5-[2-(4-Methoxy-phenylamino)-pyrimidin-4-yl]-4-methyl-thiazol-2-yl}-3-(4-methyl-piperazin-1-yl)-propionamide [40]. By treatment of 3-bromo-N-{5-[2-(4-methoxyphenylamino)-pyrimidin-4-yl]-4-methyl-thiazol-2-yl}-propionamide with 1-methyl-piperazine. Anal. RP-HPLC: $t_R$=13.0 min (0-60% MeCN, purity >94%). $^1$H-NMR (DMSO-D$_6$) δ: 1.17 (m, 2H, CH$_2$), 2.11 (m, 2H, CH$_2$), 2.48 (m, 4H, CH$_2$), 2.57 (s, 3H, CH$_3$), 3.28 (s, 3H, CH$_3$), 3.30 (m, 4H, CH$_2$), 3.72 (s, 3H, CH$_3$), 6.85 (m, 2H, Ph-H), 6.97 (m, 1H, pyrimidinyl-H), 7.63 (m, 2H, Ph-H), 8.38 (d, 1H, J=5.1 Hz, pyrimidinyl-H). MS (ESI$^+$) m/z 468.57 [M+H]$^+$ (C$_{23}$H$_{26}$N$_7$SO$_2$ requires 467.59).

N-{4-[4-(2,4-Dimethyl-thiazol-5-yl)-pyrimidin-2-ylamino]-phenyl}-acetamide [45]. By condensation between 3-dimethylamino-1-(2,4-dimethyl-thiazol-5-yl)-propenone and N-(4-acetamidophenyl)-guanidine nitrate. Pale solid. Mp. 219-220° C. $^1$H-NMR (DMSO-D$_6$) δ: 2.00 (s, 3H, CH$_3$), 2.61 (s, 3H, CH$_3$), 2.64 (s, 3H, CH$_3$), 7.04 (d, 1H, J=4.9 Hz, pyrimidinyl-H), 7.48 (d, 2H, J=8.8 Hz, Ph-H), 7.64 (d, 2H, J=8.8 Hz, Ph-H), 8.47 (d, 1H, J=5.4 Hz, pyrimidinyl-H), 9.58 (s, 1H, NH), 9.82 (s, 1H, NH). MS (ESI$^+$) m/z 340.02 [M+H]$^+$ (C$_{17}$H$_{17}$N$_5$OS requires 339.42).

N-{4-[4-(2,4-Dimethyl-thiazol-5-yl)-pyrimidin-2-ylamino]-phenyl}-N-methyl-acetamide [48]. By condensation reaction of 3-dimethylamino-1-(2,4-dimethyl-thiazol-5-yl)-propenone and N-(4-N-methylacetamidophenyl)-guanidine nitrate. $^1$H-NMR (DMSO-D$_6$) δ: 1.75 (s, 3H, CH$_3$), 2.62 (s, 3H, CH$_3$), 2.64 (s, 3H, CH$_3$), 3.11 (s, 3H, CH$_3$), 7.11 (d, 1H, J=4.9 Hz, pyrimidinyl-H), 7.24 (d, 2H, J=7.8 Hz, Ph-H), 7.83 (d, 2H, J=7.8 Hz, Ph-H), 8.53 (d, 1H, J=4.9 Hz, pyrimidinyl-H), 9.83 (brs, 1H, NH). MS (ESI$^+$) m/z 354.88 [M+H]$^+$ (C$_{18}$H$_{19}$N$_5$OS requires 353.44).

1-(4-{4-[4-(2,4-Dimethyl-thiazol-5-yl)-pyrimidin-2-ylamino]-phenyl}-piperazin-1-yl)-propan-2-ol [49]. By treatment of [4-(2,4-dimethyl-thiazol-5-yl)-pyrimidin-2-yl]-(4-piperazin-1-yl-phenyl)-amine with 1-chloro-2-propanol. $^1$H-NMR (CDCl$_3$) δ: 1.10 (d, 3H, J=6.0 Hz, CH$_3$), 2.26-2.33 (m, 2H, CH$_2$), 2.49-2.53 (m, 2H, CH$_2$), 2.61 (s, 3H, CH$_3$), 2.63 (s, 3H, CH$_3$), 2.76-2.80 (m, 2H, CH$_2$), 3.07-3.13 (m, 4H, CH$_2$), 3.83 (m, 1H, CH), 6.81 (d, 1H, J=4.4 Hz, pyrimidinyl-H), 6.88 (d, 2H, J=8.8 Hz, Ph-H), 7.02 (brs, 1H, OH), 7.44 (d, 2H, J=8.8 Hz, Ph-H), 8.30 (d, 1H, J=4.4 Hz, pyrimidinyl-H).

2-Chloro-N-{4-[4-(2,4-dimethyl-thiazol-5-yl)-pyrimidin-2-ylamino]-phenyl}-acetamide [50]. By treatment of [4-(2,4-dimethylthiazol-5-yl)-pyrimidin-2-yl]-(4-aminophenyl)-amine with chloroacetyl chloride. Mp. 217-219° C. $^1$H-NMR (DMSO-D$_6$) δ: 2.61 (s, 3H, CH$_3$), 2.64 (s, 3H, CH$_3$), 4.22 (s, 2H, CH$_2$), 7.05 (d, 1H, J=5.4 Hz, pyrimidinyl-H), 7.50 (d, 2H, J=8.8 Hz, Ph-H), 7.70 (d, 2H, J=8.8 Hz, Ph-H), 8.49 (d, 1H, J=4.9 Hz, pyrimidinyl-H), 9.65 (s, 1H, NH), 10.20 (s, 1H, NH). MS (ESI$^+$) m/z 374.47 [M+H]$^+$ (C$_{17}$H$_{16}$ClN$_5$OS requires 373.86).

N-{4-[4-(2,4-Dimethyl-thiazol-5-yl)-pyrimidin-2-ylamino]-phenyl}-2-morpholin-4-yl-acetamide [51]. By treatment of 2-chloro-N-{4-[4-(2,4-dimethyl-thiazol-5-yl)-pyrimidin-2-ylamino]-phenyl}-acetamide with morpholine. $^1$H-NMR (DMSO-D$_6$) δ: 2.61 (s, 3H, CH$_3$), 2.64 (s, 3H, CH$_3$), 3.09 (s, 2H, CH$_2$), 3.27-3.31 (m, 4H, CH$_2$), 3.62-3.64 (m, 4H, CH$_2$), 7.04 (d, 1H, J=5.4 Hz, pyrimidinyl-H), 7.54 (d, 2H, J=8.8 Hz, Ph-H), 7.67 (d, 2H, J=8.8 Hz, Ph-H), 8.48 (d, 1H, J=4.9 Hz, pyrimidinyl-H), 9.59 (s, 1H, NH). MS (ESI$^+$) m/z 425.01 [M+H]$^+$ (C$_{21}$H$_{24}$N$_6$O$_2$S requires 424.52).

N-{4-[4-(2,4-Dimethyl-thiazol-5-yl)-pyrimidin-2-ylamino]-phenyl}-2-[1,2,4]triazol-5-yl-acetamide [52]. By treatment of 2-chloro-N-{4-[4-(2,4-dimethyl-thiazol-5-yl)-pyrimidin-2-ylamino]-phenyl}-acetamide with 1H-[1,2,4] triazole. $^1$H-NMR (DMSO-D$_6$) δ: 2.61 (s, 3H, CH$_3$), 2.63 (s, 3H, CH$_3$), 5.10 (s, 2H, CH$_2$), 7.05 (d, 1H, J=5.4 Hz, pyrimidinyl-H), 7.50 (d, 2H, J=8.3 Hz, pyrimidinyl-H), 7.69 (d, 2H, J=8.9 Hz, Ph-H), 7.98 (s, 1H, Aryl-H), 8.48 (d, 1H, J=4.9 Hz, pyrimidinyl-H), 8.53 (s, 1H, Aryl-H), 9.62 (brs, 1H, NH), 10.30 (brs, 1H, NH). MS (ESI$^+$) m/z 406.97 (C$_{19}$H$_{18}$N$_8$OS requires 406.47).

N-{4-[4-(2,4-Dimethyl-thiazol-5-yl)-pyrimidin-2-ylamino]-phenyl}-2-pyrrolidin-1-yl-acetamide [53]. By treatment of 2-chloro-N-{4-[4-(2,4-dimethyl-thiazol-5-yl)-pyrimidin-2-ylamino]-phenyl}-acetamide with pyrrolidine. $^1$H-NMR (DMSO-D$_6$) δ: d 1.74 (m, 4H, CH$_2$), 2.58 (m, 4H, CH$_2$), 2.61 (s, 3H, CH$_3$), 2.64 (s, 3H, CH$_3$), 3.20 (s, 2H, CH$_2$), 7.04 (d, 1H, J=5.4 Hz, pyrimidinyl-H), 7.55 (d, 2H, J=8.8 Hz, Ph-H), 7.66 (d, 2H, J=8.8 Hz, Ph-H), 8.48 (d, 1H, J=5.4 Hz, pyrimidinyl-H), 9.55 (s, 1H, NH), 9.58 (s, 1H, NH). MS (ESI$^+$) m/z 406.97 [M+H]$^+$ (C$_{21}$H$_{24}$N$_6$OS requires 408.52).

N-{4-[4-(2,4-Dimethyl-thiazol-5-yl)-pyrimidin-2-ylamino]-phenyl}-2-imidazol-1-yl-acetamide [54]. By treatment of 2-chloro-N-{4-[4-(2,4-dimethyl-thiazol-5-yl)-pyrimidin-2-ylamino]-phenyl}-acetamide with 1H-imidazole. $^1$H-NMR (DMSO-D$_6$) δ: 2.61 (s, 3H, CH$_3$), 2.63 (s, 3H, CH$_3$), 4.86 (s, 2H, CH$_2$), 6.88 (s, 1H, Aryl-H), 7.04 (d, 1H, J=5.9 Hz, pyrimidinyl-H), 7.15 (s, 1H, Aryl-H), 7.50 (d, 2H, J=7.8 Hz, Ph-H), 7.62 (s, 1H, Aryl-H), 7.68 (d, 2H, J=7.8 Hz, Ph-H), 8.48 (d, 1H, J=5.4 Hz, pyrimidinyl-H), 9.60 (s, 1H, NH), 10.18 (brs, 1H, NH). MS (ESI$^+$) m/z 406.02 [M+H]$^+$ (C$_{20}$H$_{19}$N$_7$OS requires 405.48).

3-[4-(4-Methyl-2-morpholin-4-yl-thiazol-5-yl)-pyrimidin-2-ylamino]-phenol [55]. A solution of morpholine-4-carbonitrile (10 g, 89.19 mmol) in EtOH (65 mL) was cooled on an ice bath. Anhydrous NH$_3$ was bubbled through the solution for 5 min, followed by hydrogen sulfide. Soon after the introduction of H$_2$S a white precipitate was observed. After the addition of both gases for 45 min NH$_3$ addition was stopped and H$_2$S continued for a further 15 minutes. The resulting precipitate was collected, washed with cold water, MeOH and dried under high vacuum to afford morpholine-4-carbothioic acid amide (12.83 g). Mp. 173-174° C. $^1$H-NMR (DMSO-D$_6$) δ: 3.54 (t, 4H, J=4.9 Hz, CH$_2$), 3.70 (m, 4H, CH$_2$), 7.46 (brs, 2H, NH$_2$). This was converted first to 1-(4-methyl-2-morpholin-4-yl-thiazol-5-yl)-ethanone with 3-bromo-pentane-2,4-dione, then with dimethoxymethyl-dimethyl-amine to 3-dimethylamino-1-(4-methyl-2-morpholin-4-yl-thiazol-5-yl)-propenone in the usual manner. The latter enaminone was condensed with N-(3-hydroxy-phenyl)-guanidine nitrate to afford the title compound as a. pale solid. Mp. 227-229 C. $^1$H-NMR (DMSO-D$_6$) δ: 2.49 (s, 3H, CH$_3$), 3.46 (t, 4H, J=4.4 Hz, CH$_2$), 3.71 (t, 4H, J=4.4 Hz, pyrimidinyl-H), 6.34 (d, 1H, J=8.8 Hz, Ph-H), 6.91 (d, 1H, J=5.4 Hz, pyrimidinyl-H), 7.03 (t, 1H, J=7.8 Hz, Ph-H), 7.20-7.22 (m, 2H, Ph-H), 8.34 (d, 1H, J=5.4 Hz, pyrimidinyl-H), 9.17 (s, 1H, OH/NH), 9.32 (s, 1H, NH/OH). MS (ESI$^+$) m/z 370.10 [M+H]$^+$ (C$_{18}$H$_{19}$N$_5$O$_2$S requires 369.44).

[4-(4-Methyl-2-morpholin-4-yl-thiazol-5-yl)-pyrimidin-2-yl]-(4-morpholin-4-yl-phenyl)-amine [56]. By treatment of 3-dimethylamino-1-(4-methyl-2-morpholino-thiazol-5-yl)-propenone and N-(4-morpholinophenyl)-guanidine nitrate. Pale solid. Mp. 229-231° C. $^1$H-NMR (DMSO-D$_6$) δ: 2.48 (s, 3H, CH$_3$), 3.02 (t, 4H, J=4.0 Hz, CH$_2$), 3.46 (t, 4H, J=4.0 Hz, CH$_2$), 3.70-3.73 (m, 8H, CH$_2$), 6.86 (d, 1H, J=5.4 Hz, pyrimidinyl-H), 6.89 (d, 2H, J=9.3 Hz, Ph-H), 7.60 (d, 2H, J=8.8 Hz, Ph-H), 8.30 (d, 1H, J=5.4 Hz, pyrimidinyl-H), 9.22 (s, 1H, NH). MS (ESI$^+$) m/z 439.03 [M+H]$^+$ (C$_{22}$H$_{26}$N$_6$O$_2$S requires 438.55).

N,N-Dimethyl-N'-[4-(4-methyl-2-morpholin-4-yl-thiazol-5-yl)-pyrimidin-2-yl]-benzene-1,4-diamine [57]. By treatment of 3-dimethylamino-1-(4-methyl-2-morpholino-thiazol-5-yl)-propenone and N-(4-N,N-dimethylaminophenyl)-guanidine nitrate. Yellow solid. $^1$H-NMR (DMSO-D$_6$) δ: 2.48 (s, 3H, CH$_3$), 2.82 (s, 6H, CH$_3$), 3.46 (t, 4H, J=4.9 Hz, pyrimidinyl-H), 3.70 (t, 4H, J=4.9 Hz, CH$_2$), 6.70 (d, 2H, J=8.8 Hz, Ph-H), 6.82 (d, 1H, J=5.4 Hz, pyrimidinyl-H), 7.53 (d, 2H, J=8.8 Hz, Ph-H), 8.27 (d, 1H, J=5.4 Hz, pyrimidinyl-H), 9.09 (s, 1H, NH). MS (ESI$^+$) m/z 397.03 [M+H]$^+$ (C$_{20}$H$_{24}$N$_6$OS requires 396.51).

2-{4-[4-(4-Methyl-2-methylamino-thiazol-5-yl)-pyrimidin-2-ylamino]-phenyl}-ethanol [59]. By condensation between 3-dimethylamino-1-(4-methyl-2-methylamino-thiazol-5-yl)-propenone and N-[4-(2-hydroxy-ethyl)-phenyl]-guanidine nitrate. Pale solid. Mp 216-218° C. Anal. RP-HPLC: t$_R$=9.1 min (10-70% MeCN, purity >95%). $^1$H-NMR (DMSO-d$_6$) δ: 2.46 (s, 3H, CH$_3$), 3.05 (s, 3H, CH$_3$), 3.55 (m, 2H, CH$_2$), 4.58 (m, 2H, CH$_2$), 6.85 (d, 1H, J=5.5 Hz, pyrimidinyl-H), 7.08 (m, 2H, Ph-H), 7.64 (m, 2H, Ph-H), 8.01 (m, 1H, OH), 8.29 (d, 1H, J=5.5 Hz, pyrimidinyl-H), 9.30 (brs, 1H, NH). MS (ESI$^+$) m/z 363.99 [M+H]$^+$Na (C$_{17}$H$_{19}$N$_5$SONa requires 364.43).

1-(4-{{4-[4-(4-Methyl-2-methylamino-thiazol-5-yl)-pyrimidin-2-ylamino]-phenyl}-piperazin-1-yl)-ethanone [61]. By condensation between 3-dimethylamino-1-(4-methyl-2-methylamino-thiazol-5-yl)-propenone and N-[4-(4-acetyl-piperazin-1-yl)-phenyl]-guanidine nitrate. Yellow solid. Mp 213-214° C. Anal. RP-HPLC: t$_R$=8.8 min (10-70% MeCN, purity >95%). $^1$H-NMR (DMSO-d$_6$) δ: 2.43 (s, 3H, CH$_3$), 3.02 (s, 3H, CH$_3$), 3.23 (s, 3H, CH$_3$), 2.99 (m, 2H, CH$_2$), 3.06 (t, 2H, CH$_2$), 3.57 (t, 4H, CH$_2$), 6.82 (d, 1H, J=6.0 Hz, pyrimidinyl-H), 6.89 (d, 2H, J=9.0 Hz, Ph-H), 7.62 (d, 2H, J=9.5 Hz, Ph-H), 8.26 (d, 1H, J=5.5 Hz, pyrimidinyl-H), 9.18 (s, 1H, NH). MS (ESI$^+$) m/z 424.07 [M+H]$^+$ (C$_{21}$H$_{25}$N$_7$OS requires 423.54).

[4-(4-Methyl-2-methylamino-thiazol-5-yl)-pyrimidin-2-yl]-(4-piperazin-1-yl-phenyl)-amine [62]. By hydrolysis of 1-(4-{4-[4-(4-Methyl-2-methylamino-thiazol-5-yl)-pyrimidin-2-ylamino]-phenyl}-piperazin-1-yl)-ethanone in 2 M aq HCl. Yellow solid. Anal. RP-HPLC: t$_R$=8.8 min (10-70% MeCN, purity >95%). $^1$H-NMR (DMSO-d$_6$) δ: 2.45 (3, 3H, CH$_3$), 2.83 (t, 4H, J=5.9 Hz, CH$_2$), 2.85 (t, 4H, J=4.9 Hz, CH$_2$), 2.95 (t, 4H, J=4.9 Hz, CH$_2$), 6.81 (d, 1H, J=5.4 Hz, pyrimidinyl-H), 6.85 (d, 2H, J=9.3 Hz, Ph-H), 7.58 (d, 2H, J=8.8 Hz, Ph-H), 7.99 (m, 1H, NH), 8.26 (d, 1H, J=5.4 Hz, pyrimidinyl-H), 9.14 (brs, 1H). N-{3-[4-(4-Methyl-2-methylamino-thiazol-5-yl)-pyrimidin-2-ylamino]-benzyl}-acetamide [63]. By condensation of 3-dimethylamino-1-(2-methylamino-4-methyl-thiazol-5-yl)-propenone and N-(3-guanidino-benzyl)-acetamide nitrate. Yellow solid. Mp 253-255° C. Anal. RP-HPLC: $t_R$=11.3 min (10-70% MeCN, purity >95%): $^1$H NMR (DMSO): δ 1.86 (s, 3H, CH$_3$), 2.46 (s, 3H, CH$_3$), 2.85 (s, 2H, CH$_2$), 3.09 (s, 3H, CH$_3$), 6.82 (d, 1H, J=8.0 Hz, ph-H), 6.88 (d, 1H, J=5.5 Hz, pyrimidinyl-H), 7.2 (t, 1H, J=8.0 Hz, Ph-H), 7.60 (d, 1H, J=8.0 Hz, Ph-H), 7.73 (s, 1H, Ph-H), and 8.32 (d, 1H, J=5.5 Hz, pyrimidinyl-H). MS (ESI$^+$) m/z 391.55 [M+Na] (C$_{18}$H$_{20}$N$_6$OSNa requires 391.46).

N-{3-[4-(2-Ethylamino-4-methyl-thiazol-5-yl)-pyrimidin-2-ylamino]-benzyl}-acetamide [64]. By condensation of 3-dimethylamino-1-(2-ethylamino-4-methyl-thiazol-5-yl)-propenone and N-(3-guanidino-benzyl)-acetamide nitrate. Yellow solid. Anal. RP-HPLC: $t_R$=12.7 min (0-60% MeCN, purity >95%). $^1$H-NMR (CD$_3$OD) δ: 1.17 (t, 3H, J=7.5 Hz, CH$_3$), 1.98 (s, 3H, CH$_3$), 2.51 (s, 3H, CH$_3$), 3.36 (q, 2H, J=7.1 Hz, CH$_2$), 4.39 (s, 2H, CH$_2$), 6.92 (m, 2H, pyrimidinyl-H and Ph-H), 7.25 (t, 1H, J=7.6 Hz, Ph-H), 7.49 (m, 1H, Ph-H), 7.79 (sbr, 1H, Ph-H), 8.25 (d, 1H, J=5.5 Hz, pyrimidinyl-H). MS (ESI$^+$) m/z 383.46 [M+H]$^+$ (C$_{19}$H$_{22}$N$_6$OS requires 382.48).

(3-Aminomethyl-phenyl)-[4-(2-ethylamino-4-methyl-thiazol-5-yl)-pyrimidin-2-yl]-amine [65]. By hydrolysis of N-{3-[4-(2-ethylamino-4-methyl-thiazol-5-yl)-pyrimidin-2-ylamino]-benzyl}-acetamide. Yellow solid. Mp 290-292° C. Anal. RP-HPLC: $t_R$=10.6 min (10-70% MeCN, purity >95%). $^1$H-NMR (DMSO-D$_6$) δ: 1.31 (t, 3H, J=7.0 Hz, CH$_3$), 2.64 (s, 3H, CH$_3$), 3.54 (m, 2H, CH$_2$), 4.11 (m, 2H, CH$_2$), 7.14 (d, 1H, J=6.0 Hz, pyrimidinyl-H), 7.22 (d, 1H, J=8.0 Hz, Ph-H), 7.45 (t, 1H, J=8.0 Hz, Ph-H), 7.74 (d, 1H, J=8.0 Hz, Ph-H), 7.95 (s, 1H, Ph-H), 8.53 (d, 1H, J=6.0 Hz, pyrimidinyl-H). MS (ESI$^+$) m/z 341.20 [M+H]$^+$ (C$_{17}$H$_{20}$N$_6$S requires 340.45).

N-{3-[4-(2,4-Dimethyl-thiazol-5-yl)-pyrimidin-2-ylamino]-benzyl}-acetamide [66]. By treatment of 3-dimethylamino-1-(2,4-dimethyl-thiazol-5-yl)-propenone and N-(3-guanidino-benzyl)-acetamide nitrate. Yellow solid. Mp 206-207° C. Anal. RP-HPLC: $t_R$=13.6 min (0-60% MeCN, purity >95%). $^1$H-NMR (DMSO-D$_6$) δ: 1.99 (s, 3H, CH$_3$), 2.65 (s, 3H, CH$_3$), 2.68 (s, 3H, CH$_3$), 4.38 (s, 2H, CH$_2$), 6.94 (d, 1H, J=7.5 Hz, Ph-H), 7.01 (1H, J=5.5 Hz, pyrimidinyl-H), 7.26 (d, 1H, J=8.0 Hz, Ph-H), 7.56 (d, 1H, J=7.5 Hz, Ph-H), 7.70 (s, 1H, Ph-H), 8.40 (d, 1H, J=5.5 Hz, pyrimidinyl-H). MS (ESI$^+$) m/z 345.42 [M+H]$^+$ (C$_{18}$H$_{19}$N$_5$OS requires 353.44).

(3-Aminomethyl-phenyl)-[4-(4-methyl-2-methylamino-thiazol-5-yl)-pyrimidin-2-yl]-amine [67]. By treatment of N-{3-[4-(4-methyl-2-methylamino-thiazol-5-yl)-pyrimidin-2-ylamino]-benzyl}-acetamide with HCl/MeOH. Yellow solid. Mp 287-289° C. Anal. RP-HPLC: $t_R$=10.1 min (0-60% MeCN, purity 92%). $^1$H-NMR (DMSO-D$_6$) δ: 2.68 (s, 3H, CH$_3$), 3.17 (s, 3H, CH$_3$), 4.17 (m, 2H, CH$_2$), 7.23 (d, 1H, J=6.0 Hz, pyrimidinyl-H), 7.27 (d, 1H, J=8.0 Hz, Ph-H), 7.50 (t, 1H, J=8.0 Hz, Ph-H), 7.70 (d, 1H, J=7.5 Hz, Ph-H), 7.75 (s, 1H, Ph-H), 8.44 (d, 1H, J=6.0 Hz, pyrimidinyl-H). MS (ESI$^+$) m/z 327.37 [M+H]$^+$ (C$_{16}$H$_{18}$N$_6$S requires 326.42).

{3-[4-(2-Ethylamino-4-methyl-thiazol-5-yl)-pyrimidin-2-ylamino]-phenyl}-methanol [68]. By condensation of 3-dimethylamino-1-(2-ethylamino-4-methyl-thiazol-5-yl)-propenone and N-(3-hydroxymethyl-phenyl)-guanidine nitrate. Yellow solid. Anal. RP-HPLC: $t_R$=12.6 min (0-60% MeCN, purity >95%). $^1$H-NMR (CD$_3$OD) δ: 1.28 (t, 3H, J=7.3 Hz, CH$_3$), 2.52 (s, 3H, CH$_3$), 3.35 (q, 2H, J=7.1 Hz, CH$_2$), 4.63 (s, 2H, CH$_2$), 5.49 (d, 1H, J=5.5 Hz, pyrimidinyl-H), 7.63 (d, 1H, J=7.6 Hz, Ph-H), 7.27 (t, 1H, J=7.9 Hz, Ph-H), 7.52 (m, 1H, Ph-H), 7.79 (sbr, 1H, Ph-H), 8.26 (d, 1H, J=5.5 Hz, pyrimidinyl-H). MS (ESI$^+$) m/z 346.44 [M+H]$^+$ (C$_{17}$H$_{19}$N$_5$OS requires 341.43).

[4-(4-Methyl-2-morpholin-4-yl-thiazol-5-yl)-pyrimidin-2-yl]-(3-nitro-phenyl)-amine [71]. By condensation of 3-dimethylamino-1-(4-methyl 2-morpholin-4-yl-thiazol-5-yl)-propenone and N-(3-nitro-phenyl)-guanidine nitrate. Yellow solid. Anal. RP-HPLC: $t_R$=16.7 min (10-70% MeCN, purity >95%). $^1$H-NMR (DMSO-D$_6$) δ: 2.51 (s, 3H, CH$_3$), 3.50 (t, 4H, J=4.5 Hz, CH$_2$), 3.72 (t, 4H, J=4.5 Hz, CH$_2$), 7.06 (d, 1H, J=5.5 Hz, pyrimidinyl-H), 7.55 (t, 1H, J=8.5 Hz, Ph-H), 7.77 (d, 1H, J=8.5 Hz, Ph-H), 7.97 (d, 1H, J=8.5 Hz, Ph-H), 8.44 (d, 1H, J=5.5 Hz, pyrimidinyl-H), 9.03 (s, 1H, Ph-H), 10.06 (sbr, 1H, NH). MS (ESI$^+$) m/z 399.20 [M+H]$^+$ (C$_{18}$H$_{18}$N$_6$O$_3$S requires 398.44).

{2-Chloro-5-[4-(2,4-dimethyl-thiazol-5-yl)-pyrimidin-2-ylamino]-phenyl}-methanol [72]. By condensation of 3-dimethylamino-1-(2,4-dimethyl-thiazol-5-yl)-propenone and N-(4-chloro-3-hydroxymethyl-phenyl)-guanidine nitrate. Yellow solid. Mp 245-246° C. Anal. RP-HPLC: $t_R$=14.6 min (10-70% MeCN, purity >95%). $^1$H-NMR (DMSO-D$_6$) δ: 2.62 (s, 3H, CH$_3$), 2.63 (s, 3H, CH$_3$), 4.53 (d, 2H, J=5.5 Hz, CH$_2$), 5.34 (m, 1H, OH), 7.08 (d, 1H, J=5.5 Hz, pyrimidinyl-H), 7.29 (m, 1H, Ph-H), 7.73 (m, 1H, Ph-H), 7.94 (s, 1H, Ph-H), 8.51 (d, 1H, J=5.5 Hz, pyrimidinyl-H), 9.78 (s, 1H, NH). MS (ESI$^+$) m/z 347.11 [M+H]$^+$ (C$_{16}$H$_{15}$ClN$_4$OS requires 346.84).

{2-Chloro-5-[4-(4-methyl-2-methylamino-thiazol-5-yl)-pyrimidin-2-ylamino]-phenyl}-methanol [73]. By condensation of 3-dimethylamino-1-(2-methylamino-4-methyl-thiazol-5-yl)-propenone and N-(4-chloro-3-hydroxymethyl-phenyl)-guanidine nitrate. Yellow solid. Mp 191-193° C. Anal. RP-HPLC: $t_R$=11.5 min (10-70% MeCN, purity >90%). $^1$H-NMR (DMSO-D$_6$) δ: 2.46 (s, 3H, CH$_3$), 3.08 (s, 3H, CH$_3$), 4.52 (d, 2H, J=6.0 Hz, CH$_2$), 5.29 (m, 1H, OH), 6.89 (d, 1H, J=5.5 Hz, pyrimidinyl-H), 7.25 (d, 1H, J=8.5 Hz, Ph-H), 7.73 (m, 1H, Ph-H), 7.94 (s, 1H, Ph-H), 8.03 (sbr, 1H, NH), 8.32 (d, 1H, J=5.5 Hz, pyrimidinyl-H), 9.55 (s, 1H, NH). MS (ESI$^+$) m/z 361.89 [M](C$_{16}$H$_{16}$ClN$_5$OS requires 361.85).

[4-(2-Amino-4-methyl-thiazol-5-yl)-pyrimidin-2-yl]-(4-methanesulfonyl-phenyl)-amine [76]. By condensation of N'-[5-(3-dimethylamino-acryloyl)-4-methyl-thiazol-2-yl]-N,N-dimethyl-formamidine and N-(4-methanesulfonyl-phenyl)-guanidine nitrate. Yellow solid. Anal. RP-HPLC: $t_R$=13.2 min (0-60% MeCN, purity >97%). $^1$H-NMR (DMSO-d$_6$) δ: 1.98 (s, 3H, CH$_3$), 2.54 (s, 3H, CH$_3$), 7.06 (d, 1H, J=5.5 Hz, pyrimidinyl-H), 7.80 (m, 2H, Ph-H), 8.00 (m, 2H, Ph-H), 8.45 (d, 1H, J=5.5 Hz, pyrimidinyl-H), 10.05 (sbr, 2H, NH$_2$). MS (ESI$^+$) m/z 362.38 [M+H]$^+$ (C$_{15}$H$_{15}$N$_5$O$_2$S$_2$ requires 361.44).

[4-(2-Methoxy-ethoxy)-3-nitro-phenyl]-[4-(4-methyl-2-methylamino-thiazol-5-yl)-pyrimidin-2-yl]-amine [77]. By alkylation of [4-(2-aminomethyl-4-methyl-thiazol-5-yl)-pyrimidin-2-yl]-(4-fluoro-3-nitrophenyl)-amine with 2-methoxy-ethanol. Yellow solid. Anal. RP-HPLC: $t_R$=12.8 min (10-70% MeCN, purity >90%). $^1$H-NMR (DMSO-D$_6$) δ: 2.41 (s, 3H, CH$_3$), 2.86 (d, 3H, J=4.5 Hz, CH$_3$), 3.24 (s, 3H, CH$_3$), 3.66 (m, 2H, CH$_2$), 4.23 (m, 2H, CH$_2$), 6.93 (d, 1H, J=6.0 Hz, pyrimidinyl-H), 7.32 (d, 1H, J=5.0 Hz, Ph-H), 7.79 (m, 1H, Ph-H), 8.08 (d, 1H, J=5.0 Hz, Ph-H), 8.35 (d, 1H, J=5.0 Hz, pyrimidinyl-H), 8.54 (m, 1H, NH), 9.68 (s, 1H, NH). MS (ESI$^+$) m/z 417.08 [M+H]$^+$ (C$_{18}$H$_{20}$N$_6$O$_4$S requires 416.46).

[4-(2,4-Dimethyl-thiazol-5-yl)-pyrimidin-2-yl]-[3-(2-morpholin-4-yl-ethoxymethyl)-phenyl]-amine [81]. By alkylation of {3-[4-(2,4-dimethyl-thiazol-5-yl)-pyrimidin-2- ylamino]-phenyl}-methanol with 4-(2-chloro-ethyl)-morpholine. Yellow solid. Anal. RP-HPLC: $t_R$=8.5 min (10-70% MeCN, purity >95%). $^1$H-NMR (DMSO-D$_6$) δ: 2.56 (s, 3H, CH$_3$), 2.57 (s, 3H, CH$_3$), 2.63 (m, 2H, CH2), 3.58 (m, 4H, J=4.5 Hz, CH$_2$×2), 4.14 (t, 2H, J=7.5 Hz, CH$_2$), 4.58 (d, 2H, J=5.0 Hz, CH$_2$), 5.28 (t, 1H, J=5.5 Hz, NH), 7.06 (d, 1H, J=5.5 Hz, pyrimidinyl-H), 7.26 (m, 2H, Ph-H), 7.36 (s, 1H, Ph-H), 7.42 (m, 1H, Ph-H), 8.43 (d, 1H, J=5.5 Hz, pyrimidinyl-H), 9.12 (sbr, 1H, Ph-H). MS (ESI$^+$) m/z 426.46 [M+H]$^+$ (C$_{22}$H$_{27}$N$_5$O$_2$S requires 425.55).

C,C,C-Trifluoro-N-{3-[4-(4-methyl-2-methylamino-thiazol-5-yl)-pyrimidin-2-ylamino]-benzyl}-methanesulfonamide [82]. By treatment of (3-aminomethyl-phenyl)-[4-(4-methyl-2-methylamino-thiazol-5-yl)-pyrimidin-2-yl]-amine with trifluoro-methanesulfonyl chloride. Yellow solid. Anal. RP-HPLC: $t_R$=11.6 min (0-60% MeCN, purity ~90%). $^1$H-NMR (CD$_3$OD) δ: 2.53 (s, 3H, CH$_3$), 2.97 (s, 3H, CH$_3$), 4.39 (s, 2H, CH$_2$), 6.94 (d, 1H, J=5.5 Hz, pyrimidinyl-H), 7.01 (d, 1H, J=7.5 Hz, Ph-H), 7.31 (d, 1H, J=8.0 Hz, Ph-H), 7.60 (d, 1H, J=7.5 Hz, Ph-H), 7.67 (s, 1H, Ph-H), 8.28 (d, 1H, J=5.5 Hz, pyrimidinyl-H). MS (ESI$^+$) m/z 459.33 [M+H]$^+$ (C$_{17}$H$_{17}$F$_3$N$_6$O$_2$S requires 458.48).

N-{3-[4-(4-Methyl-2-methylamino-thiazol-5-yl)-pyrimidin-2-ylamino]-benzyl}-methanesulfonamide [83]. By treatment of (3-aminomethyl-phenyl)-[4-(4-methyl-2-methylamino-thiazol-5-yl)-pyrimidin-2-yl]-amine with methanesulfonyl chloride. Yellow solid. Anal. RP-HPLC: $t_R$=12.8 min (0-60% MeCN, purity >95%). $^1$H-NMR (CD$_3$OD) δ: 2.53 (s, 3H, CH$_3$), 2.88 (s, 3H, CH$_3$), 2.98 (s, 3H, CH$_3$), 4.28 (s, 2H, CH$_2$), 6.94 (d, 1H, J=5.5 Hz, pyrimidinyl-H), 7.02 (d, 1H, J=7.5 Hz, Ph-H), 7.29 (t, 1H, J=8.0 Hz, Ph-H), 7.52 (d, 1H, J=8.0 Hz, Ph-H), 7.90 (s, 1H, Ph-H), 7.98 (s, 1H, NH), 8.28 (d, 1H, J=5.5 Hz, pyrimidinyl-H).

[4-(2-Amino-4-methyl-thiazol-5-yl)-pyrimidin-2-yl]-(3-methanesulfonyl-phenyl)-amine [84]. By condensation of N'-[5-(3-dimethylamino-acryloyl)-4-methyl-thiazol-2-yl]-N,N-dimethyl-formamidine and N-(3-methanesulfonyl-phenyl)-guanidine nitrate. Yellow solid. Anal. RP-HPLC: $t_R$=13.1 min (0-60% MeCN, purity >97%). $^1$H-NMR (DMSO-d$_6$) δ: 2.55 (s, 3H, CH$_3$), 3.19 (s, 3H, CH$_3$), 6.97 (d, 1H, J=5.5 Hz, pyrimidinyl-H), 7.47 (m, 1H, Ph-H), 7.54 (t, 1H, J=7.5 Hz, Ph-H), 8.08 (m, 1H, Ph-H), 8.34 (brs, 1H, Ph-H), 8.40 (d, 1H, J=5.5 Hz, pyrimidinyl-H), 9.86 (sbr, 2H, NH$_2$). MS (ESI$^+$) m/z 362.38 [M+H]$^+$ (C$_{15}$H$_{15}$N$_5$O$_2$S$_2$ requires 361.44).

[4-(2,4-Dimethyl-thiazol-5-yl)-pyrimidin-2-yl]-(4-methanesulfonyl-phenyl)-amine [85]. By condensation of 3-dimethylamino-1-(2,4-dimethyl-thiazol-5-yl)-propenone and N-(4-methanesulfonyl-phenyl)-guanidine nitrate. Yellow solid. Anal. RP-HPLC: $t_R$=16.6 min (0-60% MeCN, purity >97%). $^1$H-NMR (DMSO-d$_6$) δ: 2.65 (s, 3H, CH$_3$), 2.66 (s, 3H, CH$_3$), 3.15 (s, 3H, CH$_3$), 7.22 (d, 1H, J=5.5 Hz, pyrimidinyl-H), 7.84 (d, 2H, J=9.0 Hz, Ph-H), 8.03 (d, 2H, J=9.0 Hz, Ph-H), 8.61 (d, 1H, J=5.5 Hz, pyrimidinyl-H), 10.23 (sbr, 1H, NH). MS (ESI$^+$) m/z 361.17 [M+H]$^+$ (C$_{16}$H$_{16}$N$_4$O$_2$S$_2$ requires 361.46).

3,4-Dimethyl-5-[2-(4-morpholin-4-yl-phenylamino)-pyrimidin-4-yl]-3H-thiazol-2-one [92].

Methylammonium N-methylthio-carbamate (13.1 g, 0.105 mol; prepared from methylamine and carbonyl sulfide as described, Y. Gelernt et al. 1974, J. Chem. Soc. Perkin Trans. 1, 2610) was partially dissolved in MeOH (150 mL). 3-Chloro-pentane-2,4-dione (14.9 mL, 0.125 mol) was added drop-wise at room temperature, producing a gradual exotherm to 40° C. After stirring at room temperature for 1 h, the solvent was removed in vacuo. The residue was treated with H$_2$O (50 mL) and was extracted with CH$_2$Cl$_2$ (3×50 mL). The combined organic fractions were washed (brine), dried (Na$_2$SO$_4$), filtered, and evaporated in vacuo to an amber-coloured oil. This was purified by chromatography (300 g SiO$_2$, eluting with 1:1 heptane/Et$_2$O to obtain non-cyclized adduct, then Et$_2$O to obtain 5-acetyl-3,4-dimethyl-3H-thiazol-2-one, which was recrystallized from EtOH as colourless needles (14.2 g). $^1$H-NMR (CDCl$_3$): δ 2.34 (s, 3H), 2.59 (s, 3H), 3.33 (s, 3H). IR (ATR): 1655 and 1621 cm$^{-1}$ (CO str).

5-Acetyl-3,4-dimethyl-3H-thiazol-2-one (4.64 g, 27.10 mmol) and dimethylformamide dimethyl acetal (8.4 mL, 59.62 mmol) were mixed in a dry, argon-flushed flask, and heated at 100° C. for 3 h. The mixture was cooled, producing some precipitation, which was enhanced by the addition of an equal volume of Et$_2$O. The resulting orange solid was filtered and washed with Et$_2$O to give 2.73 g of 5-(3-dimethylamino-acryloyl)-3,4-dimethyl-3H-thiazol-2-one. $^1$H-NMR (d$_6$-DMSO): δ: 2.52 (s, 3H), 2.82 (bs, 3H), 3.11 (bs, 3H), 3.22 (s, 3H), 5.10 (d, 1H, J=12.2 Hz), 7.61 (d, 1H, J=11.7 Hz). IR (ATR): 1669 and 1630 cm$^{-1}$ (CO str).

Condensation between 5-(3-dimethylamino-acryloyl)-3,4-dimethyl-3H-thiazol-2-one and N-(4-morpholin-4-yl-phenyl)-guanidine nitrate afforded the title compound. Anal. RP-HPLC: $t_R$=17.5 min (0-60% MeCN in 0.1% aq CF$_3$COOH over 20 min, 1 mL/min, purity >95%). $^1$H-NMR (DMSO-d$_6$) δ: 2.48 (3H, s, CH$_3$), 3.03 (4H, m, 2×morph-NCH$_2$), 3.08 (3H, s, CH$_3$), 3.72 (4H, m, 2×morph-OCH$_2$), 6.85 (1H, d, J=5.2, pyrim-H), 6.89 (2H, d, J=9.2, 2×ArH), 7.57 (2H, d, J=9.2, 2×ArH), 8.36 (1H, d, J=5.2, pyrim-H) and 9.35 (1H, s, NH). MS (ESI$^+$) m/z 384[M+H]$^+$ (C$_{19}$H$_{21}$N$_5$O$_2$S requires 383.5).

3,4-Dimethyl-5-{2-[4-(4-methyl-piperazin-1-yl)-phenylamino]-pyrimidin-4-yl}-3H-thiazol-2-one [93]. This compound was prepared by condensation between 5-(3-dimethylamino-acryloyl)-3,4-dimethyl-3H-thiazol-2-one and N-[4-(4-methyl-piperazin-1-yl)-phenyl]-guanidine nitrate. Pale solid. Anal. RP-HPLC: $t_R$=10.9 min (0-60% MeCN in 0.1% aq CF$_3$COOH over 20 min, 1 mL/min, purity >97%). $^1$H-NMR (CDCl$_3$) δ: 2.42 (m, 4H, CH$_2$), 2.53 (s, 3H, CH$_3$), 3.04 (m, 4H, CH$_2$), 3.28 (s, 3H, CH$_3$), 6.84 (d, 1H, J=5.5 Hz, pyrimidinyl-H), 6.86 (d, 2H, J=9.0 Hz, Ph-H), 7.54 (d, 2H, J=9.0 Hz, Ph-H), 8.35 (d, 1H, J=5.5 Hz, pyrimidinyl-H), and 9.33 (s, 1H, NH).

Example 3

Kinase assays. The compounds from Example 2 above were investigated for their ability to inhibit the enzymatic activity of various protein kinases. This was achieved by measurement of incorporation of radioactive phosphate from ATP into appropriate polypeptide substrates. Recombinant protein kinases and kinase complexes were produced or obtained commercially. Assays were performed using 96-well plates and appropriate assay buffers (typically 25 mM β-glycerophosphate, 20 mM MOPS, 5 mM EGTA, 1 mM DTT, 1 mM Na$_3$VO$_3$, pH 7.4), into which were added 2-4 μg of active enzyme with appropriate substrates. The reactions were initiated by addition of Mg/ATP mix (15 mM MgCl$_2$+ 100 μM ATP with 30-50 kBq per well of [γ-$^{32}$P]-ATP) and mixtures incubated as required at 30° C. Reactions were stopped on ice, followed by filtration through p81 filterplates or GF/C filterplates (Whatman Polyfiltronics, Kent, UK). After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine $IC_{50}$ values (concentration of test compound which inhibits kinase activity by 50%).

CDK 7 and 9 assays. CTD peptide substrate (biotinyl-Ahx-(Tyr-Ser-Pro-Thr-Ser-Pro-Ser)$_4$-NH$_2$; 1-2 μg/mL) and recombinant human CDK7/cyclin H, CDK9/cyclin T1, or CDK9/cyclin K (0.5-2 μg) were incubated for 45 min at 30° C. in the presence of varying amounts of test compound in 20 mM MOPS pH 7.2, 25 mM β-glycerophosphate, 5 mM EGTA, 1 mM DTT, 1 mM sodium vanadate, 15 mM MgCl$_2$, and 100 μM ATP (containing a trace amount of $^{32}$PγATP) in a total volume of 25 μL in a 96-well microtiter plate. The reaction was stopped by placing the plate on ice for 2 min. Avidin (50 μg) was added to each well, and the plate was incubated at room temp for 30 min. The samples were transferred to a 96-well P81 filter plate, and washed (4×200 μL per well) with 75 mM phosphoric acid. Microscint 40 scintillation liquid (50 μL) was added to each well, and the amount of $^{32}$P incorporation for each sample was measured using a Packard Topcount microplate scintillation counter.

Aurora-A (human) kinase assay. This was achieved by measurement of incorporation of radioactive phosphate from ATP into Kemptide substrate (LRRASLG), upon phosphorylation by commercially obtained aurora-A kinase. Assays were performed using 96-well plates and appropriate assay buffers (8 mM MOPS, 0.2 mM EDTA, pH 7.0), into which were added 5-10 ng of active enzyme with 200 μM substrate (Kemptide). The reactions were initiated by addition of Mg/ATP mix (10 mM MgAcetate+15 μM ATP with 30-50 kBq per well of [γ-$^{33}$P]-ATP) and mixtures incubated for 40 min at room temperature. Reactions were stopped by addition of 3% phosphoric acid, followed by filtration through p81 filterplates (Whatman Polyfiltronics, Kent, UK). After washing 5 times with 75 mM aq orthophosphoric acid and once in methanol, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 2.0.9, IDBS, Guildford, Surrey, UK) to determine $IC_{50}$ values (concentration of test compound which inhibits kinase activity by 50%).

Results are summarized in Table 2 and a more extensive kinase selectivity panel for selected compounds is shown in Table 3.

Example 4

MTT cytotoxicity assay. The compounds from Example 2 were subjected to a standard cellular proliferation assay using human tumour cell lines obtained from the ATCC (American Type Culture Collection, 10801 University Boulevard, Manassas, Va. 20110-2209, USA). Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R.; Vaillant, F.; Wang, Z. X.; Hertzog, P. J. Biochemistry International 1992, 27, 501-10). In short: cells were seeded into 96-well plates according to doubling time and incubated overnight at 37° C. Test compounds were made up in DMSO and a ⅓ dilution series prepared in 100 μL cell media, added to cells (in triplicates) and incubated for 72 ho at 37° C. MTT was made up as a stock of 5 mg/mL in cell media and filter-sterilised. Media was removed from cells followed by a wash with 200 μL PBS. MTT solution was then added at 20 μL per well and incubated in the dark at 37° C. for 4 h. MTT solution was removed and cells again washed with 200 μL PBS. MTT dye was solubilised with 200 μL per well of DMSO with agitation. Absorbance was read at 540 nm and data analysed using curve-fitting software (GraphPad Prism version 3.00 for Windows, GraphPad Software, San Diego Calif. USA) to determine $IC_{50}$ values (concentration of test compound which inhibits cell growth by 50%). Results are summarized in Table 4 and more extensive data for selected compounds is presented in Table 5.

Example 5

Anti-HIV Efficacy Evaluation in Fresh Human PBMCs

Representative compounds of the present invention were tested for antiviral activity against HIV-1 in human peripheral blood mononuclear cells (PBMCs) using the clinical pediatric HIV strain RoJo or WeJo. PBMCs were cultured under conditions which promote cell survival and HIV replication. Antiviral activity was tested for from 6-9 $\log_{10}$ serial dilutions of a 100 μM compound stock solution in DMSO. The following parameters were derived: $IC_{50}$ and $IC_{90}$ (concentrations inhibiting virus replication by 50 and 90%, respectively, $TC_{50}$ (concentration decreasing cell viability by 50%), and TI (therapeutic index: $TC_{50}/IC_{50}$).

Fresh PBMCs, seronegative for HIV and HBV, were isolated from screened donors (Interstate Blood Bank, Inc. Memphis, Tenn.). Cells were pelleted/washed 2-3 times by low speed centrifugation and re-suspension in PBS to remove contaminating platelets. The Leukophoresed blood was then diluted with Dulbecco's Phosphate Buffered Saline (DPBS) and layered over Lymphocyte Separation Medium (LSM; Cellgro® by Mediatech, Inc.; density 1.078±0.002 g/mL; Cat. #85-072-CL) in a 50 mL centrifuge tube and then centrifuged. Banded PBMCs were gently aspirated from the resulting interface and subsequently washed with PBS by low speed centrifugation. After the final wash, cells were enumerated by trypan blue exclusion and re-suspended in RPMI 1640 supplemented with fetal bovine serum (FBS), and L-glutamine, Phytohemagglutinin (PHA-P, Sigma). The cells were allowed to incubate at 37° C. After incubation, PBMCs were centrifuged and resuspended in RPMI 1640 with FBS, L-glutamine, penicillin, streptomycin, gentamycin, and recombinant human IL-2 (R&D Systems, Inc). IL-2 is included in the culture medium to maintain the cell division initiated by the PHA mitogenic stimulation. PBMCs were maintained in this with bi-weekly medium changes until used in the assay protocol. Cells were kept in culture for a maximum of two weeks before being deemed too old for use in assays and discarded. Monocytes were depleted from the culture as the result of adherence to the tissue culture flask.

For the standard PBMC assay, PHA-P stimulated cells from at least two normal donors were pooled, diluted and plated in the interior wells of a 96-well round bottom microplate. Pooling of mononuclear cells from more than one donor was used to minimise the variability observed between individual donors, which results from quantitative and qualitative differences in HIV infection and overall response to the PHA and IL-2 of primary lymphocyte populations. Each plate contained virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared in microtiter tubes and each concentration was placed in appropriate wells using the standard format. A predetermined dilution of virus stock was placed in each test well (final MOI≅0.1). The PBMC cultures were maintained for seven days following infection at 37° C., 5% $CO_2$. After this period, cell-free supernatant samples were collected for analysis of reverse transcriptase activity and/or HIV p24 content. Following removal of supernatant samples, compound cytotoxicity was measured by addition of MTS to the plates for determination of cell viability. Wells were also examined microscopically and any abnormalities were noted.

Reverse transcriptase activity assay: A microtiter plate-based reverse transcriptase (RT) reaction was utilised (Buckheit et al., AIDS Research and Human Retroviruses 7:295-302, 1991). Tritiated thymidine triphosphate ($^3$H-TTP, 80 Ci/mmol, NEN) was received in 1:1 $dH_2O$:Ethanol at 1 mCi/mL. Poly rA:oligo dT template:primer (Pharmacia) was prepared as a stock solution, followed by aliquoting and storage at −20° C. The RT reaction buffer was prepared fresh on a daily basis. The final reaction mixture was prepared by combining $^3$H-TTP, $dH_2O$, poly rA:oligo dT stock and reaction buffer. This reaction mixture was placed in a round bottom microtiter plate and supernatant containing virus was added and mixed. The plate was incubated at 37° C. for 60 minutes. Following incubation, the reaction volume was spotted onto DE81 filter-mats (Wallac), in a sodium phosphate buffer or 2×SSC (Life Technologies). Next they were washed in distilled water, in 70% ethanol, and then dried. Incorporated radioactivity (counts per minute, CPM) was quantified using standard liquid scintillation techniques. The results for selected compounds of the invention are shown below in Table 6.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Example compounds

| No. | Structure | Name |
| --- | --- | --- |
| 1 | 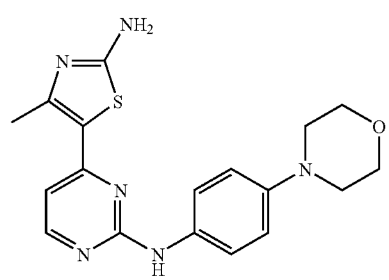 | [4-(2-Amino-4-methyl-thiazol-5-yl)-pyrimidin-2-yl]-(4-morpholin-4-yl-phenyl)-amine |
| 2 | 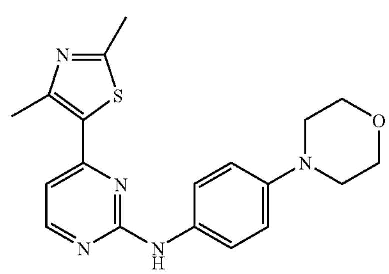 | [4-(2,4-Dimethyl-thiazol-5-yl)-pyrimidin-2-yl]-(4-morpholin-4-yl-phenyl)-amine |
| 3 | 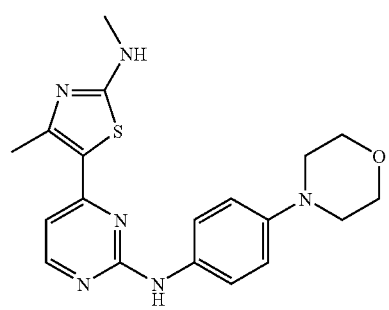 | [4-(2-N-Methylamino-4-methyl-thiazol-5-yl)-pyrimidin-2-yl]-(4-morpholinophenyl)-amine |

TABLE 1-continued

| No. | Structure | Name |
| --- | --- | --- |
| 4 | 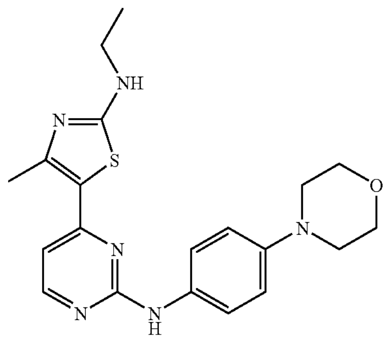 | [4-(2-Ethylamino-4-methyl-thiazol-5-yl)-pyrimidin-2-yl]-(4-morpholin-4-yl-phenyl)-amine |
| 5 | 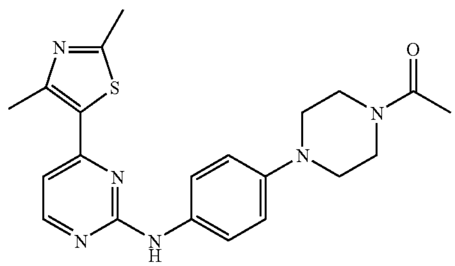 | 1-(4-{4-[4-(2,4-Dimethyl-thiazol-5-yl)-pyrimidin-2-ylamino]-phenyl}-piperazin-1-yl)-ethanone |
| 6 | 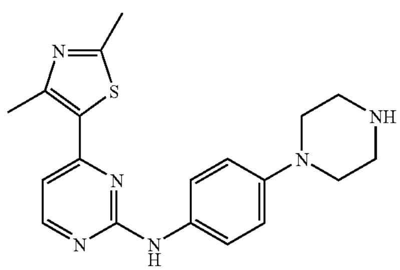 | [4-(2,4-Dimethyl-thiazol-5-yl)-pyrimidin-2-yl]-(4-piperazin-1-yl-phenyl)-amine |
| 7 | 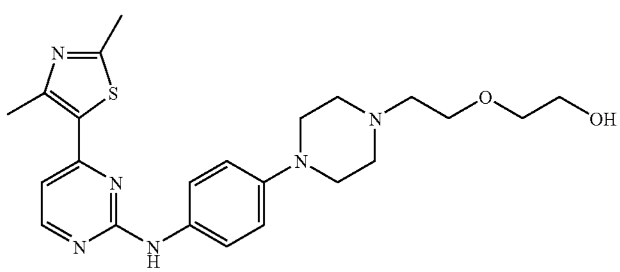 | [4-(2,4-Dimethyl-thiazol-5-yl)-pyrimidin-2-yl]-[4-(4'-2''-ethoxyethanolpiperazino)-phenyl]-amine |
| 8 | 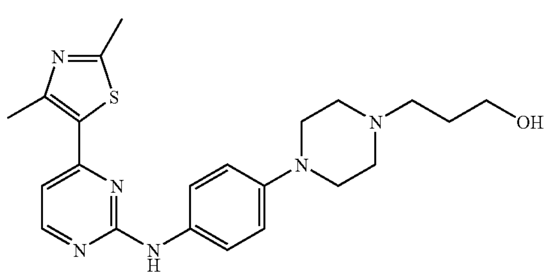 | 3-(4-{4-[4-(2,4-Dimethyl-thiazol-5-yl)-pyrimidin-2-ylamino]-phenyl}-piperazin-1-yl)-propan-1-ol |

TABLE 1-continued

Example compounds

| No. | Structure | Name |
| --- | --- | --- |
| 9 | 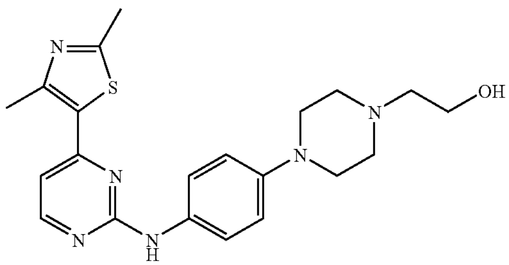 | 2-(4-{4-[4-(2,4-Dimethyl-thiazol-5-yl)-pyrimidin-2-ylamino]-phenyl}-piperazin-1-yl)-ethanol |
| 10 | 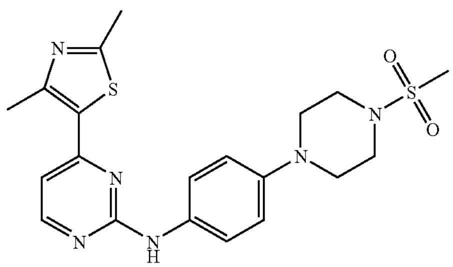 | [4-(2,4-Dimethyl-thiazol-5-yl)-pyrimidin-2-yl]-[4-(4-methanesulfonyl-piperazin-1-yl)-phenyl]-amine |
| 11 | 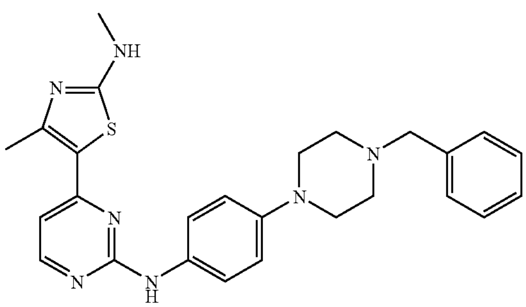 | [4-(4-Benzyl-piperazin-1-yl)-phenyl]-[4-(4-methyl-2-methylamino-thiazol-5-yl)-pyrimidin-2-yl]-amine |
| 12 | 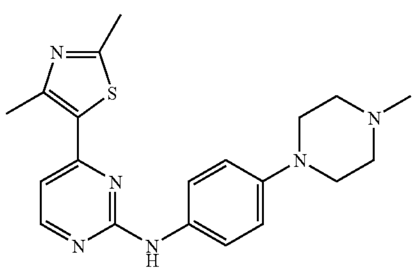 | [4-(2,4-Dimethyl-thiazol-5-yl)-pyrimidin-2-yl]-[4-(4-methyl-piperazin-1-yl)-phenyl]-amine |
| 13 | 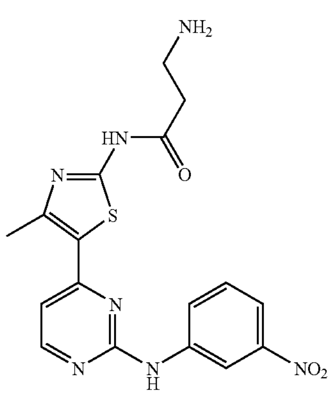 | 3-Amino-N-{4-methyl-5-[2-(3-nitro-phenylamino)-pyrimidin-4-yl]-thiazol-2-yl}-propionamide |

TABLE 1-continued

| No. | Structure | Name |
|---|---|---|
| 14 | 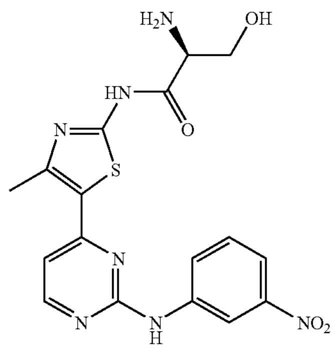 | (2S)-2-Amino-3-hydroxy-N-{4-methyl-5-[2-(3-nitro-phenylamino)-pyrimidin-4-yl]-thiazol-2-yl}-propionamide |
| 15 | 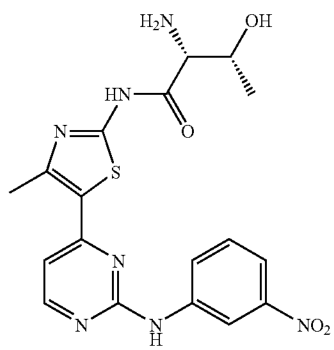 | (2R,3R)-2-Amino-3-hydroxy-N-{4-methyl-5-[2-(3-nitro-phenylamino)-pyrimidin-4-yl]-thiazol-2-yl}-butyramide |
| 16 | 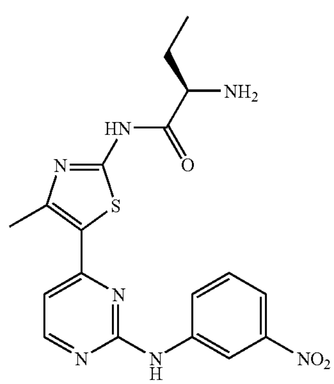 | (2R)-2-Amino-N-{4-methyl-5-[2-(3-nitro-phenylamino)-pyrimidin-4-yl]-thiazol-2-yl}-butyramide |
| 17 | 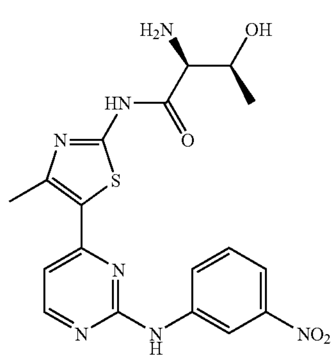 | (2S,3S)-2-Amino-3-hydroxy-N-{4-methyl-5-[2-(3-nitro-phenylamino)-pyrimidin-4-yl]-thiazol-2-yl}-butyramide |

TABLE 1-continued

Example compounds

| No. | Structure | Name |
| --- | --- | --- |
| 18 | 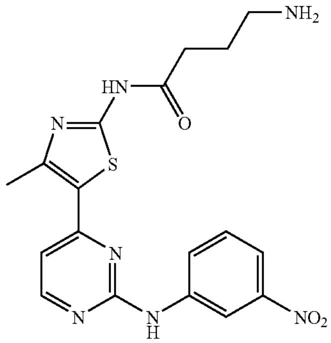 | 4-Amino-N-{4-methyl-5-[2-(3-nitro-phenylamino)-pyrimidin-4-yl]-thiazol-2-yl}-butyramide |
| 19 | 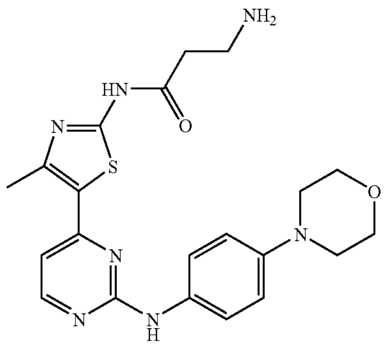 | 3-Amino-N-{4-methyl-5-[2-(4-morpholin-4-yl-phenylamino)-pyrimidin-4-yl]-thiazol-2-yl}-propionamide |
| 20 | 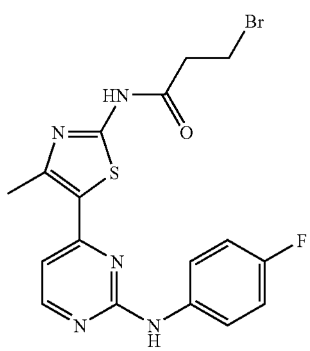 | 3-Bromo-N-{5-[2-(4-fluoro-phenylamino)-pyrimidin-4-yl]-4-methyl-thiazol-2-yl}-propionamide |
| 21 | 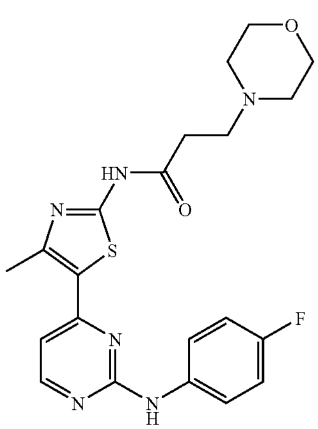 | N-{5-[2-(4-Fluoro-phenylamino)-pyrimidin-4-yl]-4-methyl-thiazol-2-yl}-3-morpholin-4-yl-propionamide |

TABLE 1-continued
| No. | Structure | Name |
|---|---|---|
| 22 | 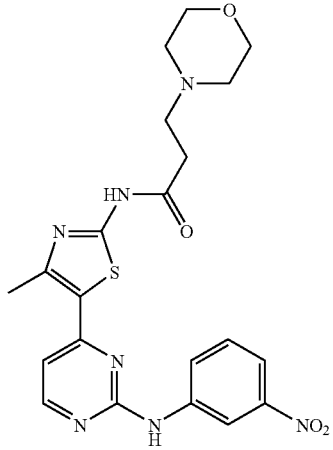 | N-{4-Methyl-5-[2-(3-nitro-phenylamino)-pyrimidin-4-yl]-thiazol-2-yl}-3-morpholin-4-yl-propionamide |
| 23 | 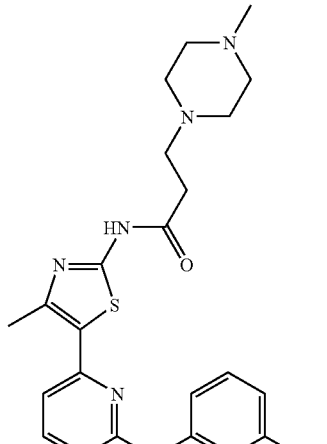 | N-{4-Methyl-5-[2-(3-nitro-phenylamino)-pyrimidin-4-yl]-thiazol-2-yl}-3-(4-methyl-piperazin-1-yl)-propionamide |
| 24 | 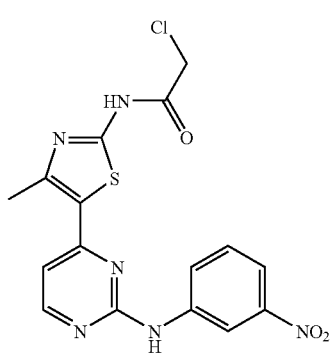 | 2-Chloro-N-{4-methyl-5-[2-(3-nitro-phenylamino)-pyrimidin-4-yl]-thiazol-2-yl}-acetamide |

TABLE 1-continued

Example compounds

| No. | Structure | Name |
|---|---|---|
| 25 | 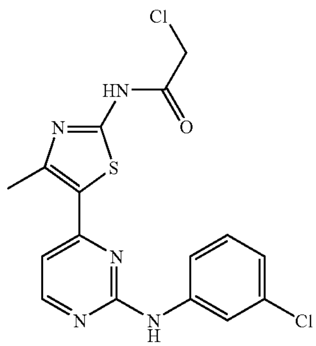 | 2-Chloro-N-{5-[2-(3-chloro-phenylamino)-pyrimidin-4-yl]-4-methyl-thiazol-2-yl}-acetamide |
| 26 | 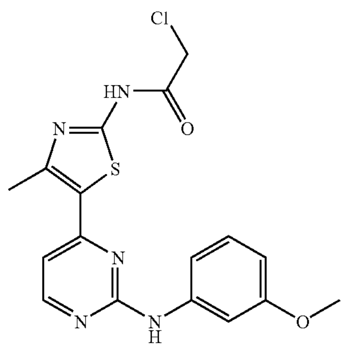 | 2-Chloro-N-{5-[2-(3-methoxy-phenylamino)-pyrimidin-4-yl]-4-methyl-thiazol-2-yl}-acetamide |
| 27 | 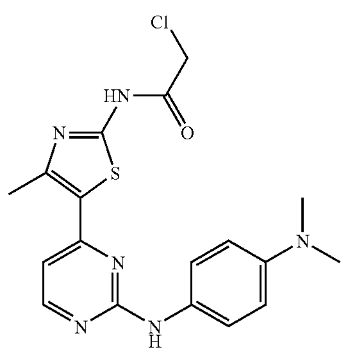 | 2-Chloro-N-{5-[2-(4-dimethylamino-phenylamino)-pyrimidin-4-yl]-4-methyl-thiazol-2-yl}-acetamide |
| 28 | 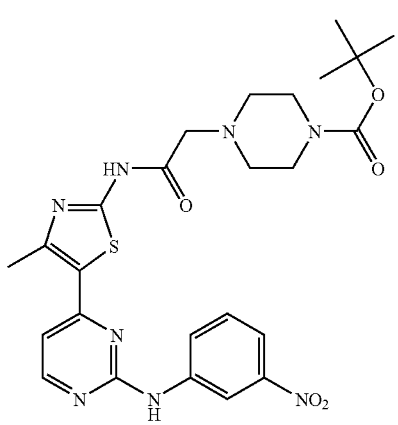 | 4-({4-Methyl-5-[2-(3-nitro-phenylamino)-pyrimidin-4-yl]-thiazol-2-ylcarbamoyl}-methyl)-piperazine-1-carboxylic acid tert-butyl ester |

TABLE 1-continued

Example compounds

| No. | Structure | Name |
|---|---|---|
| 29 | 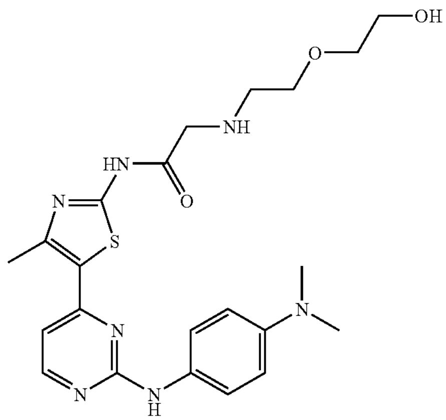 | N-{5-[2-(4-Dimethylamino-phenylamino)-pyrimidin-4-yl]-4-methyl-thiazol-2-yl}-2-[2-(2-hydroxy-ethoxy)-ethylamino]-acetamide |
| 30 | 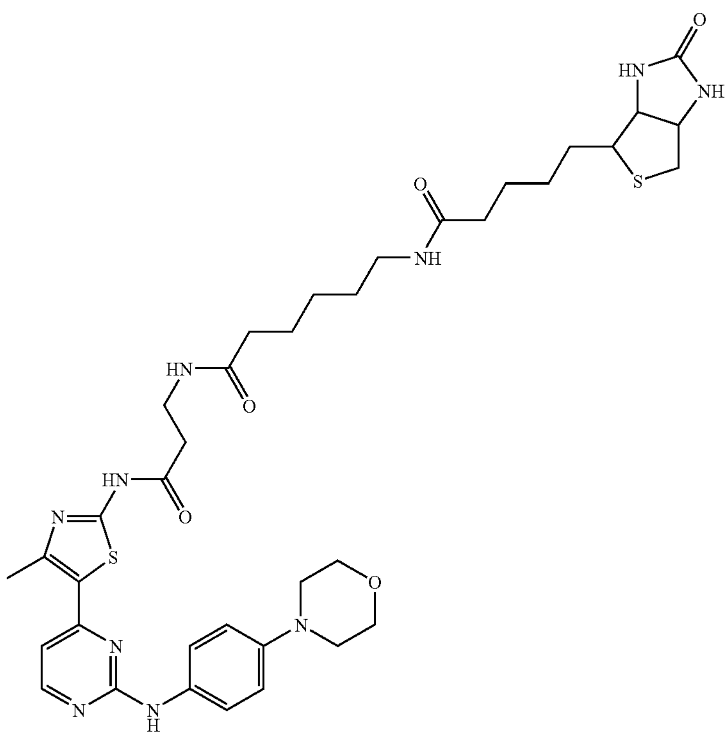 | 6-[5-(2-Oxo-hexahydro-thieno[3,4-d]imidazol-4-yl)-pentanoylamino]-hexanoic acid (2-{4-methyl-5-[2-(4-morpholin-4-yl-phenylamino)-pyrimidin-4-yl]thiazol-2-ylcarbamoyl}-ethyl)-amide |
| 31 | 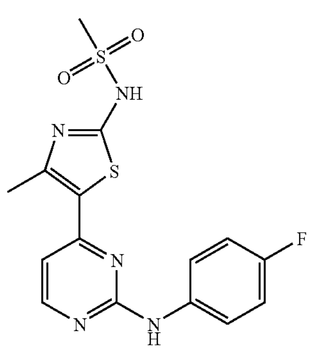 | N-{5-[2-(4-Fluoro-phenylamino)-pyrimidin-4-yl]-4-methyl-thiazol-2-yl}-methanesulfonamide |

TABLE 1-continued

Example compounds

| No. | Structure | Name |
|---|---|---|
| 32 | 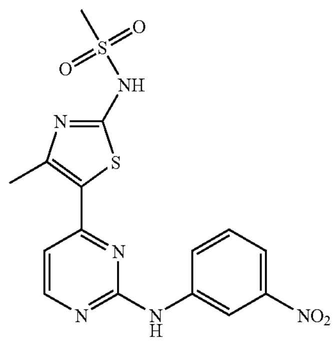 | N-{4-Methyl-5-[2-(3-nitro-phenylamino)-pyrimidin-4-yl]-thiazol-2-yl}-methane sulfonamide |
| 33 | 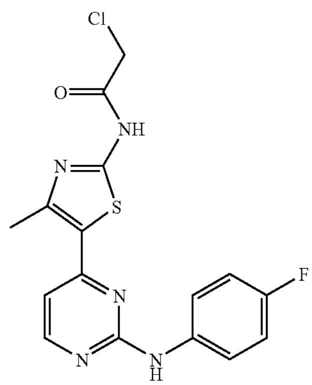 | 2-Chloro-N-{5-[2-(4-fluoro-phenylamino)-pyrimidin-4-yl]-4-methyl-thiazol-2-yl}-acetamide |
| 34 | 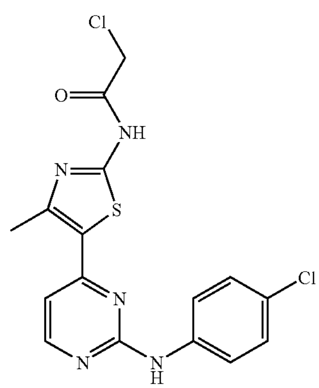 | 2-Chloro-N-{5-[2-(4-chloro-phenylamino)-pyrimidin-4-yl]-4-methyl-thiazol-2-yl}-acetamide |
| 35 | 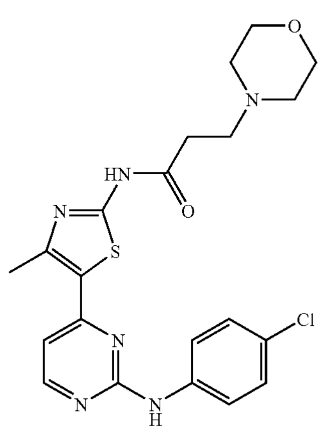 | N-{5-[2-(4-Chloro-phenylamino)-pyrimidin-4-yl]-4-methyl-thiazol-2-yl}-3-morpholin-4-yl-propionamide |

TABLE 1-continued
Example compounds
| No. | Structure | Name |
|---|---|---|
| 36 | 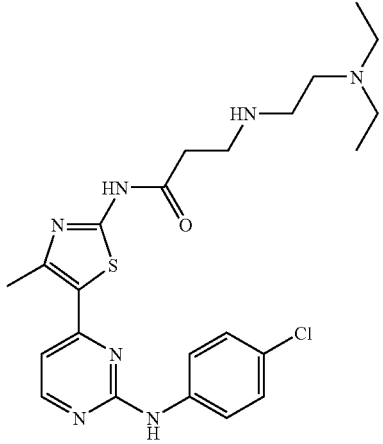 | N-{5-[2-(4-Chloro-phenylamino)-pyrimidin-4-yl]-4-methyl-thiazol-2-yl}-3-(2-diethylamino-ethylamino)-propionamide |
| 37 | 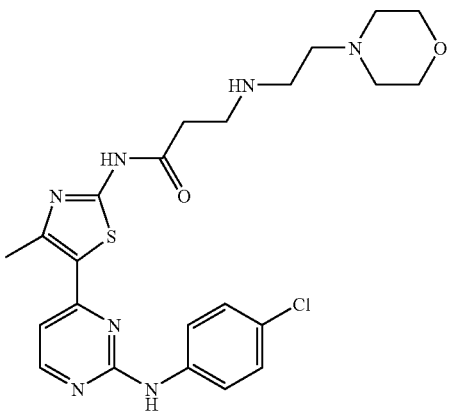 | N-{5-[2-(4-Chloro-phenylamino)-pyrimidin-4-yl]-4-methyl-thiazol-2-yl}-3-(2-morpholin-4-yl-ethylamino)-propionamide |
| 38 | 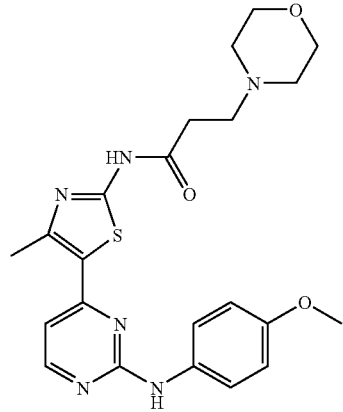 | N-{5-[2-(4-Methoxy-phenylamino)-pyrimidin-4-yl]-4-methyl-thiazol-2-yl}-3-morpholin-4-yl-propionamide |

TABLE 1-continued
| No. | Structure | Name |
|---|---|---|
| 39 | 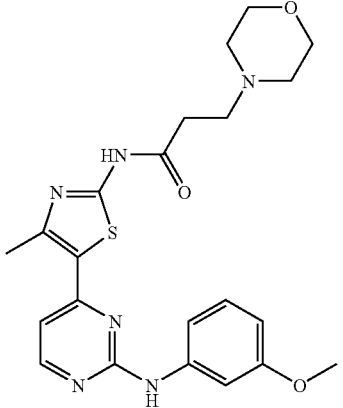 | N-{5-[2-(3-Methoxy-phenylamino)-pyrimidin-4-yl]-4-methyl-thiazol-2-yl}-3-morpholin-4-yl-propionamide |
| 40 | 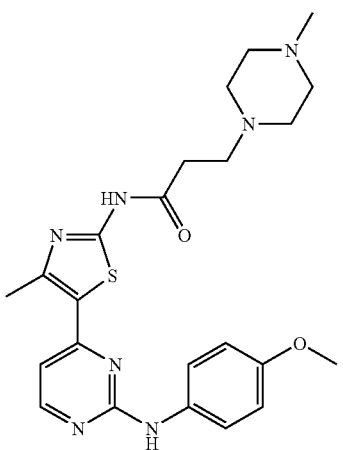 | N-{5-[2-(4-Methoxy-phenylamino)-pyrimidin-4-yl]-4-methyl-thiazol-2-yl}-3-(4-methyl-piperazin-1-yl)-propionamide |
| 45 | 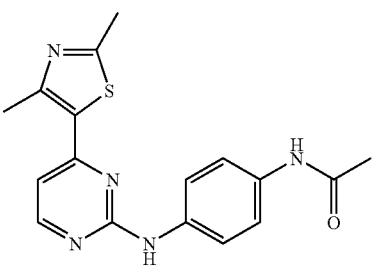 | N-{4-[4-(2,4-Dimethyl-thiazol-5-yl)-pyrimidin-2-ylamino]-phenyl}-acetamide |
| 48 | 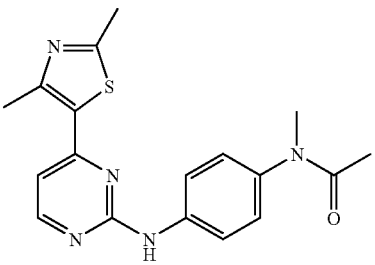 | N-{4-[4-(2,4-Dimethyl-thiazol-5-yl)-pyrimidin-2-ylamino]-phenyl}-N-methyl-acetamide |

TABLE 1-continued

Example compounds

| No. | Structure | Name |
|---|---|---|
| 49 | 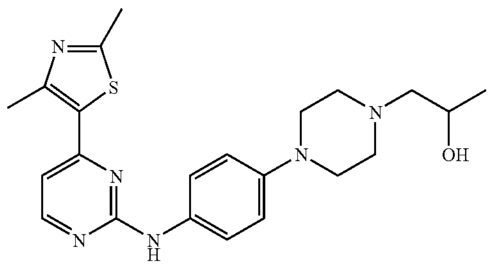 | 1-(4-{4-[4-(2,4-Dimethyl-thiazol-5-yl)-pyrimidin-2-ylamino]-phenyl}-piperazin-1-yl)-propan-2-ol |
| 50 | 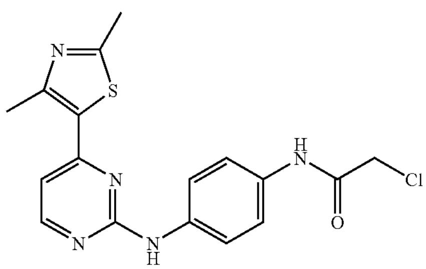 | 2-Chloro-N-{4-[4-(2,4-dimethyl-thiazol-5-yl)-pyrimidin-2-ylamino]-phenyl}-acetamide |
| 51 | 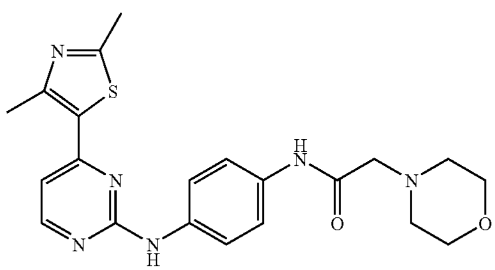 | N-{4-[4-(2,4-Dimethyl-thiazol-5-yl)-pyrimidin-2-ylamino]-phenyl}-2-morpholin-4-yl-acetamide |
| 52 | 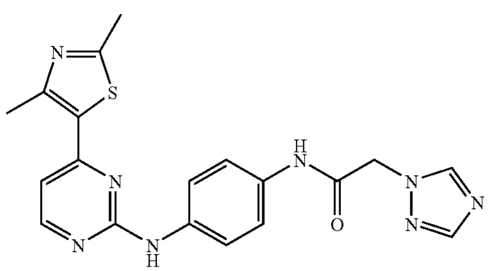 | N-{4-[4-(2,4-Dimethyl-thiazol-5-yl)-pyrimidin-2-ylamino]-phenyl}-2-[1,2,4]triazol-1-yl-acetamide |
| 53 | 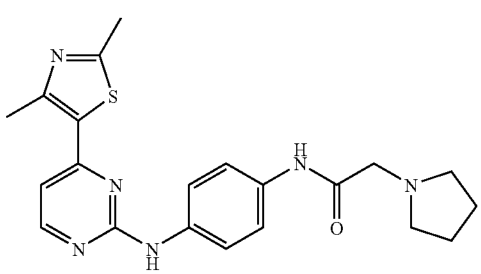 | N-{4-[4-(2,4-Dimethyl-thiazol-5-yl)-pyrimidin-2-ylamino]-phenyl}-2-pyrrolidin-1-yl-acetamide |

TABLE 1-continued

Example compounds

| No. | Structure | Name |
|---|---|---|
| 54 | 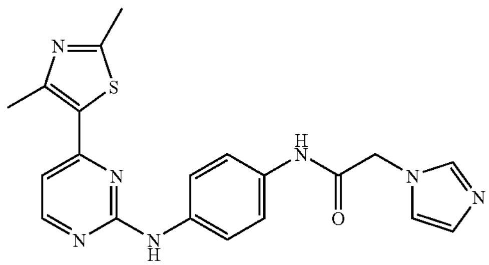 | N-{4-[4-(2,4-Dimethyl-thiazol-5-yl)-pyrimidin-2-ylamino]-phenyl}-2-imidazol-1-yl-acetamide |
| 55 | 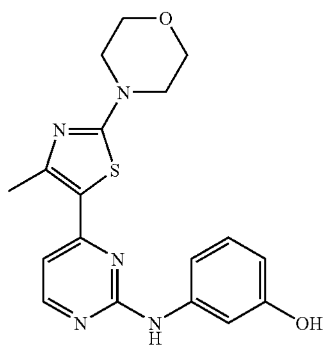 | 3-[4-(4-Methyl-2-morpholin-4-yl-thiazol-5-yl)-pyrimidin-2-ylamino]-phenol |
| 56 | 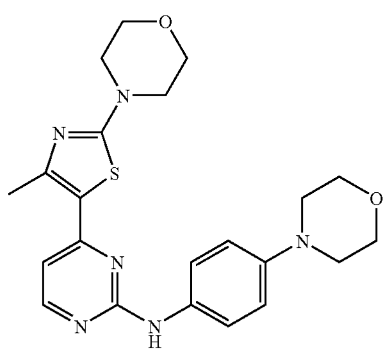 | [4-(4-Methyl-2-morpholin-4-yl-thiazol-5-yl)-pyrimidin-2-yl]-(4-morpholin-4-yl-phenyl)-amine |
| 57 | 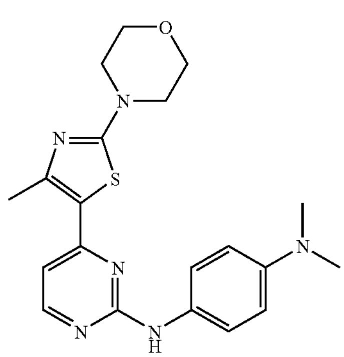 | N,N-Dimethyl-N'-[4-(4-methyl-2-morpholin-4-yl-thiazol-5-yl)-pyrimidin-2-yl]-benzene-1,4-diamine |

TABLE 1-continued

| No. | Structure | Name |
|---|---|---|
| 59 | 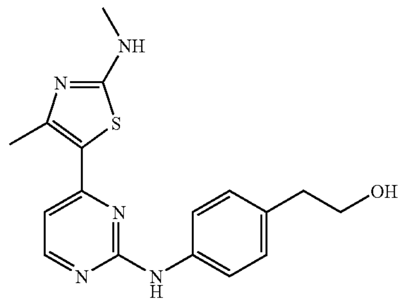 | 2-{4-[4-(4-Methyl-2-methylamino-thiazol-5-yl)-pyrimidin-2-ylamino]-phenyl}-ethanol |
| 61 | 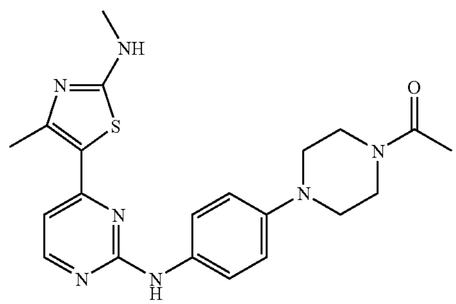 | 1-(4-{4-[4-(4-Methyl-2-methylamino-thiazol-5-yl)-pyrimidin-2-ylamino]-phenyl}-piperazin-1-yl)-ethanone |
| 62 | 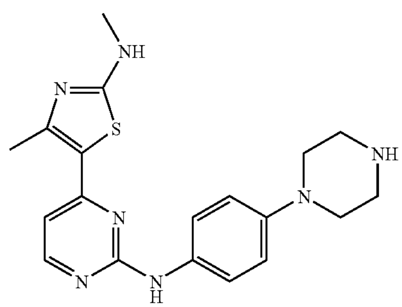 | [4-(4-Methyl-2-methylamino-thiazol-5-yl)-pyrimidin-2-yl]-(4-piperazin-1-yl-phenyl)-amine |
| 63 | 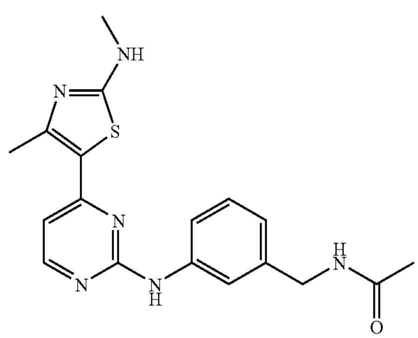 | N-{3-[4-(4-Methyl-2-methylamino-thiazol-5-yl)-pyrimidin-2-ylamino]-benzyl}-acetamide |

TABLE 1-continued

| No. | Structure | Name |
|---|---|---|
| 64 | 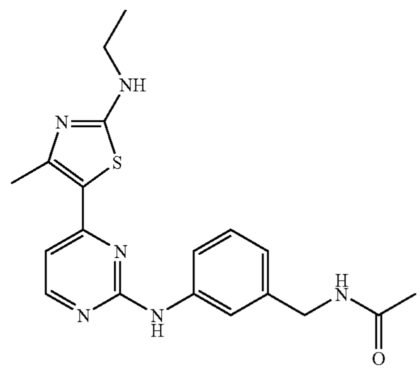 | N-{3-[4-(2-Ethylamino-4-methyl-thiazol-5-yl)-pyrimidin-2-ylamino]-benzyl}-acetamide |
| 65 | 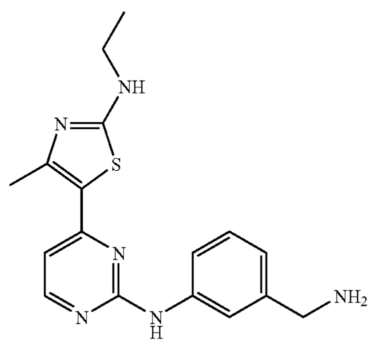 | (3-Aminomethyl-phenyl)-[4-(2-ethylamino-4-methyl-thiazol-5-yl)-pyrimidin-2-yl]-amine |
| 66 | 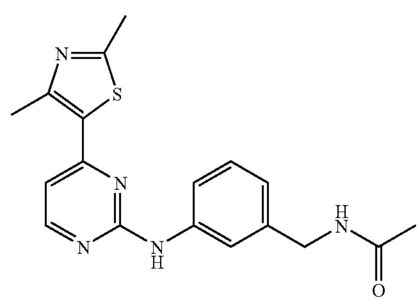 | N-{3-[4-(2,4-Dimethyl-thiazol-5-yl)-pyrimidin-2-ylamino]-benzyl}-acetamide |
| 67 | 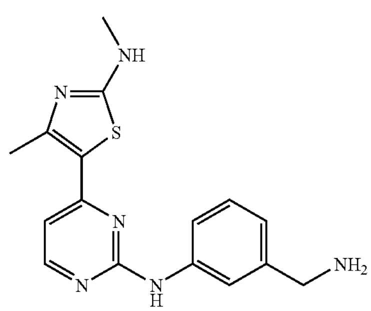 | (3-Aminomethyl-phenyl)-[4-(4-methyl-2-methylamino-thiazol-5-yl)-pyrimidin-2-yl]-amine |

TABLE 1-continued

Example compounds

| No. | Structure | Name |
|---|---|---|
| 68 | 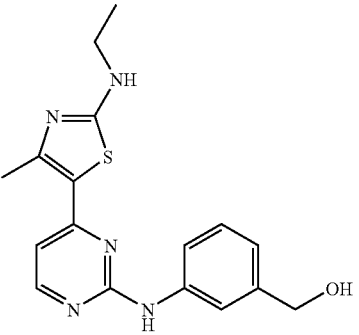 | {3-[4-(2-Ethylamino-4-methyl-thiazol-5-yl)-pyrimidin-2-ylamino]-phenyl}-methanol |
| 71 | 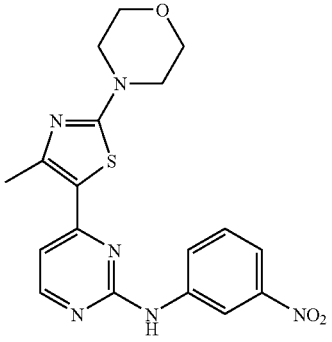 | [4-(4-Methyl-2-morpholin-4-yl-thiazol-5-yl)-pyrimidin-2-yl]-(3-nitro-phenyl)-amine |
| 72 | 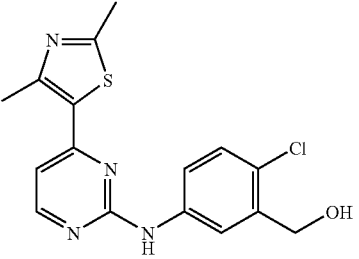 | {2-Chloro-5-[4-(2,4-dimethyl-thiazol-5-yl)-pyrimidin-2-ylamino]-phenyl}-methanol |
| 73 | 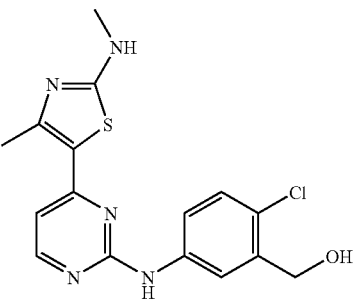 | {2-Chloro-5-[4-(4-methyl-2-methylamino-thiazol-5-yl)-pyrimidin-2-ylamino]-phenyl}-methanol |
| 76 | 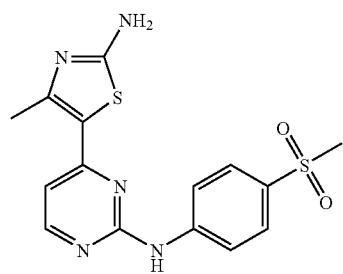 | [4-(2-Amino-4-methyl-thiazol-5-yl)-pyrimidin-2-yl]-(4-methanesulfonyl-phenyl)-amine |

TABLE 1-continued

| No. | Structure | Name |
|---|---|---|
| 77 | 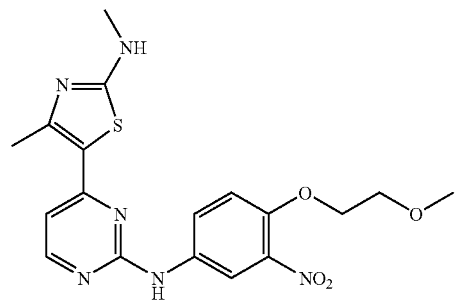 | [4-(2-Methoxy-ethoxy)-3-nitro-phenyl]-[4-(4-methyl-2-methylamino-thiazol-5-yl)-pyrimidin-2-yl]-amine |
| 81 | 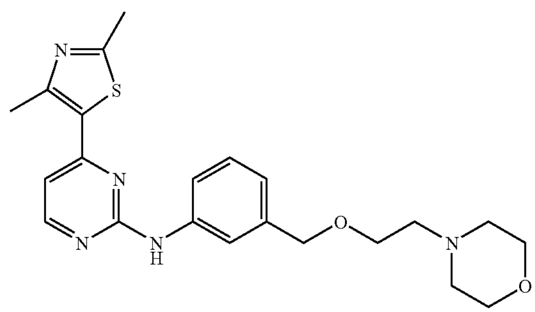 | [4-(2,4-Dimethyl-thiazol-5-yl)-pyrimidin-2-yl]-[3-(2-morpholin-4-yl-ethoxymethyl)-phenyl]-amine |
| 82 | 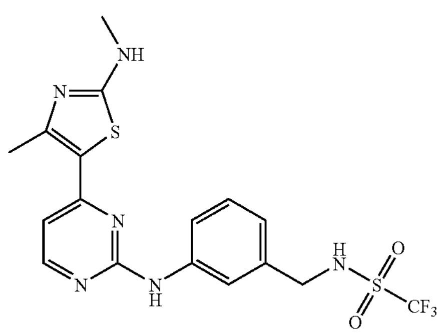 | C,C,C-Trifluoro-N-{3-[4-(4-methyl-2-methylamino-thiazol-5-yl)-pyrimidin-2-ylamino]-benzyl}-methanesulfonamide |
| 83 | 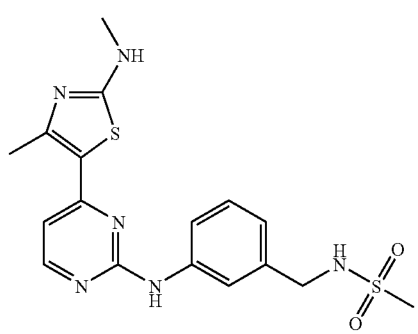 | N-{3-[4-(4-Methyl-2-methylamino-thiazol-5-yl)-pyrimidin-2-ylamino]-benzyl}-methanesulfonamide |

TABLE 1-continued

| No. | Structure | Name |
|---|---|---|
| 84 | 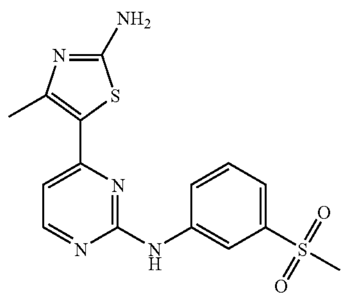 | [4-(2-Amino-4-methyl-thiazol-5-yl)-pyrimidin-2-yl]-(3-methanesulfonyl-phenyl)-amine |
| 85 | 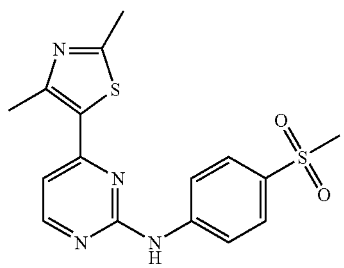 | [4-(2,4-Dimethyl-thiazol-5-yl)-pyrimidin-2-yl]-(4-methanesulfonyl-phenyl)-amine |
| 91 | 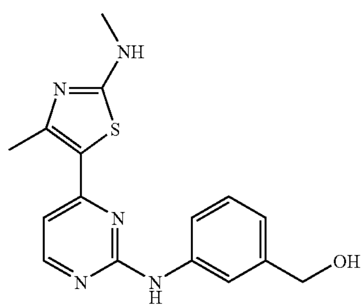 | {3-[4-(4-Methyl-2-methylamino-thiazol-5-yl)-pyrimidin-2-ylamino]-phenyl}-methanol |
| 92 | 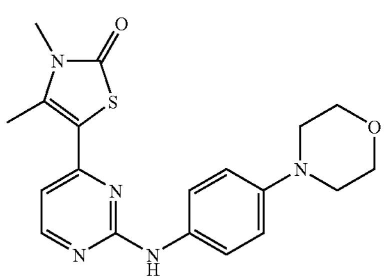 | 3,4-Dimethyl-5-[2-(4-morpholin-4-yl-phenylamino)-pyrimidin-4-yl]-3H-thiazol-2-one |
| 93 | 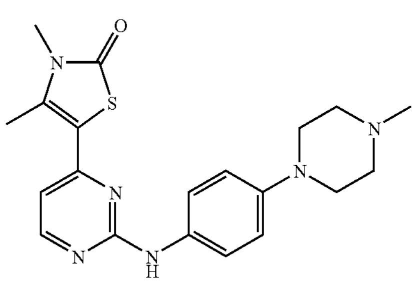 | 3,4-Dimethyl-5-{2-[4-(4-methyl-piperazin-1-yl)-phenylamino]-pyrimidin-4-yl}-3H-thiazol-2-one |

TABLE 2

Inhibition of protein kinases by example compounds (refer Table 1).

Kinase Inhibition IC$_{50}$ (μM)

| No. | CDK1 cyclin B[1] | CDK2 cyclin A[1] | CDK2 cyclin E[1] | CDK4 cyclin D1[1] | CDK7 cyclin H[1] | CDK9 cyclin T1[1] | GSK-3β[1] | PLK-1[1] | ARK-2[2] |
|---|---|---|---|---|---|---|---|---|---|
| 1 | 17 | 0.70 | 0.81 | 2.4 | 30 | 2.7 | >100 | 98 | 0.011 |
| 2 | 75 | 2.2 | 3.9 | 3.9 | 97 | 23 | >100 | >100 | |
| 3 | 71 | 4.7 | 0.43 | 1.4 | 106 | 12 | >100 | >150 | |
| 4 | 30 | 1.1 | 0.90 | 0.43 | 12 | 1.8 | >100 | >100 | |
| 5 | 5.6 | 1.1 | 0.87 | 1.7 | 5.6 | 6.1 | 21 | 35 | |
| 6 | 3.0 | 0.85 | 0.71 | 0.39 | 1.3 | 1.0 | 5.2 | 13 | |
| 7 | 4.2 | 1.3 | 1.8 | 0.62 | 2.2 | | | | |
| 8 | 4.9 | 1.1 | 1.2 | 0.36 | 0.97 | 0.51 | 39 | >150 | |
| 9 | 5.2 | 1.2 | 2.2 | 0.43 | 1.3 | 0.21 | | | |
| 10 | 51 | 4.4 | 15 | 11 | | | | | |
| 11 | 2.4 | 2.2 | 0.26 | 0.0098 | 0.019 | 1.1 | 6.0 | 19 | |
| 12 | 4.2 | 1.0 | 1.8 | 0.19 | 1.1 | 0.28 | 53 | 55 | |
| 13 | 5.6 | 0.57 | 0.28 | 0.67 | 0.37 | 0.042 | | | |
| 14 | | | 0.068 | 2.2 | | 0.34 | | | |
| 15 | 5.4 | 0.85 | 0.13 | 2.0 | 0.34 | 0.070 | 0.61 | >150 | |
| 16 | 2.8 | 0.65 | 0.32 | 6.7 | 1.1 | 0.11 | 0.68 | >150 | 2.8 |
| 17 | 2.0 | | 0.21 | | | | | | |
| 18 | | | 0.18 | 1.1 | | 0.53 | | | |
| 20 | 1.9 | 0.52 | 0.076 | 0.77 | | 0.037 | | | |
| 21 | 0.54 | 0.32 | 0.097 | 1.3 | 4.9 | 0.46 | 14 | >200 | |
| 22 | 0.24 | 0.098 | 0.0025 | 1.7 | 0.20 | 0.11 | 0.25 | >100 | |
| 23 | 3.1 | 1.4 | 0.19 | 3.0 | 0.81 | 0.40 | 1.2 | 24 | |
| 24 | | | 1.1 | 0.44 | | 0.0058 | | | |
| 25 | 9.4 | 3.0 | 0.22 | 0.97 | 3.2 | 0.68 | 0.083 | | |
| 28 | 36 | 12 | 2.6 | 29 | | | | | |
| 29 | 0.86 | 0.49 | 0.47 | 1.1 | 1.2 | | 0.56 | | |
| 31 | | | 0.30 | 5.6 | | | | | |
| 32 | | | 0.005 | 1.1 | | 0.0014 | 0.21 | | |
| 33 | | | 0.23 | 0.68 | | | | | |
| 34 | | | 1.4 | 7.0 | | 0.73 | | | |
| 35 | 15 | 3.0 | 0.80 | 4.7 | | 1.8 | | | |
| 36 | 33 | 13 | 3.4 | 8.8 | 4.0 | 4.8 | | | |
| 37 | >100 | 16 | 8.0 | 18 | | 6.3 | | | |
| 38 | 1.9 | 0.58 | 2.7 | 1.8 | | 1.1 | | | |
| 39 | 11 | 2.7 | 1.2 | 32 | | 15 | | | |
| 40 | 61 | 14 | 64 | 7.4 | | 8.9 | | | |
| 45 | 2.5 | 0.84 | 0.66 | 0.37 | 17 | 0.24 | | | |
| 48 | 12 | 1.7 | 2.1 | 2.6 | 3.5 | | | | |
| 50 | 3.4 | 0.89 | 0.39 | 0.95 | 13 | 0.0018 | | | |
| 51 | 11 | 2.9 | 1.7 | 0.40 | 9.6 | | | | |
| 52 | 2.5 | 1.3 | 0.44 | 0.18 | 2.0 | | | | |
| 53 | 5.2 | 5.3 | 0.52 | 0.040 | 0.44 | 0.093 | 23 | | |
| 54 | 1.3 | 57 | 0.098 | 0.032 | 2.1 | 0.11 | 19 | | |
| 55 | 2.4 | 61 | 0.079 | 1.0 | 2.2 | 2.1 | 67 | | |
| 56 | 18 | 68 | 0.60 | 0.022 | 0.85 | 17 | >100 | | |
| 57 | 7.7 | 73 | 0.35 | 0.071 | 0.19 | 12 | 74 | | |
| 59 | 0.71 | 0.11 | 0.14 | 0.086 | 2.6 | 0.47 | 2.2 | | |
| 61 | 2.5 | 2.8 | 0.60 | 0.042 | 2.3 | 1.5 | 6.8 | | |
| 62 | 0.98 | 1.5 | 0.21 | 0.0070 | 0.041 | 0.098 | 4.7 | | |
| 63 | 48 | 12 | 1.7 | 7.7 | 20 | 2.7 | 8.8 | 46 | |
| 64 | 0.74 | 0.31 | 0.080 | 0.13 | 0.59 | 0.10 | 2.1 | 18 | |
| 65 | | | 0.33 | 0.11 | | | | >100 | |
| 66 | 0.12 | 0.10 | 0.11 | 0.63 | 2.1 | | | | |
| 67 | | | 0.42 | 0.24 | | | | >100 | |
| 68 | 0.15 | 0.061 | 0.065 | 0.042 | 0.48 | | 0.82 | | |
| 71 | 0.33 | 0.0060 | 0.22 | | 2.4 | 4.2 | 2.4 | | |
| 72 | 62 | 12 | 0.73 | 25 | 9.6 | 4.1 | 48 | | |
| 73 | 1.7 | 1.3 | 1.0 | 0.23 | 2.0 | 0.55 | 5.2 | | |
| 76 | 1.8 | 0.14 | 0.15 | 3.2 | 11 | | 5.4 | | |
| 77 | 72 | 1.0 | 0.15 | 3.4 | 1.0 | 0.26 | 6.1 | | |
| 82 | 2.7 | 1.3 | 0.014 | 2.3 | 4.0 | | 1.2 | | |
| 83 | 0.48 | 0.15 | 0.025 | 0.67 | 0.37 | | 1.0 | | |
| 84 | 0.14 | 0.05 | 0.076 | 0.3 | 0.43 | | 0.30 | | |
| 85 | 0.048 | 0.001 | 0.028 | 3.8 | 11 | | | | |
| 91 | 0.12 | 0.10 | 0.11 | 0.63 | | | | | |
| 92 | 15 | 1.2 | 0.64 | 1.3 | 2.8 | | 0.47 | | |
| 93 | 4.4 | 1.1 | 0.84 | 0.51 | 0.36 | 0.3 | 0.43 | | |

[1] Refer to Table 3 for explanation of abbreviations;
[2] ARK-2: aurora kinase-2 (also known as aurora A kinase).

TABLE 3

Kinase specificity of selected compounds (IC$_{50}$, μM)

| Kinase | Compound 1 | 3 | 11 | 15 | 16 |
|---|---|---|---|---|---|
| CDK2/E[1] | 0.48 | 0.68 | 0.26 | 0.15 | 0.35 |
| CDK2/A[2] | 0.44 | 0.44 | 2.2 | 0.40 | 0.65 |
| CDK1/B1[3] | 21 | >100 | 2.4 | 1.6 | 2.8 |
| CDK4/D1[4] | 2.2 | 0.15 | 0.0098 | 1.6 | 6.7 |
| CDK7/H[5] | 56 | >100 | 0.019 | 0.39 | 0.97 |
| CDK9/T1[6] | 2.3 | 8.5 | 1.1 | 0.11 | 0.20 |
| ERK2[7] | >100 | >100 | >100 | >100 | >100 |
| p70/S6[8] | 2.3 | 2.6 | >100 | >100 | 8.0 |
| CK2[9] | >100 | >100 | >100 | >100 | >100 |
| PKCα[10] | >100 | >100 | >100 | >100 | 53 |
| Akt/PKB[11] | >100 | >100 | >100 | >100 | >100 |
| PKA[12] | 5.8 | 39 | 11 | 2.0 | 4.9 |
| SAPK2a[13] | >100 | >100 | >100 | >100 | >100 |
| PLK1[14] | >100 | >100 | 19 | >100 | >100 |
| CaMKII[15] | 26 | >100 | 56 | 3.9 | 11 |
| Abl[16] | >100 | 50 | 72 | 0.76 | 1.5 |
| GSK-3[17] | >100 | >100 | 6.0 | 0.54 | 0.68 |

[1]CDK2/cyclin E complex;
[2]CDK2/cyclin A complex;
[3]CDK 1/cyclin B1 complex;
[4]CDK4/cyclin D1 complex;
[5]CDK7/cyclin H/MAT 1 complex;
[6]CDK9/cyclin T1 complex;
[7]extracellular-signal-regulated kinase 2;
[8]p70 ribosomal protein S6 kinase;
[9]casein kinase 2;
[10]protein kinase C α;
[11]protein kinase B;
[12]cAMP-dependent protein kinase;
[13]stress-activated protein kinase 2a;
[14]polo-like kinase 1;
[15]calmodulin-depependent kinase II;
[16]Ableson tyrosine kinase;
[17]glycogen synthase kinase 3β.

TABLE 4

Anti-proliferative activity against human cancer cell lines (refer Table 1)

72-h MTT IC$_{50}$ (μM)

| No. | A549 | HT29 | Saos-2 |
|---|---|---|---|
| 1 | 2.1 | 1.7 | 1.9 |
| 2 | 3.5 | 3.3 | 4.8 |
| 3 | 3.7 | 2.8 | 3.1 |
| 4 | 0.77 | 0.92 | 1.2 |
| 5 | 3.8 | 2.2 | 3.9 |
| 6 | 1.3 | 1.1 | 0.78 |
| 7 | 3.9 | 1.6 | 1.6 |
| 8 | 0.61 | 0.80 | 0.38 |
| 9 | 3.0 | 2.0 | 2.0 |
| 10 | 11 | 6.4 | |
| 11 | 2.2 | 1.6 | 3.6 |
| 12 | 0.71 | 0.74 | 0.43 |
| 13 | 3.1 | 2.8 | 1.9 |
| 14 | 0.99 | 0.73 | 1.5 |
| 15 | 1.1 | 1.0 | 1.9 |
| 16 | 0.53 | 0.29 | |
| 17 | 1.1 | 1.2 | 1.2 |
| 18 | 2.5 | 2.4 | 1.1 |
| 20 | 5.8 | 6.3 | |
| 21 | 8.6 | 4.1 | 4.3 |
| 22 | 0.81 | 0.52 | 0.60 |
| 23 | 3.8 | 1.1 | 4.4 |
| 24 | 0.14 | 0.14 | 0.17 |
| 25 | 0.97 | 1.3 | 1.6 |
| 28 | 9.9 | 6.74 | 15 |
| 29 | 0.69 | 2.6 | 0.72 |
| 31 | 2.0 | 4.1 | 0.81 |
| 32 | 0.10 | 0.17 | 0.16 |
| 33 | 0.33 | 0.11 | 0.30 |
| 34 | 3.9 | 3.2 | 3.3 |
| 35 | 15 | 7.7 | 26 |
| 36 | 26 | 9.6 | 38 |
| 37 | 35 | 15 | 73 |
| 38 | 2.7 | 1.7 | 5.3 |
| 39 | 0.80 | 0.72 | 0.95 |
| 40 | 4.4 | 0.73 | 4.3 |
| 45 | 2.6 | 2.2 | 2.8 |
| 47 | 2.7 | 0.35 | 1.6 |
| 48 | 3.0 | 2.6 | 3.8 |
| 50 | 0.16 | 0.16 | 0.16 |
| 51 | 1.9 | 1.4 | 1.1 |
| 52 | 1.6 | 1.6 | 1.1 |
| 53 | 0.77 | 0.95 | 0.53 |
| 54 | 2.9 | 2.7 | 1.9 |
| 55 | 2.3 | 5.1 | 1.4 |
| 56 | 4.4 | 2.9 | 5.0 |
| 57 | 2.7 | 0.24 | 3.8 |
| 59 | 2.4 | 1.7 | 1.9 |
| 61 | 0.72 | 0.53 | 1.0 |
| 62 | 0.19 | 0.18 | 0.26 |
| 63 | 0.98 | 1.4 | 1.2 |
| 64 | 0.19 | 0.41 | 0.34 |
| 65 | 3.2 | 4.8 | 0.65 |
| 67 | 14 | 14 | 1.1 |
| 71 | 80 | 71 | 10 |
| 72 | 32 | 20 | 18 |
| 73 | 1.5 | 5.5 | 2.9 |
| 76 | 5.8 | 1.8 | 1.3 |
| 77 | 0.31 | 0.21 | 0.35 |

TABLE 5

In vitro antiproliferative activity of selected compounds (72-h MTT, IC$_{50}$, μM)

| Cell line Type | Designation | Compound 1 | 11 | 15 | 16 |
|---|---|---|---|---|---|
| Bone osteosarcoma | Saos-2 | 0.1 | 3.7 | 0.4 | 0.6 |
| Bone osteosarcoma | U2OS | 2.1 | 2.3 | 1.02 | 0.48 |
| Breast | MCF-7 | >5 | 1.9 | 0.9 | 0.39 |
| Cervix | Hela | 1.8 | 6.2 | 0.7 | 0.4 |
| Colon | HT29 | 1.1 | 1.6 | 0.5 | 0.3 |
| Colon | Lovo | 0.9 | 2.0 | 0.7 | 0.3 |
| Colon | H1299 | 0.9 | 1.1 | 1.3 | 0.6 |
| Colon | HCT-116 | 0.9 | 0.6 | 0.6 | 0.3 |
| Gastric adenocarcinoma | AGS | 1.1 | 1.3 | 1.1 | 0.3 |
| Leiomyosarcoma | SKUT-1B | | 0.3 | 0.2 | 0.1 |
| Leiomyosarcoma | SKUT-1 | 0.9 | 0.8 | 0.9 | 0.2 |
| Chronic myelogenous leukaemia | K562 | 3.8 | 2.1 | 4.6 | 2.5 |
| Leukemia | CCRF-CEM | 0.9 | 0.5 | 2.6 | 1.1 |
| Promyelocytic leukaemia | HL60 | 1.8 | 1.7 | 2.2 | 0.6 |
| Lung | nci-H460 | 0.2 | 0.7 | 1.2 | 0.3 |
| Lung | A549 | 1.0 | 2.2 | 0.6 | 0.5 |
| Neuroblastoma | SK-N-MC | 0.3 | 0.6 | 0.5 | 0.4 |
| Osteogenic sarcoma | SJSA-1 | >5 | 4.3 | 1.9 | 1.0 |
| Prostate | DU-145 | 1.5 | 1.0 | 1.3 | 0.6 |
| Skin keratinocytes | Hacat | 1.1 | 1.0 | 1.5 | 1.1 |
| Uterine | Messa | 0.2 | 0.1 | 0.9 | 0.4 |
| Uterine | Messa-Dx5 | 0.2 | 0.2 | 0.4 | 0.1 |
| Average (all transformed cells) | | 1.1 | 1.6 | 1.2 | 0.6 |
| SD (all transformed cells) | | 0.9 | 1.4 | 1.0 | 0.5 |

TABLE 5-continued

In vitro antiproliferative activity of selected compounds (72-h MTT, IC$_{50}$, μM)

| Cell line | | Compound | | | |
|---|---|---|---|---|---|
| Type | Designation | 1 | 11 | 15 | 16 |
| Median (all transformed cells) | | 1.0 | 1.1 | 0.9 | 0.4 |
| Foreskin fibroblast (non-transformed) | Hs27 | >5 | 19 | 1.7 | >5 |
| Foetal lung fibroblast (non-transformed) | IMR-90 | >5 | 31 | 2.5 | 1.7 |
| Foetal lung fibroblast (non-transformed) | WI38 | >5 | 22 | >5 | 1.4 |

TABLE 6

Summary of anti-HIV activity

| | HIV-1/PBMC | | | |
|---|---|---|---|---|
| Compound | IC$_{50}$ (nM) | IC$_{90}$ (nM) | PBMC TC$_{50}$ (μM) | TI |
| AZT[a] | 4 | 10 | >1 | >231 |
| 1 | 1,327 | 2,645 | 6.1 | 4.6 |
| 3 | 297 | 679 | >100 | >337 |
| 4 | 166 | 295 | 9.4 | 57 |
| 15 | 124 | 385 | 2.4 | 20 |
| 53 | 812 | 871 | 1.6 | 1.9 |

[a]AZT: Azidothymidine; anti-HIV drug in clinical use as positive control.

The invention claimed is:

1. A compound, which is [4-(4-Methyl-2-methylamino-thiazol-5-yl)-pyrimidin-2-yl]-(4-piperazin-1-yl-phenyl)-amine [62].

2. A pharmaceutical composition comprising the compound according to claim 1, admixed with a pharmaceutically acceptable diluent, excipient or carrier.

3. A method of treating a proliferative disorder, said method comprising administering to a mammal a therapeutically effective amount of the compound according to claim 1, such that the proliferative disorder is treated, wherein the compound is administered in an amount sufficient to inhibit at least one CDK enzyme, and wherein said proliferative disorder is selected from the group consisting of bone osteosarcoma, breast cancer, cervical cancer, colon cancer, gastric adenocarcinoma, leiomyosarcoma, chronic myelogenous leukemia, lung cancer, neuroblastoma, osteogenic sarcoma, prostate cancer, and uterine cancer.

4. The method according to claim 3, wherein said compound is administered in combination with one or more other anticancer compounds.

5. The method according to claim 3, wherein the CDK enzyme is CDK1, CDK2, CDK3, CDK4, CDK6, CDK7, CDK8 or CDK9.

6. A method of treating an HIV-1 viral disorder, said method comprising administering to a mammal a therapeutically effective amount of the compound of claim 1, such that said HIV-1 viral disorder is treated.

\* \* \* \* \*